US008071560B2

(12) United States Patent
Mohapatra et al.

(10) Patent No.: US 8,071,560 B2
(45) Date of Patent: Dec. 6, 2011

(54) MATERIALS AND METHODS FOR REDUCING INFLAMMATION BY INHIBITION OF THE ATRIAL NATRIURETIC PEPTIDE RECEPTOR

(75) Inventors: Shyam S. Mohapatra, Lutz, FL (US); Weidong Xu, Tampa, FL (US); Xiaoyuan Kong, Tampa, FL (US); Xiaoqin Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 99 days.

(21) Appl. No.: 11/799,225

(22) Filed: Apr. 30, 2007

(65) Prior Publication Data

US 2007/0265204 A1 Nov. 15, 2007

Related U.S. Application Data

(63) Continuation-in-part of application No. 11/059,814, filed on Feb. 17, 2005.

(60) Provisional application No. 60/521,072, filed on Feb. 17, 2004, provisional application No. 60/796,278, filed on Apr. 28, 2006.

(51) Int. Cl.
*A61K 48/00* (2006.01)
(52) U.S. Cl. ...... 514/44; 536/24.5; 536/24.31; 536/24.1
(58) Field of Classification Search .................. None
See application file for complete search history.

(56) References Cited

U.S. PATENT DOCUMENTS

| | | | |
|---|---|---|---|
| 4,957,735 A | 9/1990 | Huang | |
| 5,013,556 A | 5/1991 | Woodle et al. | |
| 5,043,164 A | 8/1991 | Huang et al. | |
| 5,087,617 A | 2/1992 | Smith | |
| 5,093,246 A | 3/1992 | Cech et al. | |
| 5,116,742 A | 5/1992 | Cech et al. | |
| 5,135,917 A | 8/1992 | Burch | |
| 5,144,019 A | 9/1992 | Rossi et al. | |
| 5,168,053 A | 12/1992 | Altman et al. | |
| 5,176,996 A | 1/1993 | Hogan et al. | |
| 5,180,818 A | 1/1993 | Cech et al. | |
| 5,190,931 A | 3/1993 | Inouye | |
| 5,272,262 A | 12/1993 | Rossi et al. | |
| 5,595,756 A | 1/1997 | Bally et al. | |
| 5,646,032 A | 7/1997 | ter Meulen et al. | |
| 5,686,101 A | 11/1997 | Tagawa et al. | |
| 5,691,310 A | 11/1997 | Vesely | |
| 5,705,187 A | 1/1998 | Unger | |
| 5,817,856 A | 10/1998 | Tirosh et al. | |
| 5,820,873 A | 10/1998 | Choi et al. | |
| 5,840,341 A | 11/1998 | Watts et al. | |
| 6,013,630 A | 1/2000 | Shimkets | |
| 6,028,055 A | 2/2000 | Lowe et al. | |
| 6,184,037 B1 | 2/2001 | Rolland et al. | |
| 6,506,559 B1 | 1/2003 | Fire et al. | |
| 6,528,245 B2 | 3/2003 | Sanchez-Ramos et al. | |
| 6,943,147 B2 | 9/2005 | Vesely | |
| 7,022,828 B2 | 4/2006 | McSwiggen | |
| 7,354,908 B2 | 4/2008 | Mohapatra et al. | |
| 7,488,713 B2 * | 2/2009 | Vesely | 514/12 |
| 7,595,303 B1 | 9/2009 | Mohapatra et al. | |
| 7,655,772 B2 | 2/2010 | Mohapatra | |
| 7,825,092 B2 | 11/2010 | Vesely | |
| 7,846,900 B2 | 12/2010 | Vesely | |
| 2001/0027181 A1 | 10/2001 | Kitakaze | |
| 2002/0146821 A1 | 10/2002 | Sanchez-Ramos et al. | |
| 2002/0193579 A1 | 12/2002 | Usman et al. | |
| 2003/0069186 A1 | 4/2003 | Burnett et al. | |
| 2003/0073628 A1 | 4/2003 | Shailubhai et al. | |
| 2003/0138793 A1 | 7/2003 | Su et al. | |
| 2003/0147943 A1 | 8/2003 | Luo et al. | |
| 2003/0204063 A1 | 10/2003 | Gravel et al. | |
| 2004/0002458 A1 | 1/2004 | Seilhamer et al. | |
| 2004/0067889 A1 | 4/2004 | Belenky et al. | |
| 2004/0138134 A1 | 7/2004 | Golembo et al. | |
| 2004/0146549 A1 | 7/2004 | Ben-Sasson et al. | |
| 2004/0171550 A1 | 9/2004 | Backstrom et al. | |
| 2004/0203081 A1 | 10/2004 | James et al. | |
| 2004/0213782 A1 | 10/2004 | Wax | |
| 2004/0224903 A1 | 11/2004 | Berry et al. | |
| 2004/0266673 A1 | 12/2004 | Bakis et al. | |
| 2005/0008617 A1 | 1/2005 | Chen et al. | |
| 2005/0014287 A1 | 1/2005 | Friese et al. | |
| 2005/0014289 A1 | 1/2005 | Parsons et al. | |

(Continued)

FOREIGN PATENT DOCUMENTS

WO  WO 99/32619 A1  7/1999

(Continued)

OTHER PUBLICATIONS

Xie et al. DDt 2006, vol. 1(11): 67-73.* Elbashir, S.M. et al. "Duplexes of 21-nucleotide RNAs mediate RNA interference in cultured mammalian cells" *Nature*, May 24, 2001, 411:494-498.
Ivanova, K. et al. "Differential Expression of Functional Guanylyl Cyclases in Melanocytes: Absence of Nitric-Oxide-Sensitive Isoform in Metastatic Cells" *Journal of Investigative Dermatology*, Mar. 2001, 116(3):409-416.
Kong, X. et al. "Mice Deficient in Atrial Natriuretic Peptide Receptor A (NPRA) Exhibit Decreased Lung Inflammation: Implication of NPRA Signaling in Asthma Pathogenesis" *Journal of Allergy and Clinical Immunology*, Jan. 2007, 119(1):S127, abstract 501.
Mizuguchi, M. et al. "Bronchoprotective effects of atrial natriuretic peptide against propanolol-induced bronchoconstriction after allergic reaction in guinea pigs" *Clinical and Experimental Allergy*, 2000, 30:439-444.

(Continued)

*Primary Examiner* — Kimberly Chong
(74) *Attorney, Agent, or Firm* — Saliwanchik, Lloyd & Eisenschenk

(57) ABSTRACT

This invention pertains to inhibitors of atrial natriuretic peptide receptor A (NPRA) function, such as small interfering RNA (siRNA), useful for reducing the inflammation associated with many human diseases, such as asthma, respiratory syncytial virus (RSV) infection, and cancers (such as melanoma, lung cancer, and/or ovarian cancer) by interfering with NPRA gene expression or otherwise reducing NPRA function within a subject; and methods for treating a subject suffering from, or at risk of developing, an inflammatory disease, respiratory allergy (such as allergic rhinitis and asthma), viral infection, and/or cancer by administering such NPRA inhibitors to the subject.

16 Claims, 16 Drawing Sheets

U.S. PATENT DOCUMENTS

| | | | |
|---|---|---|---|
| 2005/0209139 A1 | 9/2005 | Vesely | |
| 2005/0266093 A1 | 12/2005 | Mohapatra | |
| 2005/0272650 A1* | 12/2005 | Mohapatra | 514/12 |
| 2006/0014689 A1 | 1/2006 | Vesely | |
| 2006/0110359 A1 | 5/2006 | Sanchez-Ramos et al. | |
| 2007/0036867 A1 | 2/2007 | Mohapatra et al. | |
| 2007/0116767 A1 | 5/2007 | Mohapatra | |
| 2007/0265204 A1 | 11/2007 | Mohapatra et al. | |
| 2008/0039394 A1 | 2/2008 | Vesely | |
| 2008/0070858 A1 | 3/2008 | Mohapatra | |
| 2008/0214437 A1 | 9/2008 | Mohapatra et al. | |
| 2009/0062206 A1 | 3/2009 | Vesely | |
| 2009/0170196 A1 | 7/2009 | Vesely | |
| 2009/0176706 A1 | 7/2009 | Mohapatra | |
| 2011/0034386 A1 | 2/2011 | Vesely | |

FOREIGN PATENT DOCUMENTS

| | | |
|---|---|---|
| WO | WO 00/71576 A2 | 11/2000 |
| WO | WO 01/68836 A3 | 9/2001 |
| WO | WO 01/75164 A3 | 10/2001 |
| WO | WO 01/92513 A1 | 12/2001 |
| WO | WO 2004/011498 A3 | 2/2004 |
| WO | WO 2004/022003 A3 | 3/2004 |
| WO | WO 2004/022579 A3 | 3/2004 |
| WO | WO 2005/094420 A3 | 10/2005 |
| WO | WO 2007/127487 A2 | 11/2007 |
| WO | WO 2009/073527 A2 | 6/2009 |

OTHER PUBLICATIONS

Pandey, K.N. et al. "Molecular Cloning and Expression of Murine Guanylate Cyclase/Atrial Natriuretic Factor Receptor cDNA" *The Journal of Biological Chemistry*, Jul. 25, 1990, 265(21):12342-12348.

Svoboda, P. et al. "Selective reduction of dormant maternal mRNAs in mouse oocytes by RNA interference" *Development*, Oct. 2000, 127:4147-4156.

Tuschl, T. et al. "Targeted mRNA degradation by double-stranded RNA in vitro" *Genes & Development*, Dec. 1999, 13:3191-3197.

Wang, X. et al. "siRNA Targeting the Natriuretic Peptide Receptor-A Prevents Airway Inflammation in a Mouse Model of Allergic Asthma" *Journal of Allergy and Clinical Immunology*, Jan. 2007, 119(1):S131, abstract 515.

"Designing Custom Peptides" from Technical Bulletin of SIGMA Genosys, http://www.sigma-genosys.com/peptide_design.asp; accessed Dec. 16, 2004, 2 pages.

Office Action dated Aug. 9, 2007 in U.S. Appl. No. 11/059,814, filed Feb. 17, 2005.

Advisory Action dated Oct. 15, 2008 in U.S. Appl. No. 11/059,814, filed Feb. 17, 2005.

Office Action dated Apr. 25, 2008 in U.S. Appl. No. 11/059,814, filed Feb. 17, 2005.

Office Action dated Feb. 1, 2011 in U.S. Appl. No. 12/259,110, filed Feb. 1, 2011.

Office Action dated Jun. 1, 2009 in U.S. Appl. No. 11/998,792, filed Nov. 30, 2007.

Office Action dated Dec. 11, 2009 in U.S. Appl. No. 11/998,792, filed Nov. 30, 2007.

Office Action dated May 18, 2010 in U.S. Appl. No. 11/998,792, filed Nov. 30, 2007.

Office Action dated Oct. 13, 2010 in U.S. Appl. No. 11/998,792, filed Nov. 30, 2007.

Benson, J.D. et al. "Validating cancer drug targets" *Nature*, May 2006, 441:451-456.

Berendsen, H.J.C. "A Glimpse of the Holy Grail?" *Science*, Oct. 23, 1998, 282(5389):642-643.

Bradley, C.M. et al. "Limits of Cooperativity in a Structurally Modular Protein: Response of the Notch Ankyrin Domain to Analogous Alanine Substitutions in Each Repeat" *J Mol Biol*, 2002, 324:373-386.

Brafford, P. et al. "Gene expression profiling of melanoma cells—searching the haystack" *Journal of Translational Medicine*, 2005, 3:2, pp. 1-2.

Carr, K.M. et al. "Gene-expression profiling in human cutaneous melanoma" *Oncogene*, 2003, 22:3076-3080.

Chen, J.H. "Application of cationic polymer vector for gene delivery systems" Yao Xue Xue Bao, Apr. 2003, 38(4):316-20, abstract.

Chengalvala, M.V. et al. "Gene Expression Profiling and its Practice in Drug Development" *Current Genomics*, 2007, 8(4):262-270.

Chin, L. et al. "Malignant melanoma: genetics and therapeutics in the genomic era" *Genes & Development*, 2006, 20:2149-2182.

De Wit, N.J.W. et al. "Analysis of differential gene expression in human melanocytic tumour lesions by custom made oligonucleotide arrays" *British Journal of Cancer*, 2005, 92:2249-2261.

Gogas, H. et al. "Biomarkers in melanoma" *Annals of Oncology*, Aug. 2009, 20(Supplement 6):vi8-vi13.

Haberman, A.B. "Strategies to Move Beyond Target Validation" *Genetic Engineering News*, Dec. 2005, 25(21):36.

Hulks, G. et al. "Bronchodilator effect of atrial natriuretic peptide in asthma" *Br Med J*, Oct. 28, 1989, 299:1081-1082.

Levy, J.A. et al. "Inactivation of Murine RNA Tumor Viruses by Isatin Beta-Thiosemicarbazone" *Virology*, Oct. 15, 1976, 74(2):426-431.

Lobbezoo, M.W. et al. "Signal Transduction Modulators for Cancer Therapy: From Promise to Practice?" *The Oncologist*, 2003, 8:210-213.

Martinez, S.R. et al. "Molecular Markers in Malignant Cutaneous Melanoma: Gift Horse or One-Trick Pony?" *Journal of Cellular Biochemistry*, 2005, 96:473-483.

Neidle, S. editor, "Failure Modes in the Discovery Process" *Cancer Drug Design and Discovery*, 2008, Elsevier/Academic Press, pp. 427-431.

Ngo, J.T. et al. "Computational Complexity, Protein Structure Prediction, and the Levinthal Paradox" *The Protein Folding Problem and Tertiary Structure Prediction*, 1994, Birkhäuser Boston, Le Grand Edition, pp. 491-495.

Rahmanto, Y.S. et al. "Identification of distinct changes in gene expression after modulation of melanoma tumor antigen p97 (melanotransferrin) in multiple models in vitro and in vivo" *Carcinogenesis*, 2007, 28(10):2172-2183.

Rudinger, J. "Characteristics of the amino acids as components of a peptide hormone sequence" *Peptide Hormones*, Biological Council: The Co-ordinating Committee for Symposia on Drug Action; J.A. Parsons, editor; Baltimore: University Park Press, Jun. 1976, pp. 1-7.

Schinzel, R. at al. "The phosphate recognition site of *Escherichia coli* maltodextrin phosphorylase" *FEBS Letters*, Jul. 1991, 286(1 and 2):125-128.

Schwab, G. et al. "An approach for new anticancer drugs: Oncogene-targeted antisense DNA" *Ann Oncol*, 1994, 5(Supplement 4):S55-S58.

Schwarze, J. et al. "Respiratory Syncytial Virus Infection Results in Airway Hyperresponsiveness and Enhanced Airway Sensitization to Allergen" *J Clin Invest*, 1997, 99:226-233.

Seftor, E.A. et al. "Expression of multiple molecular phenotypes by aggressive melanoma tumor cells: role in vasculogenic mimicry" *Critical Reviews in Oncology/Hematology*, 2002, 44:17-27.

Skubitz, A.P.N. et al. "Differential gene expression identifies subgroups of ovarian carcinoma" *Translational Research*, Nov. 2006, 148(5):223-248.

Sporn, M.B. et al. "Chemoprevention of cancer" *Carcinogenesis*, 2000, 21(3):525-530.

Vesely, D.L. et al. "The N-Terminus of the Atrial Natriuretic Factor Prohormone in the Pleural Fluid of Congestive Heart Failure Patients" *Chest*, 1990, 97(6):1295-1298.

Vesely, D.L. "Atrial Natriuretic Hormones Originating from the N-Terminus of the Atrial Natriuretic Factor Prohormone" *Clin Exp Pharmacol Physiol*, 1995, 22(2):108-114.

Vesely, D.L. et al. "Long-Acting Natriuretic Peptide, Vessel Dilator, and Kaliuretic Peptide Enhance the Urinary Excretion Rate of $\beta_2$-Microglobulin" *Metabolism*, Dec. 2000, 49(12):1592-1597.

Vesely, D.L. "Atrial natriuretic peptides: anticancer agents" *J Investig Med.*, 2005, 53(7):360-365.

Vita, M. et al. "The Myc oncoprotein as a therapeutic target for human cancer" *Seminars in Cancer Biology*, 2006, 16:318-330.

Voet, D. et al. editors, "Section 9-3: Abnormal Hemoglobins" *Biochemistry*, 2nd Edition; New York: John Wiley & Sons, 1995, pp. 235-241.

Winnepennickx, V. et al. "Gene Expression Profiling of Primary Cutaneous Melanoma and Clinical Outcome" *Journal of the National Cancer Institute*, Apr. 5, 2006, 98(7):472-482.

Wong, H.H. et al. "Pancreatic cancer: molecular pathogenesis and new therapeutic targets" *Nat Rev Gastroenterol Hepatol*, 2009, 6:412-422.

Yang, J. et al. "Conditional ablation of *Ikkb* inhibits melanoma tumor development in mice" *The Journal of Clinical Investigation*, Jul. 2010, 120(7):2563-2574.

Fluge, T. et al. "Bronchodilation using combined urodilatin—albuterol administration in asthma: a randomized, double-blind, placebo-controlled trial" *European Journal of Medical Research*, 1999, 4(10):411-415.

Sprenger, H. et al. "The lack of receptors for atrial natriuretic peptides on human monocytes prevents a rise of cGMP and induction of tumor necrosis factor-alpha synthesis" *Immunobiology*, Sep. 1991, 183(1-2):94-101.

Sun, Y. et al. "Atrial Natriuretic Peptide and Long Acting Natriuretic Peptide Inhibit ERK ½ in Prostate Cancer Cells" *Anticancer Research*, 2006, 26:4143-4148.

Sun, Y. et al. "Vessel Dilator and Kaliuretic Peptide Inhibit ERK ½ Activation in Human Prostate Cancer Cells" *Anticancer Research*, 2006, 26:3217-3222.

Vesely, D.L. "Aprotinin blocks the binding of pro atrial natriuretic peptides 1 to 30, 31 to 67, and 99-126 to human placental membranes" *Am J Obstet Gynecol*, 1991, 165(3)567-573.

Clinical Aspects of Cancer, Diagnosis from Merck Manual, pp. 1-5, Jul. 25, 2007.

Introduction to Cancer from Merck Manual, p. 1, Jul. 25, 2007.

Peptide hormones from http://web.indstate.edu/theme/mwking/peptide-hormones.html, pp. 1-15, Jul. 23, 2007.

Abadi, A.H. et al. "Synthesis of 3-substituted-2-oxoindole analogues and their evaluation ans kinase inhibitors, anticancer and antiangiogenic agents" *European Journal of Medicinal Chemistry*, 2006, 41(3):296-305.

Abbey, S. and Potter, L. "Lysophosphatidic acid inhibits C-type natriuretic peptide activation of guanylyl cyclase-B" *Endocrinology*, 2003, 144:240-246.

Ahn, K.S. at al. "Simvastatin Potentiates TNF-a-lnduced Apoptosis through the Down-Regulation of NF-κB-Dependent Antiapoptotic Gene Products: Role of IκBa Kinase and TGF-β-Activated Kinase-1" *Journal of Immunology*, 2007, 178:2507-2516.

Allen, T.M. et al. "Large unilamellar liposomes with low uptake into the reticuloendothelial system" *FEBS Letters*, 1987, 223:42-46.

Angus, R.M. et al. "Effect of inhaled atrial natriuretic peptide on methacholine induced bronchoconstriction in asthma" *Clin Exp Allergy*,1994, 24:784-788.

Angus, R.M. et al. "Effect of inhaled atrial natriuretic peptide and a neutral endopeptidase inhibitor on histamine-induced bronchoconstriction" *Am. J. Respir. Crit. Care Med.*, 1995, 151:2003-2005.

Arenberg, D. "Chemokines in the Biology of Lung Cancer" *Journal of Thoracic Oncology*, 2006, 1(4):287-288.

Ashworth, T. et al. "Cutting Edge: TFII-I Controls B Cell Proliferation via Regulating NF-κB" *Journal of Immunology*, 2007, 178:2631-2635.

Auerbach, R. et al. "Angiogenesis assays, Problems and Pitfalls" *Cancer and Metastasis Reviews* 2000, 19: 167-172.

Baldini, P.M. et al. "Decrease of polyamine levels and enhancement of transglutaminase activity in selective reduction of B16-F10 melanoma cell proliferation induced by atrial natriuretic peptide" *Melanoma Research*, 2006, 16:501-507.

Bass, B.L. "RNA interference: The short answer" *Nature*, 2001, 411:428-429.

Bernstein, E. et al. "The rest is silence" *RNA*, 2001, 7:1509-1521.

Bernstein, E. et al. "Role for a bidentate ribonuclease in the initiation step of RNA interference" *Nature*, Jan. 2001, 409:363-366.

Bliss, D. et al. "Expression of the atrial natriuretic factor gene in small cell lung cancer tumors and tumor cell lines" *J Natl Can Inst*, 1990, 82:305-310.

Boiteau, R. at al. "Increase in atrial natriuretic factor (ANF) in acute severe asthma (ASA)" *Am Rev Res Dis.*, 1988, 137:A484.

Bryan, P.M. et al. "The Atrial Natriuretic Peptide Receptor (NPR-A/GC-1) is Dephosphorylated by Distinct Microcystin-sensitive and Magnesium-dependent Protein Phosphatase" *J. Biol. Chem.* 2002, 277(18): 16041-16047.

Cane, A. et al. "The Endogenous Oxindoles 5-Hydroxyoxindole and Isatin Are Antiproliferative and Proapoptotic" *Biochemical and Biophysical Research Communications*, 2000, 276:379-384.

Carthew, R.W. "Gene silencing by double-stranded RNA" *Current Opinion in Cell Biology*, 2001, 13:244-248.

Chanez, P. et al. "Atrial natriuretic factor (ANF) is a potent bronchodilator in asthma" *J. Allergy Clin. Immunol.*, 1990, 86:321-324.

Chen, J. et al. "Therapeutic benefit of intracerebral transplantation of bone marrow stromal cells after cerebral ischemia in rats" *J. Neurological Sci.*, 2001, 189:49-57.

Chen, J. et al. "Therapeutic benefit of intravenous administration of bone marrow stromal cells after cerebral ischemia in rats" *Stroke*, 2001, 32:1005-1011.

Chen, X. et al. "Human bone marrow stromal cell cultures" *J Neurosci Res*, 2002, 69:687-691.

Chen, X. at al. "Ischemic rat brain extracts induce human marrow stromal cell growth factor production" *Neuropathology*, 2002, 22:275-279.

Chen, S. et al. "1,25 Dihydroxyvitamin D Amplifies Type A Natriuretic Peptide Receptor Expression and Activity in Target Cells" *J Am Soc Nephrol*, 2005, 16:329-339.

Chin, L. et al. "Malignant melanoma: modem black plague and genetic black box" *Genes & Development*, 1998, 12(22):3467-3481.

Chiu, Y.L. et al. "RNAi in Human Cells: Basic Structural and Functional Features of Small Interfering RNA" *Molecular Cell*, Sep. 2002, 10(3):549-561.

Chopp, M. et al. "Spinal cord injury in rat: treatment with bone marrow stromal cell transplantation" *Neuroreport*, 2000, 11:3001-3005.

Clark, A.R. "Mechanisms of steroid action and resistance in inflammation: MAP kinase phosphatase 1: a novel mediator of biological effects of glucocorticoids" *Journal of Indocrinology*, 2003, 178:5-12.

Clemens, J.C. et al. "Use of double-stranded RNA interference in Drosophila cell lines to dissect signal transduction pathways" *PNAS*, 2000, 97:6499-6503.

Clusel, C. et al. "Ex vivo regulation of specific gene expression by nanomolar concentration of double-stranded dumbbell oligonucleotides" *Nucleic Acids Research* 1993, 21(15):3405-3411.

Collins, F.S. et al. "Generation and initial analysis of more than 15,000 full-length human and mouse cDNA sequences" *Proc Natl Acad Sci*, 2002:99:16899-16903.

Delporte, C. et al. "Discovery of a potent atrial natriuretic peptide antagonist for $ANP_A$ receptors in the human neuroblastoma NB-OK-1 cell line" *European Journal of Pharmacology*, 1992, 224:183-188.

Doczi, T.P. et al. "Atrial natriuretic peptide (ANP) attenuates brain oedema accompanying experimental subarachnoid haemorrhage" *Acta Neurochir (Wien)*, 1995, 132:87-91.

Dorn, G. et al. "siRNA relieves chronic neuropathic pain" *Nucleic Acids Research*, 2004, 32:e49.

Drewett, J.G. et al. "The family of guanylyl cyclase receptors and their ligands" *Endocrine Reviews*, 1994, 15(2):135-162.

El-Ayoubi, R. et al. "Urinary responses to acute moxonidine are inhibited by natriuretic peptide receptor agonist" *British Journal of Pharmacology*, 2005, 145:50-56.

Elbashir, S.M. et al. "RNA interference is mediated by 21- and 22-nucleotide RNAs" *Genes and Development*, 2001, 15:188-200.

Ernst, P. "Review article: the role of inflammation in the pathogenesis of gastric cancer" *Aliment Pharmacol Ther.*, 1999, pp. 13-18, vol. 13, No. 1.

Fattal, E. et al. "Biodegradable polyalkylcyanoacrylate nanoparticles for the delivery of oligonucleotides" *Journal of Controlled Release*, 1998, 53:137-143.

Filomeni, G. et al. "Pro-apoptotic Activity of Novel Isatin-Schiff Base Copper(II) Complexes Depends on Oxidative Stress Induction and Organelle-selective Damage" *Journal of Biological Chemistry*, 2007, 282(16):12010-12021.

Fiscus, R.R. "Involvement of Cyclic GMP and Protein Kinase G in the Regulation of Apoptosis and Survival in Neural Cells" *NeuroSignals*, 2002, 11:175-190.

Fonarow, G.C. et al. "Combining natriuretic peptides and necrosis markers in determining prognosis in heart failure" *Rev. Cardiovasc. Med.*, 2003, 4(suppl 4):S20-S28.

Forssmann, W.G. et al. "The renal urodilatin system: clinical implications" *Cardiovascular Research*, 2001, 51:450-462.

Fujiseki, Y. et al. "Natriuretic Peptide Receptors, NPR-A and NPR-B, in Cultured Rabbit Retinal Pigment Epithelium Cells" *Japanese Journal of Pharmacology*, 1999: 79:359-368.

Furst, R. et al. "Atrial natriuretic peptide induces mitogen-activated protein kinase phosphatase-1 in human endothelial cells via Rac1 and NAD(P)H oxidase/Nox2-activation" *Circ. Res.*, 2005, 96:43-53.

Gabellini, C. et al. "Involvement of RB gene family in tumor angiogenesis" *Oncogene*, 2006, 25:5326-5332.

Glover, V. et al. "Isatin: Identity with the Purified Endogenous Monamine Oxidase Inhibitor Tribulin" *Journal of Neurochemistry*, 1988, 51(2):656-659.

Gopalakrishnan, M. et al. "Stable expression and pharmacological properties of the human $a_7$ nicotinic acetylcholine receptor" *European Journal of Pharmacology: Molecular Pharmacology Section*, 1995, 290(3):237-246.

Gower, W.R. et al. "Regulation of atrial natriuretic peptide secretion by cholinergic and PACAP neurons of the gastric antrum" *Am. J. Physiol. Gastrointest. Liver Physiol.*, 2003, 284:G68-G74.

Greenberg, B.D. et al. "Nucleotide sequence of the gene encoding human atrial natriuretic factor precursor" *Nature*, 1984, 312(5995):656-658.

Greten, F.R. et al. "IKKβ links inflammation and tumorigenesis in a mouse model of colitis-associated cancer" Cell, 2004, 118:285-296.

Gura T. "Cancer Models: Systems for Identifying New Drugs are Often Faulty" *Science* 1997, 278(5340): 1041-1042, 1-5.

Halder, J. et al. "Focal Adhesion Kinase Targeting Using In vivo Short Interfering RNA Delivery in Neutral Liposomes for Ovarian Carcinoma Therapy" *Clinical Cancer Research*, 2006, 12:4916-4924.

Hamet, P. et al. "Aspects physiologiques et physiopathologiques du facteur natriuretique auriculaire" *Nephrologie*, 1987, 8:7-12, abstract.

Hammond, S.M. et al. "Argonaute2, a Link Between Genetic and Biochemical Analyses of RNAi" *Science*, Aug. 10, 2001, 293:1146-1150.

Harborth, J. et al. "Identification of essential genes in cultured mammalian cells using small interfering RNAs" *Journal of Cell Science*, 2001, 114:4457-4565.

Haseloff, J. et al. "Simple RNA enzymes with new and highly specific endoribonuclease activities" *Nature*, 1988, 334(6183):585-591.

He, Q. et al. "Inducible regulation of human brain natriuretic peptide promoter in transgenic mice" *Am. J. Physiol. Heart Circ. Physiol.*, 2001, 280:H368-H376.

Helene, C. et al. "Control of Gene Expression by Triple Helix-Forming Oligonucleotides: The Antigene Strategy" *Annals of the New York Academy of Sciences*, 1992, 660(1):27-36.

Hellerman, G. et al. "Mechanism of bronchoprotective effects of a novel natriuretic hormone peptide" *Journal of Allergy and Clinical Immunology*, 2004, 113:79-85.

Hirata, Y. "Heterologus Down-Regulation of Vascular Atrial Natriuretic Peptide Receptors by Phorbol Esters" *Biochemical and Biophysical Research Communications*, May 16, 1988, 152(3):1097-1103.

Ho, R.J.Y. et al. "Target-sensitive immunoliposomes: preparation and characterization" *Biochemistry*, 1986, 25:5500-5506.

Ho, R.J.Y. et al. "Interactions of Target-sensitive Immunoliposomes with Herpes Simplex Virus" *The Journal of Biological Chemistry*, 1987, 262(29):13979-13984.

Ho, R.J.Y. et al. "Target-sensitive immunoliposomes as an efficient drug carrier for antiviral activity" *The Journal of Biological Chemistry*, 1987, 262(29):13973-13978.

Howard, K.A. et al., "RNA Interference in Vivo and in Vitro Using a Chitosan/siRNA Nanoparticle System" *Molecular Therapy*, 2006, 14(4):476-484.

Hulks, G. et al. "Effect of atrial natriuretic factor on bronchomotor tone in the normal human airway" *Clin Sci* 1990, 79:51-55.

Hulks, G. et al. "Inhaled atrial natriuretic peptide and asthmatic airways" *Br. Med J*, 1992, 304:1156.

Hulks, G. et al. "High dose inhaled atrial natriuretic peptide is a bronchodilator in asthmatic subjects" *Eur Respir J.*, 1994, 7:1593-1597.

Hutvagner, G. et al. "RNAi: nature abhors a double-strand" *Current Opinion in Genetics & Development*, 2002, 12:225-232.

Igosheva, N. et al. "Isatin, an endogenous monamine oxidase inhibitor, triggers a dose- and time-dependent switch from apoptosis to necrosis in human neuroblastoma cells" *Neurochemistry International*, 2005, 47(3):216-224.

Inoue, J.I. et al. "NF-κB activation in development and progression of cancer" *Cancer Science*, 2007, 98:268-274.

Ishii, Y. et al. "Effects of atrial natriuretic peptide on Type II alveolar epithelial cells of the rat lung. Autoradiographic and morphometric studies" *J Anat.*, 1989, 166:85-95.

Izumi, T. et al. "Blockade of the natriuretic peptide receptor guanylyl cyclase-A inhibits NF-κB activation and alleviates myocardial ischemia/reperfusion injury" J Clin Invest 2001, 108:203-213.

Jacque, J.M. et al. "Modulation of HIV-1 replication by RNA interference" *Nature*, Jul. 25, 2002, 418(6896):435-438.

Jain, R.K. "Barriers to Drug Delivery in Solid Tumors" *Scientific American*, Jul. 1994, 58-65.

Jensen, K.T. et al. "A new, fast and reliable radioimmunoassay of brain natriuretic peptide in human plasma. Reference values in healthy subjects and in patients with different diseases" *Scand J Clin Lab Invest*, 1997, 57:529-540.

Jin, H. et al. "Novel analog of atrial natriuretic peptide selective for receptor-A produces increased diuresis and natriuresis in rats" *J. Clin. Invest.*, 1996, 98:969-976.

Kaneko, T. et al. "C-type natriuretic peptide (CNP) is the major natriuretic peptide in human cerebrospinal fluid" *Brain Res*, 1993, 612:104-109.

Kanwal, S. et al. "Intracellular fragments of the natriuretic peptide receptor-C (NPR-C) attenuate dopamine efflux" *Endocrinology*, 1999, 140(3):1118-1124.

Karin, M. "Mitogen activated protein kinases as targets for development of novel anti-inflammatory drugs" *Annals of the Rheumatic Diseases*, 2004, 63(Suppl. 2):ii62-ii64.

Katas, H. et al. "Development and characterisation of chitosan nanoparticles for siRNA delivery" *Journal of Controlled Release*, 2006, 115(2):216-225.

Kelly, R. et al. "Are natriuretic peptides clinically useful as markers of heart failure?" *Ann. Clin. Biochem.*, 2001, 38:94-102.

Khurana, M.L. et al. "Receptor-mediated stimulatory effect of atrial natriuretic factor, brain natriuretic peptide, and C-type natriuretic peptide on testosterone production in purified mouse Leydig cells: activation of cholesterol side-chain cleavage enzyme" *Endocrinology*, 1993, 133:2141-2149.

Kiemer, A. and Vollmar, A. "Autocrine regulation of inducible nitric-oxide synthase in macrophages by atrial natriuretic peptide" *J Biol Chem*, 1998, 273:13444-13451.

Kiemer, A. et al. "cGMP-mediated inhibition of TNF-a production by the atrial natriuretic peptide in murine macrophages" *J Immunol*, 2000, 165:175-181.

Kim, J.W. et al. "Effect of phosphorylation and S-S bond-induced dimerization on DNA binding and transcriptional activation by C/EBPβ" *Proc Natl Aced Sci USA*, 2007, 104:1913-1918.

Kisielow, M. et al. "Isoform-specific knockdown and expression of adaptor protein ShcA using small interfering RNA" *Biochem J.*, 2002, 363(1):1-5.

Klibanov, A.L. et al. "Amphipathic polyethyleneglycols effectively prolong the circulation time of liposomes" *FEBS Letters*, 1990, 268:235-237.

Knaapen, A.M. et al. "Inhaled particles and lung cancer. Part A: Mechanisms" *International Journal of Cancer*, 2004, 109:799-809.

Kojima, M. et al. "Cloning and sequence analysis of cDNA encoding a precursor for rat brain natriuretic peptide" *Biochem. Biophys. Res. Commun.*, 1989, 159(3):1420-1426.

Kong, X. et al. "Natriuretic Peptide Receptor A as a Novel Anticancer Agent" *Cancer Research*, Jan. 2008, 68(1):249-256.

"atrial natriuretic factor receptor A", MeSH results, accessed http://www.ncbi.nlm.nih.gov/mesh on Dec. 3, 2009, pp. 1-2.

Kumar, R. et al. "Expression of Guanylyl Cyclase-A/Atrial Natriuretic Peptide Receptor Blocks the Activation of Protein Kinase C in Vascular Smooth Muscle Cells: Role of cGMP and cGMP-Dependent Protein Kinase" *Hypertension*, 1997, 29:414-421.

Kumar, M. et al. "Intranasal IFN-γ gene transfer protects BALB/c mice against respiratory syncytial virus infection" *Vaccine*, 2000; 18:558-567.

Kumar, M et al. "Atrial natriuretic peptide gene transfer by means of intranasal administration attenuates airway reactivity in a mouse model of allergic sensitization" *J Allergy Clin Immunol.*, 2002, 110:879-882.

Kurihara, M. et al. "Lower number of atrial natriuretic peptide receptors in thymocytes and spleen cells of spontaneously hypertensive rats" *Biochemical and Biophysical Research Communications*, 1987, 149:1132-1140.

Lambert, G. et al. "Nanoparticulate systems for the delivery of antisense oligonucleotides" *Advanced Drug Delivery Reviews*, Mar. 2001, 47:99-112.

Landen, C.N. et al. "Intraperitoneal Delivery of Liposomal siRNA for Therapy of Advanced Ovarian Cancer" *Cancer Biology & Therapy*, 2006, 5(12):1708-1713.

Lee, N.S. et al. "Expression of small interfering RNAs targeted against HIV-1 rev transcripts in human cells" *Nature Biotechnology*, May 2002, 20:500-505.

Levin, E.R. et al. "Mechanisms of Disease: Natriuretic Peptides" *New England Journal of Medicine*, 1998, 339:321-328.

Li, Y. et al. "Intrastriatal transplantation of bone marrow nonhematopoietic cells improves functional recovery after stroke in adult mice" *Journal of Cerebral Blood Flow & Metabolism*, 2000, 20:1311-1319.

Li, Y. et al. "Human marrow stromal cell therapy for stroke in rat: Neurotrophins and functional recovery" *Neurology*, 2002, 59:514-523.

Liang, F. et al. "Sp1 dependence of natriuretic peptide receptor A gene transcription in rat aortic smooth muscle cells" *Endocrinology*, 1999, 140(4)1695-1701.

Lieberman, J. et al. "Interfering with disease: opportunities and roadblocks to harnessing RNA interference" *Trends in Molecular Medicine*, Sep. 2003, 9(9):397-403.

Lin, K-F. et al. "Human atrial natriuretic peptide gene delivery reduces blood pressure in hypertensive rats" *Hypertension*, 1995, 26:847-853.

Lin, K-F. et al. "Atrial natriuretic peptide gene delivery attenuates hypertension, cardiac hypertrophy, and renal injury in salt-sensitive rats" *Human Gene Therapy*, 1998, 9:1429-1438.

Liu, Y. et al."Discovery of Inhibitors that Elucidate the Role of UCH-L1 Activity in the H1299 Lung Cancer Cell Line" *Chemistry & Biology*, 2003, 10(9):837-846.

Liu, X. et al. "The influence of polymeric properties on chitosan/siRNA nanoparticle formulation and gene silencing" *Biomaterials*, 2007, 28:1280-1288.

Louzier, V. et al. "Adenovirus-mediated atrial natriuretic protein expression in the lung protects rats from hypoxia-induced pulmonary hypertension" *Hum Gene Ther*, 2001, 12:503-513.

Lu, D. et al. "Adult bone marrow stromal cells administered intravenously to rats after traumatic brain injury migrate into brain and improve neurological outcome" *NeuroReport*, 2001, 12:559-563.

Mahmood, a. et al. "Treatment of traumatic brain injury in female rats with intravenous administration of bone marrow stromal cells" *Neurosurgery*, 2001, 49:1196-1204.

Mahmood, A. et al. "Intracranial bone marrow transplantation after traumatic brain injury improving functional outcome in adult rats" *Journal of Neurosurgery*, 2001, 94:589-595.

Mahmood, A. et al. "Intracerebral transplantation of marrow stromal cells cultured with neurotrophic factors promotes functional recovery in adult rats subjected to traumatic brain injury" *J Neurotrauma*, 2002, 19:1609-1617.

Mailand, N. et al. "Deregulated human Cdc14a phosphatase disrupts centrosome separatin and chromosome segregation" *Nature Cell Biology*, 2002, 4(4):317-322.

Maisel, A.S. et al. "Cardiac natriuretic peptides: A proteomic window to cardiac function and clinical management" *Rev. Cardiovasc. Med.*, 2003, 4(suppl 4):S3-S12.

Martey, C.A. et al. "Cigarette smoke induces cyclooxygenase-2 and microsomal prostaglandin $E_2$ synthase in human lung fibroblasts: implications for lung inflammation and cancer" *Am J Physiol Lung Cell Mol Physiol*, 2004, 287:L981-991.

Martin, J. et al. "Modulation by biologic response modifiers of hepatitis C virus antigen-independent cytokine secretion in blood mononuclear cells" *Cytokine*, 1999, 11:267-273.

Massion, P.P. et al. "The molecular basis of lung cancer: molecular abnormalities and therapeutic implications" *Respiratory Research*, 2003, 4(1):12.1-12.15.

Matanic, D. et al. "Cytokines in patients with lung cancer" *Scand J Immunol*, 2003, 57:173-178.

Matsukawa, N. et al. "The natriuretic peptide clearance receptor locally modulates the physiological effects of the natriuretic peptide system" *Proc. Natl. Acad. Sci. USA*, 1999, 96:7403-7408.

Matsuse, H. et al. "Recurrent Respiratory Syncytial Virus Infections in Allergen-Sensitized Mice Lead to Persistent Airway Inflammation and Hyperresponsiveness" *The Journal of Immunology*, 2000, 164:6583-6592.

Matzke, M. et al. "RNA: Guiding Gene Silencing" *Science*, 2001, 293:1080-1083.

McCaffrey, A.P. et al. "Gene expression: RNA interference in adult mice" *Nature*, Jul. 2002, 418(6893):38-39.

Misono, K.S. "Natriuretic peptide receptor: Structure and signaling" *Molecular and Cellular Biochemistry*, 2002, 230:49-60.

Mohapatra, S.S. et al. "Natriuretic peptides and genesis of asthma: An emerging paradigm?" *Journal of Allergy and Clinical Immunology*, 2004, 114:520-526.

Mohapatra, S.S. et al. "Role of natriuretic peptide signaling in modulating asthma and inflammation" *Can J Physiol Pharmacol*, 2007, 85:754-759.

Morita, R. et al. "Atrial Natriuretic Peptide Polarizes Human Dendritic Cells Toward a Th2-Promoting Phenotype Through Its Receptor Guanylyl Cyclase-Coupled Receptor A1" *The Journal of Immunology*, 2003, 170:5869-5875.

Motohashi, S. et al. "Preserved IFN-a production of circulating Va24 NKT cells in primary lung cancer patients" *Int J Cancer*, 2002, 102:159-165.

Mueller, C. et al. "B-type natriuretic peptide (BNP): can it improve our management of patients with congestive heart failure?" *Swiss Med Wkly*, 2002, 132:618-622.

Nafee, N. et al. "Chitosan-coated PLGA nanoparticles for DNA/RNA delivery: effect of the formulation parameters on complexation and transfection of antisense oligonucleotides" *Nanomedicine: Nanotechnology, Biology, and Medicine*, 2007, 3(3):173-183.

Nakagawa, K. et al. "Plasma concentrations of atrial and brain natriuretic peptides in a case with hypertensive encephalopathy" *Neurol. Res.*, 2002, 24:627-630.

Nakao, N. et al. "Effect of atrial natriuretic peptide on ischemic brain edema: Changes in brain water and electrolytes" *Neurosurgery*, 1990, 27:39-44.

Naruse, S. et al. "Effects of atrial natriuretic peptide on brain oedema: The change of water, sodium, and potassium contents in the brain" *Acta Neurochir Suppl (Wien)*, 1990, 51:118-121.

Nazario, B. et al. "Atrial and brain natriuretic peptides stimulate the production and secretion of C-type natriuretic peptide from bovine aortic endothelial cells" *J. Clin. Invest.*, 1995, 95:1151-1157.

Needleman, P. et al. "Atriopeptin: A cardiac hormone intimately involved in fluid, electrolyte, and blood-pressure homeostasis" *N. Engl J Med*, 1986, 314:828-834.

Nocera, R. et al. "Novel strategies of neuroprotection against pathologic consequences of stroke in the aged brain" *Society for Neurosci. Abstracts*, 2001, 27(2):2302, Meeting date Nov. 10-15, 2001.

Novina, C.D. et al. "The RNAi revolution" *Nature*, 2004, 430:161-164.

Nuglozeh, E. et al. "Gene expression of natriuretic peptide receptors in rats with DOCA-salt hypertension" *Am J Physiol Cell Physiol*, 1997, 273:1427-1434.

Nykanen, A. et al. "ATP Requirements and small Interfering RNA Structure" *Cell*, Nov. 2001, 107:300-321.

Nyormoi, O. et al. "Transcriptional regulation of metastasis-related genes in human melanoma" *Clinical and Experimental Metastasis*, 2003, 20:251-263.

Ogata, A. et al. "Isatin, an endogenous MAO inhibitor, improves bradykinesia and dopamine levels in a rat model of Parkinson's disease induced by Japanese encephalitis virus" *Journal of the Neurological Sciences*, 2003, 206(1):79-83.

Ogawa, Y. et al. "Molecular cloning of the complementary DNA and gene that encode mouse brain natriuretic peptide and generation of transgenic mice that overexpress the brain natriuretic peptide gene" *J. Clin. Invest.*, 1994, 93(5):1911-1921.

Ohbayashi, H. et al, "Compared effects of natriuretic peptides on ovalbumin-induced asthmatic model" *Eur. J. Pharmac.*, 1998, 346:55-64.

Ohsaki, Y. et al. "Human small cell lung cancer cell lines express functional atrial natriuretic peptide receptors" *Cancer Res*, 1993, 53:3165-3171.

Ohsaki, Y. et al. "Human small cell lung cancer cells produce brain natriuretic peptide" *Oncology*, 1999, 56:155-159.

Ohyama, Y. et al. "Stable expression of natriuretic peptide receptors: Effects of HS-142-1, a non-peptide ANP antagonist" *Biochemical and Biophysical Research Communications*, 1992, 189:336-342.

Oka, D. et al. "Sesquiterpene lactone parthenolide suppresses tumor growth in a xenograft model of renal cell carcinoma by inhibiting the activation of NF-κB" *International Journal of Cancer*, 2007, 120:2576-2581.

Oliveira, A.M. et al. "Tumor Suppressor Genes in Breast Cancer: The Gatekeepers and the Caretakers" *American Society for Clinical Pathology*, 2005, 124:S16-S28.

Paddison, P.J. et al. "Short hairpin RNAs (shRNAs) induce sequence-specific silencing in mammalian cells" *Genes & Development*, 2002, 15:948-958.

Palaparti, A. et al. "Inhibition of atrial natriuretic peptide (ANP) C receptor expression by antisense oligodeoxynucleotides in A10 vascular smoth-muscle cells is associated with attenuation of ANP-C-receptor-mediated inhibition of adenylyl cyclase" *Biochem J*, 2000, 346:313-320.

Pandey, K.N. et al. "Natriuretic Peptide Receptor-A Negatively Regulates Mitogen-Activated Protein Kinase and Proliferation of Mesangial Cells: Role of cGMP-Dependent Protein Kinase" *Biochemical and Biophysical Research Communications*, 2000, 271:374-379.

Pandey, K.N. et al. "Functional domains and expression of truncated atrial natriuretic peptide receptor-A: The carboxyl-terminal regions direct the receptor internalization and sequestration in COS-7 cells" *Molecular Pharmacology*, 2000, 57:259-267.

Pandey, K.N. "Dynamics of internalization and sequestration of guanylyl cyclase/atrial natriuretic peptide receptor-A" *Canadian Journal of Physiology and Pharmacology*, 2001, 79(8):631-639.

Pandey, K.N. "Intracellular trafficking and metabolic turnover of ligand-bound guanylyl cyclase/atrial natriuretic peptide receptor-A into subcellular compartments" *Molecular and Cellular Biochemistry*, 2002, 230(1-2):61-72.

Pandey, K.N. et al. "Ligand-regulated Internalization, Trafficking, and Down-regulation of Guanylyl Cyclase/Atrial Natriuretic Peptide Receptor-A in Human Embryonic Kidney 293 Cells" *The Journal of Biological Chemistry*, 2002, 277:4618-4627.

Pandey, K.N. et al."Internalization and traffickign of guanylyl (guanylate) cyclase/natriuretic peptide receptor A is regulated by an acidic tyrosine-based cytoplasmic motif GDAY" *Biochemical Journal*, 2005, 388:103-113.

Paul, C.P. et al. "Effective expression of small interfering RNA in human cells" *Nature Biotechnology*, May 2002, 20:505-508.

Pedram, A. et al. "Natriuretic Peptides Inhibit G Protein Activation. Mediation Through Cross-Talk Between Cyclic GMP-Dependent Protein Kinase and Regulators of G Protein-Signaling Proteins" *J. Biol. Chem.*, 2000, 275:7365-7372.

Pikarsky, E. et al. "NF-κB functions as a tumour promoter in inflammation-associated cancer" Nature, 2004, 431: 461-466.

Plasterk, R.H.A., "RNA Silencing: The Genome's Immune System" *Science*, 2002, 296:1263-1265.

Popp, F.D. "Synthesis of potential antineoplastic agents. XX. Compounds related to the 3-o-nitrophenylhydrazone of isatin" *Journal of Medicinal Chemistry*, 1969, 12(1):182-184.

Porter, J.G. et al. "Cloning of a cDNA encoding porcine brain natriuretic peptide" *J. Biol. Chem.*, 1989, 264(12):6689-6692.

Prins, B.A. et al. "Atrial natriuretic peptide inhibits mitogen-activated protein kinase through the clearance receptor" *J. Biol. Chem.*, 1996, 271(24):14156-14162.

Reich, S.J. et al. "Small interfering RNA (siRNA) targeting *VEGF* effectively inhibits ocular neovascularization in a mouse model" *Molecular Vision*, 2003, 9:210-216.

Rouleau, N. et al. "Development of a Non-radioactive Homogenous HTS Platform to Measure the Activity of Guanylate Cyclase", Poster #P10144, Presented at 10th Annual SBS Conference and Exhibition, Orlando, FL, Sep. 11-15, 1004, Perkinelmer Biosignal Inc., Canada, 2004.

Roy, R.N. et al. "Organization of the gene for iso-rANP, a rat B-type natriuretic peptide" *Biochem. Biophys. Res. Commun.*, 1990, 171(1):416-423.

Roy, K. et al. "Oral gene delivery with chitosan? DNA nanoparticles generates immunologic protection in a murine model of peanut allergy" *Nature Medicine*, 1999, 5(4):387-391.

Rutherford, R.A.D. et al. "Identification of renal natriuretic peptide receptor subpopulations by use of the non-peptide antagonist, HS-142-1" *British Journal of Pharmacology*, 1994, 113(3):931-939.

Saccani, A. et al. "p50 Nuclear Factor-κB Overexpression in Tumor-Associated Macrophages Inhibits M1 Inflammatory Responses and Antitumor Resistance" *Cancer Research*, Dec. 2006, 66(23):11432-11440.

Sanchez-Ramos, J.R. "Neural cells derived from adult bone marrow and umbilical cord blood" *J. Neurosci. Res.*, 2002, 69:880-893.

Scadden, A.D.J. "RNAi is antagonized by A→I hyper-editing" *EMBO Reports*, 2001, 11(2):1107-1111.

Scherr, M. etal. "Inhibition of GM-CSF Receptor Function by Stable RNA Interference in a NOD/SCID Mouse Hematopoietic Stem Cell Transplantation Model" *Oligonucleotides*, Oct. 2003, 13(5): 353-363.

Schipper, N.G.M. et al. "Chitosans as Absorption Enhancers for Poorly Absorbable Drugs. 1: Influence of Molecular Weight and Degree of Acetylation on Drug Transport Across Human Intestinal Epithelial (Caco-2) Cells" *Pharmaceutical Research*, 1996, 13(11):1686-1692.

Schmidt, D. et al. "Critical role for NF-κB-induced JunB in VEGF regulation and tumor angiogenesis" *The EMBO Journal*, 2007, 26:710-729.

Schwartz, A.G. et al."The molecular epidemiology of lung cancer" *Carcinogenesis*, 2007, 28:507-518.

Seidman, C.E. et al. "The structure of rat preproatrial natriuretic factor as defined by a complementary DNA clone" *Science*, 1984, 225:324-326.

Seidman, C. et al. "Nucleotide sequences of the human and mouse atrial natriuretic factor genes" Science, 1984, 226:1206-1209.

Seilhamer, J.J. et al. "Human and canine gene homologs of porcine brain natriuretic peptide" *Biochem. Biophys. Res. Commun.*, 1989, 165(2):650-658.

Sekiguchi, T. et al. "Molecular cloning of natriuretic peptide receptor A from Bullfrog (*Rana catesbeiana*) brain and its functional expression" *Gene*, 2001, 273(2):141-319.

Sharma, G.D. et al. "Expression of atrial natriuretic peptide receptor-A antagonizes the mitogen-activated protein kinases (Erk2 and P38MAPK) in cultured human vascular smooth muscle cells" *Molecular and Cellular Biochemistry*, 2002, 233(1-2):165-173.

Sharp, P.A. "RNAi and double-strand RNA" *Genes & Dev.*, 1999, 13:139-141.

Sharp, P.A. "RNA interference—2001" *Genes & Development*, 2001, 15:485-490.

Shi, S-J. et al. "Natriuretic peptide receptor A mediates renal sodium excretory responses to blood volume expansion" *Am. J. Physiol. Renal Physiol.*, 2003, 285:F694-F702.

Shimizu, K. et al. "Ectopic atrial natriuretic peptide production in small cell lung cancer with the syndrome of inappropriate antidiuretic hormone secretion" Cancer, 1991, 68:2284-2288.

Silberbach, M. and Roberts, Jr., C. "Natriuretic peptide signalling molecular and cellular pathways to growth regulation" Cell Signalling, 2001, 13:221-231.

Simkins, J. "Nesiritide (Natrecor®) for Decompensated CHF" in The University of Montana's School of Pharmacy and Allied Health Sciences Drug Information Service, Apr. 2002, vol. 6 No. 4.

Song, S. et al. "Nerve growth factor and retinoic acid induce development of neuronal cells from bone marrow stromal cells of both young and old mice" *Society for Neurosci. Abstracts*, 2001, 27(1):940, Meeting date Nov. 10-15, 2001.

Song, S. et al. "Expression of brain natriuretic peptide by human bone marrow stromal cells" *Society for Neurosci. Abstracts*, 2002, Abstract No. 824.3, Meeting date Nov. 2-7, 2002.

Song, S. et al. "Preparation of Neural Progenitors from Bone Marrow and Umbilical Cord Blood" in Protocols for Neural Stem Cell Methods, Zigova, T. et al., Eds., 2002, pp. 79-88.

Song, E. et al. "RNA interference targeting Fas protects mice from fulminant hepatitis" *Nature Medicine*, 2003, 9(3):347-351.

Song, S. et al. "Expression of brain natriuretic peptide by human bone marrow stromal cells" *Experimental Neurology*, 2004, 185:191-197.

Soutschek, J. et al. "Therapeutic silencing of an endogenous gene by systemic administration of modified siRNAs" *Nature*, Nov. 2004, 432:173-178.

Steinhelper, M.E. "Structure, expression, and genomic mapping of the mouse natriuretic peptide type-B gene" *Circ. Res.*, 1993, 72(5):984-992.

Sudoh, T. et al. "Brain natriuretic peptide-32: N-terminal six amino acid extended form of brain natriuretic peptide identified in porcine brain" *Biochem Biophys Res Commun*, 1988, 155:726-732.

Suenobu, N. et al. "Natriuretic peptides and nitric oxide induce endothelial apoptosis via a cGMP-dependent mechanism" *Arterioscler Thromb Vasc Biol.*, 1999, 19:140-146.

Sumpter, W.C. "The Chemistry of Isatin" *Chemical Reviews*, 1944, 34(3):393-434.

Suric-Lambic, L. et al. "Vasoactive natriuretic peptides and kidney" *Facta Universitatis: Medicine and Biology*, 1998, 5(1):6-11.

Tolentino, M.J. et al. "Intravitreal Injection of Vascular Endothelial Growth Factor Small Interfering RNA Inhibits Growth and Leakage in a Nonhuman Primate, Laser-Induced Model of Choroidal Neovascularization" *Retina*, 2004, 24:132-138.

Tremblay, J. et al. "Biochemistry and physiology of the natriuretic peptide receptor guanylyl cyclases" *Molecular and Cellular Biochemistry*, 2002, 230:31-47.

True, D. et al. "Comparison of Kinase Assay Technologies for High Throughput Screening" poster presented at Society for Biomolecular Screening (SBS), 8th Annual Conference, Sep. 22-26, 2002.

Tunny, T.J. et al. "Association of Restriction Fragment Length Polymorphism at the Atrial Natriuretic Peptide Gene Locus with Aldosterone Responsiveness to Angiotensin in Aldosterone-Producing Adenoma" *Biochemical and Biophysical Research Communications*, 1994, 204:1312-1317.

Tuschl, T. "RNA Interference and Small Interfering RNAs" *Chembiochem*, 2001, 2:239-245.

Tuschl, T. "Expanding small RNA interference" *Nature Biotechnology*, 2002, 20:446-448.

Vellaichamy, E. et al. "Reduced cGMP signaling activates NF-κB in hypertrophied hearts of mice lacking natriuretic peptide receptor-A" *Biochemical and Biophysical Research Communications*, 2005, 327:106-111.

Verma, I.M. et al. "Gene Therapy—promises, problems and prospects" *Nature*, 1997, 389:239-242.

Vesely, D.L. et al. "Atrial natriuretic peptides negatively and positively modulate circulating endothelin in humans" *Metabolism*, 1996, 45:315-319.

Vesely, D.L. et al. "Vessel dilator, long acting natriuretic peptide, and kaliuretic peptide increase circulating prostaglandin $E_2$" *Life Sciences*, 2000, 66:095-913.

Vesely, D.L. "Atrial natriuretic peptides in pathophysiological diseases" Cardiovascular Res., 2001, 51:647-658.

Vesely, D.L. et al. "Atrial Natriuretic Hormone, Vessel Dilator, Long-Acting Natriuretic Hormone, and Kaliuretic Hormone Decrease the Circulating Concentrations of CRH, Corticotropin, and Cortisol" *J Clin Endocrinol Metab*, 2001, 86:4244-4249.

Vesely, D.L. et al. "Atrial Natriuretic Hormone, Vessel Dilator, Long Acting Natriuretic Hormone, and Kaliuretic Hormone Decrease Circulating Prolactin Concentrations" *Horm Metab Res*, 2002, 34:245-249.

Vesely, D.L. "Atrial Natriuretic Peptide Prohormone Gene Expression: Hormones and Diseases That Upregulate its Expression" *IUBMB Life*, 2002, 53(3):153-159.

Vesely, B.A. at al. "Four peptide hormones decrease the number of human breast adenocarcinoma cells" *European Journal of Clinical Investigation*, 2005, 35:60-69.

Vesely, B.A. et al. "Four peptides decrease the number of human pancreatic adenocarcinoma cells" *Eur. J. Clin. Invest.*, 2003, 33:998-1005.

Vesely, B.A. et al. "Four Cardiac Hormones Cause Cell Death of Melanoma Cells and Inhibit Their DNA Synthesis" *Am J Med Sci*, 2007, 334(5):342-349.

Vilimas, T. et al. "Targeting the NF-κB signaling pathway in Notch1-induced T-cell leukemia" *Nature Medicine*, 2007, 13:70-77.

Vine, K.L. et al. "In vitro cytotoxicity evaluation of some substituted isatin derivatives" *Bioorganic & Medicinal Chemistry*, 2007, 15(2):931-938.

Vlasuk, G.P. et al. "Structure and analysis of the bovine atrial natriuretic peptide precursor gene" *Biochem. Biophys. Res. Commun.*, 1986, 136(1):396-403.

Wang, W. et al. "AlbuBNP, a recombinant B-type natriuretic peptide and human serum albumin fusion hormone, as a long-term therapy of congestive heart failure" *Pharm. Res.*, 2004, 21(11):2105-2111.

Wang, X. et al. "Modulation of lung inflammation by vessel dilator in a mouse model of allergic asthma" *Respiratory Research*, Jul. 2009, 10(66):1-8.

Wang, X. et al. "Prevention of airway inflammation with topical cream containing imiquimod and small interfering RNA for natriuretic peptide receptor" *Genetic Vaccines and Therapy*, Feb. 2008, 6(7):1-9.

Winquist, R. et al. "Atrial natriuretic factor elicits an endothelium-independent relaxation and activates particulate guanylate cyclase in vascular smooth muscle" *Proc. Natl. Acad. Sci. USA*, 1984, 81:7661-7664.

Woodle, M.C. et al. "Sterically stabilized liposomes" *Biochimica et Biophysica Acta: Reviews on Biomembranes*, 1992, 1113:171-199.

Xia, H. et al. "siRNa-mediated gene silencing in vitro and in vivo" *Nature Biotechnology*, Oct. 2002, 20(10):1006-1010.

Yu, J.Y. et al. "RNA interference by expression of short-interfering RNAs and hairpin RNAs in mammalian cells" *PNAS USA*, Apr. 2002, 99(9):6047-6052.

Yuhas, J.M. et al. "Specific and Nonspecific Stimulation of Resistance to the Growth and Metastasis of the Line 1 Lung Carcinoma" *Cancer Research*, 1975, 35:242-244.

Zamore, P.D. "Ancient Pathways Programmed by Small RNAs" *Science*, 2002, 296(5571):1265-1269.

Zamore, P.D. "RNA interference: listening to the sound of silence" *Nature Structural Biology*, Sep. 2001, 8(9):746-750.

Zamore, P.D. et al. "RNAi: Double-Stranded RNA Directs the ATP-Dependent Cleavage of mRNA at 21-23 Nucleotide Intervals" *Cell*, Mar. 31, 2000, 101(1):25-33.

Zhang, X. et al. "Small Interfering RNA Targeting Heme Oxygenase-1 Enhances Ischemia-Reperfusion-induced Lung Apoptosis" *The Journal of Biological Chemistry*, Mar. 2004, 279(11):10677-10684.

Zeng, Y. et al. "Both Natural and Designed Micro RNAs Can Inhibit the Expression of Cognate mRNAs When Expressed in Human Cells" *Molecular Cell*, Jun. 2002, 9:1327-1333.

Zimmerman, T.S. et al. "RNAi-mediated gene silencing in non-human primates" *Nature*, May 2006, 441:111-114.

Zivin, R.A. et al. "Molecular cloning and characterization of DNA sequences encoding rat and human atrial natriuretic factors" *Proc. Natl. Acad. Sci. USA*, 1984, 81(20):6325-6329.

Vesely, D.L. et al. "Four Cardiac Hormones Eliminate up to Two-Thirds of Human Breast Cancers in Athymic Mice" *In Vivo*, 2007, 21:973-978.

Eichelbaum, E.J. et al. "Cardiac and kidney hormones cure up to 86% of human small-cell lung cancers in mice" *Eur J Clin Invest*, 2008, 38(8):562-570.

Vesely, D.L. et al. "Elimination of Up to 80% of Human Pancreatic Adenocarcinomas in Athymic Mice by Cardiac Hormones" *In Vivo*, 2007, 21:445-452.

Lenz, A. et al. "Cardiac Hormones Eliminate some Human Squamous Lung Carcinomas in Athymic Mice" *European Journal of Clinical Investigation*, 2010 in press, p. 1-13.

\* cited by examiner

SEQUENCE LISTING

```
<160> NUMBER OF SEQ ID NOS: 6

<210> SEQ ID NO 1
<211> LENGTH: 72
<212> TYPE: DNA
<213> ORGANISM: Artificial Sequence
<220> FEATURE:
<223> OTHER INFORMATION: siNPRA1

<400> SEQUENCE: 1
catatggggc ccgggcgctg ctgctgctac cctcgaaatg gtagcagcag cagcgcsctt      60
gaattcccat gg                                                          72

<210> SEQ ID NO 2
<211> LENGTH: 72
<212> TYPE: DNA
<213> ORGANISM: Artificial Sequence
<220> FEATURE:
<223> OTHER INFORMATION: siNPRA2

<400> SEQUENCE: 2
catatggggc ccgcggccac gcgagcgacc tctcgaaata ggtcgctcgc gtggccgctt      60
gaattcccat gg                                                          72

<210> SEQ ID NO 3
<211> LENGTH: 72
```

```
<212> TYPE: DNA
<213> ORGANISM: Artificial Sequence
<220> FEATURE:
<223> OTHER INFORMATION: siNPRA3

<400> SEQUENCE: 3
catatggggc cggctcggc cggacttgct gctcgaaatc agcaagtccg gccgagcctt    60
gaattcccat gg                                                      72

<210> SEQ ID NO 4
<211> LENGTH: 15810
<212> TYPE: DNA
<213> ORGANISM: Homo sapiens

<400> SEQUENCE: 4
ggatcccaaa ccagcacacc tttccctctt cccccgagga gaccaggtag gaggcgaggg    60
aaaaggtggg gcgcaagtgg gccccggttg cttccacaca cccctccgt tcagccgtcc   120 tttccatccc ggcgagggcg caccttcaga gggtcctgtc ctccaaagag gtaggcgtgg   180
ggcggccgag accggggaag atggtccacg gggaagcgcg cgggctgggc ggcggggagg   240
aaggagtcta tgatcctgga ttggctcttc tgtcactgag tctgggaggg gaagcggctg   300
ggagggaggg ttcggagctt ggctcgggtc ctccacggtt ccctccggat agccggagac   360
ttgggccggc cggacgcccc ttctggcaca ctccctgggg caggcgctca cgcacgctac   420
aaacacacac tcctctttcc tccctcgcgc gccctctctc atccttcttc acgaagcgct   480
cactcgcacc ctttctctct ctctctctct ctctaacacg cacgcacact cccagttgtt   540
cacactcggg tcctctccag cccgacgttc tcctggcacc cacctgctcc gcggcgccct   600
gcacgccccc ctcggtcgcg ccccttgcgc tctcggccca gaccgtcgca gctacagggg   660
gcctcgagcc ccggggtgag cgtccccgtc ccgctcctgc tccttcccat agggacgcgc   720
ctgatgcctg gaccggccg ctgagcccaa ggggaccgag gaggccatgg taggagcgct   780
cgcctgctgc ggtgcccgct gaggccatgc cggggccccg gcgccccgct ggctcccgcc   840
tgcgcctgct cctgctcctg ctgctgccgc gctgctgct gctgctccgg ggcagccacg   900
cgggcaacct gacggtagcc gtggtactgc cgctggccaa tacctcgtac ccctggtcgt   960
gggcgcgcgt gggacccgcc gtggagctgg ccctggccca ggtgaaggcg cgccccgact  1020
tgctgccggg ctggacggtc cgcacggtgc tgggcagcag cgaaaacgcg ctgggcgtct  1080
gctccgacac cgcagcgccc ctggccgcgg tggacctcaa gtgggagcac aaccccgctg  1140
tgttcctggg ccccggctgc gtgtacgccg ccgccccagt ggggcgcttc accgcgcact  1200
ggcgggtccc gctgctgacc gccggcgccc cggcgctggg cttcggtgtc aaggacgagt  1260
atgcgctgac cacccgcgcg gggcccagct acgccaagct gggggacttc gtggcggcgc  1320
tgcaccgacg gctgggctgg gagcgccaag cgctcatgct ctacgcctac cggccgggtg  1380
acgaagagca ctgcttcttc ctcgtggagg ggctgttcat gcgggtccgc gaccgcctca  1440
atattacggt ggaccacctg gagttcgccg aggacgacct cagccactac accaggctgc  1500
tgcggaccat gccgcgcaaa ggccgaggtg agacgctggc acacccgtc ccgccgctta  1560 gccgcagggc ctcccctctg acctgccgga ggcatcggga cttttctctct catctggggg  1620 cactcttctt tctcctcgcc gttcttcatt ctactttcag ctccctggcc cttttctacag  1680 ctgagtttct atttccctct cttcttccgc cacccccacc acgtctctat cctctcatct  1740
ccccgacccc cactcattcc ctcccaccct agcacagctc ggttccggtc ccttttttccc  1800 tcccacattt tctctcttcc ctatagcctt ctcccttctt tcatcctctc ctctcatggc  1860
```

```
gcctcatccc ctctcttctc cccctccctc tccctcctct ctccctcctg gccccatcct    1920
tctccacctt cagctccact atccccctct ccctacccgt tccttcctcc cttccgcctc    1980
cccctccctc ctcccgccca ccgccccgca ccgcccgtt ccacccttcg actttctcct     2040
gctgtggcct aggctgagcc gggagttacc acttaactct cactgggtct ctcctgcacc    2100
ctatctctaa acttcctccc ttgggtgccc cagctttcct actcctgtct ctcccgcagt    2160
acctaggctt ctctctctga ctctccgtct ttctccagtt atctacatct gcagctcccc    2220
tgatgccttc agaaccctca tgctcctggc cctggaagct ggcttgtgtg gggaggacta    2280
cgttttcttc cacctggata tctttgggca aagcctgcaa ggtggacagg gccctgctcc    2340
ccgcaggccc tgggagagag gggatgggca ggatgtcagt gcccgccagg cctttcaggt    2400
gagtacctag gtttgaagcc caggctgtct cagcttgtgg cacatcattt ctgggcactg    2460
tgtccctcag catctgaaag aattccagaa aagaggtttt tgtctgtttg tttctttatg    2520
cactcctggt aactcacaga acagaaaaga ggttggtgat gctcactggg aattaggcaa    2580
tgaagggcag gggactgccc aggggcgctt cgccaccagc aggctaaaaa gataagaaaa    2640
tgggcttgag gcgggaggag gataaagtcc cacagcctgg acaggacttg gagaaggcat    2700
cccattggat cccctgcttt ggaatgggca tcacttcatg cagggcatag ggtccagttt    2760
gaccttgagc taagcagaga cgcagctctg ggaggtgggc tcccaactgt tggggccca    2820 cagtactagg gaatagtcag ctcccaactc tctgctctcc actgacccct ttctcaggct    2880
gccaaaatca ttacatataa agacccagat aatcccgagt acttggaatt cctgaagcag    2940
ttaaaacacc tggcctatga gcagttcaac ttcaccatgg aggatggcct ggtaagaagg    3000
ggtcccggga ccctccagcg tggacctcca gcccccactc catgaccctc tgccagcctc    3060
catccttccc tattcccagt tctccccttc cttccctccc ttccattgt tccatgtttc     3120 tcgtgatgat ggaggaggac actggcaagt tcagcctctg aaactcaggt catcatcagt    3180
aatatggaga cgatacatcc tgccctgtct acctagtagg attcaggaag tgatgctaat    3240
ccaaaggcat cgtttaaata gtaaaatctc cctgtgatat aggggtgtta ttttctccca    3300
tcctcttcca aaatcccagt gcctcttgtt cccttcccca cagctcccac ctccatgccc    3360
ttcatatgcc caccccagcc gacctctgtt gccctaca ggtgaacacc atcccagcat      3420
ccttccacga cgggctcctg ctctatatcc aggcagtgac ggagactctg gcacatgggg    3480
gaactgttac tgatggggag aacatcactc agcggatgtg gaaccgaagc tttcaaggtc    3540
agggcctgga ggtggctgga atgggctgcc ttggggatg aatcccaggt gcccagtgtc     3600
aagccatgag aagcctattg tcctgcagca gttacctatg cacaccagcc tttcctcca     3660 cagctttttt caggcccatc cctcagaagt cctacaaagt gtccaatctc aatcatccct    3720
gctgggcact gagttctttt acctttcttt ttctttttc ttttttttt gagatggagt       3780 ctcgctctgt ccccaagact ggagtgtggt ggtgcaatct cggctcactt caacctccgc    3840
ctcccaggtt caagcaattc tcctgcctca gcctcctgag tagctgggat tacaggtgcc    3900
ctccaccaac acttggctaa ttttttgtat tttttttagt agagacaggg tttcaccacg    3960
ttggtcaggc tggtcttgaa ctcctgacgt caggtgatct gcccgcctca gcctcccaaa    4020
gtgctgggat tacaagcatg agccacagtg cccggccgtt ttaccattta ctatcattct    4080
gtatacatgt atgtttggaa ggcaaggcaa aaagattag aggatgaaga gatgaagtgg     4140
ggcacccctg aacttctatt ctctcaaaca tagtcatctt cccccatgtc ctcaggtgtg    4200
acaggatacc tgaaaattga tagcagtggc gatcgggaaa cagacttctc cctctgggat    4260
```

```
atggatcccg agaatggtgc cttcagggta agtttgtgca cccagaagac agtgccaatt    4320
ccaaatgaca tctcaccctc ctacttcccc cccacagccc tgccagggca cctgtttatc    4380
ctgtagccat tccaccatgc ctggacactt acaagagccc tggataaaac agacccagct    4440
ccagtctggg gaagccacca gaatgatagg gactcacagg catcacactt ggggagcccc    4500
atgcctgagg agggagcaca agcctgccct cggggagctc cgaagggagg caggcaggac    4560
cgcctcccag cagagacagg gctgtgaaag atgcacatta cacagctctg caagcgagca    4620
gggacaggaa ggcgctgagg ccaatggcca aagggacag gtcatccaga gaaggcctcc    4680
tggaagacgg gcacatggac tgggcctgcg aatgtaggct aaggtgaaca ttaccttctc    4740
ctgttttcta ccaagaaaat aagtagagaa aaatcaatgc ttggttggta cttcaaccaa    4800
gattataaac tccctgagtg tagagatcgg gttctaaatg gagttttctt tataaacccc    4860
ttgatagttt tcaggtgttt ccacttgagt actatgtgtg tggtatgagg tcctgtgtcc    4920
agttgcagtg gggacttggt aagcaggtga caacccagat atatatgtag gctctagaag    4980
cagagctggg gtaggtggga ggtgagactg ctgcactcac agcatgcctt ccccgcaggc    5040
cctggcctag ccaccactcc tgctctccct taggttgtac tgaactacaa tgggacttcc    5100
caagagctgg tggctgtgtc ggggcgcaaa ctgaactggc ccctgggta ccctcctcct    5160 gacatcccca aatgtggctt tgacaacgaa gacccagcat gcaaccaagg tgactgcccc    5220
ttgccttcca ggcctccatc ccagagatgc tgcatccttc ccctaagcac agtcgagtag    5280
gtgctcctgt cccatgctga gggctttctg gagaatgact cctgcctttt tcttcccttc    5340
atccatcatc ccagttcact gatggactat tagaaagttc ttcctcctgc tgtctaaccc    5400
aaatctctct tgctgcaata tggactctct cctgcagatc acctttccac cctggaggtg    5460
ctggctttgg tgggcagcct ctccttgctc ggcattctga ttgtctcctt cttcatatac    5520
aggtgagctg tgatgtgggg ggttgagtga ggctggggga cccggagaac caagagcaga    5580
ggaggcggtg gggacccaga gggaagaggg caggggtgaa ggggcagcag gggaaaacca    5640
agggagatga ggaagaaagg aggcttaaaa gccagaggag aaagaaagag aagggaatgg    5700
cagggcgagg ggaggagaca aggataggaa tggccaagga gagtcagaaa gatccaagaa    5760
gcagagaagt tgatgggtga catcataggg gcgtggactg gttttccttg ctactcttgc    5820
aggccagata ggaagcaact ttctgaacct ttgcaatcat gcccatgtta gctgaggagg    5880
gtgagccctg tgtgtgcca ggtgcccaac ctagaatgga gaagggagct gaatgagcct    5940
tgttcctgcc gtccagtgga ggctaaaatg aagtacagga ggagttaatg atatacaaaa    6000
gcaaggaggg aggggagaaa aatcactgct ggttgagcat ataatgtgtg ccaggcactt    6060
ccacgtacac tatttctttc tttctttttt ttttttttt ttttttttg agacggagtc    6120 tcgctctgtt gccagactgg agtgcagtgg catgatctag gctcactgca acctccgcct    6180
cccagtttca agcaattctc ctgcctcagc ctcccatgta gctgggacta caggcacatg    6240
ccaccacgct cagctaattt ttgtatttt agtagagaca gggtttcacc atgttggcca    6300
ggatggtctc gatctcttga cctcatgatc cacccacctt ggcctcccaa agtgctggga    6360
ttacaggcat gagccactgt gcctggcctc atgttcacta tttcttttca ttccttataat    6420 agttaagaat gaaatagata ttgcggcctc attcccaagt aaggacattg aggtgattcc    6480
cccaaggtcc ccagtaaggc agaatttccc ccagccatcc tgattctcag tccagaggat    6540
agaattcccc ctccatctct gagtgcatgg tgtggtccca cggctctgag gaggggctgc    6600
tgagcaccct gccctgggtc agcggctcag ccacaggctc agatgcagcc ttcgtatccc    6660
```

```
aggaagatgc agctggagaa ggaactggcc tcggagctgt ggcgggtgcg ctggaggac    6720 gttgagccca gtagccttga gaggcacctg cggagtgcag gcagccggct gaccctgagc    6780
ggggtaagaa cgctggtgtt tgtgttgggg ggcaataaag gagaggtggg tacaaggggc    6840
agtgcctgag ggataggtaa gggagcagga ttctagtccc agctctgctt tcacttgctg    6900
tgtgaccttg agcgactcat agtccctctc cgagactgtc tcagatgatg attacagcag    6960
cagagcctcc ctcacagggc tcttttaaag gtcagaggag atagtacctg tgaaaacact    7020
ttaaaaaaaa aaaagtaaa tgaggaggaa attttatgat gtggaacata agcagggtg     7080 ggccaggcac agtggctcac atctgcaatc ccagcacttt gggagaccga ggcaggagga    7140
ttgcttgtgc ctgggagttc aagaccagcc tgggcaacag agcaagacat cgtctctaca    7200
aagaatacaa agattagcag ggcatggtgg cgcatacctg tagtcccagc tactctggag    7260
gctgaggtga aaggatcatc tgagcccagg agtctgaggc ggcagtgacc taggatagca    7320
ccactgcact ccagcctgga tgacacaatg atactacatc tcaaaaaaaa acccaacaac    7380
aaaaaggaag ggtgacacaa agataaggca ggataaggca gggaaataaa gaccagagca    7440
caagcaatca ggatgcagac tgggcccacc ggctgaccat tcctcctgct ctccctcctt    7500
tcagagaggc tccaattacg gctccctgct aaccacagag ggccagttcc aagtctttgc    7560
caagacagca tattataagg tgggcctggg gaaagatcac tgggccttgg gactggggca    7620
ggagtgtact ctgatggagg actggtgggg ggttctgagg gaaggagtaa gctggtgggg    7680
agcagcagat gggggccctg ggggtgggct attgggaaca agtgagggtc ctgagggcag    7740
ggatgggctg tcgggagcag ctggaattcc caggacatgg gaccatgctc ttcacagtga    7800
cagtctccat tccatgccca gggcaacctc gtggctgtga acgtgtgaa ccgtaaacgc     7860 attgagctga cacgaaaagt cctgtttgaa ctgaagcatg taatgtgggg agtgaggcag    7920
tggcatggag aaggggccct cggggacgca agggagactg gccaacagaa ctagttatgg    7980
agggacctca gggtacccca agaaagggc agggactgga gccctggatg accttcatct     8040
tgtggtggag tgggggtatc ctaagtagga gaagagacca ctgagataac ctggaggaat    8100
cttgaggggc catatgtgat gtccctgggg gagagagggc ttaggatgcc agagggagta    8160
ggagcagatt ctggggaggg tgggctaaag gacatgggtg ggaatcacca gggaagatct    8220
tagtgatggt tgcagaaagt gaataaggag ttaagaagag tgagggtccc tgaagctagt    8280
gagcagcttg gtgaggagcg aggtctctgt caagctcctg atgctggtcc cacttgcaga    8340
tgcgggatgt gcagaatgaa cacctgacca ggtttgtggg agcctgcacc gaccccccca    8400
atatctgcat cctcacagag tactgtcccc gtgggagcct gcaggtgagg gggacaaggg    8460
gtgtcaagaa acctgggttc tagccctggc tctgcccctg actggccata agaccccagg    8520
catgcctcgc cctctttctg acctttctgg ccccatctgt aaaaatggga gttgggaag    8580 ggcagtggca ctagagtcaa tccaaagttt tgtcctgttc taccagttca catcagtagg    8640
accctgcacc ctcctccaac tcccaggggg atctgcaggg gattggtctt gactcttatt    8700
gccccagcag gacattctgg agaatgagag catcaccctg gactggatgt tccggtactc    8760
actcaccaat gacatcgtca aggtatgccc ctaagcacct attggatgtg tagagcaggg    8820
gccaggcatg cttctcctgg ccacgggtgt aggtcccact cctggccaat acctctgccc    8880
actcacattt ccagggcatg ctgtttctac acaatggggc tatctgttcc catgggaacc    8940
tcaagtcatc caactgcgtg gtagatgggc gctttgtgct caagatcacc gactatgggc    9000
tggagagctt cagggacctg gacccagagc aaggacacac cgtttatgcc agtgagcctt    9060
```

```
gactcttgaa cctaacacct gcccccagca ccacccagta gggagactga tgcaaggcct      9120
ctgatgggct tgggcatgct tgtcctgact ccagcctcaa ttcattcacc catgaaaaag      9180
ggaaggccag acgaagtggt ttctaaggcc tcctctagct ctaacactct gtgatgcatc      9240
cagatcagtt tcggccacac ccttgtttcc ccctcacccc ttagctttgg gctccctcac      9300
tcggtgacta ccgacctctg acccacagaa aagctgtgga cggcccctga gctcctgcga      9360
atggcttcac cccctgtgcg gggctcccag gctggtgacg tatacagctt tgggatcatc      9420
cttcaggaga ttgccctgag gagtggggtc ttccacgtgg aaggtttgga cctgagcccc      9480
aaaggtgaga ggagcacacc ttccttaaac ccagccacag tctcaacgaa ccccagcccc      9540
agggagaggg tcccctggca gcaccaccac accttccttc tgtaatgggg ttcagtcacc      9600 acccttgac ccattgctgc cagtgaccag tcccccgccc ccatgccttg gtcttggact       9660
tcccctgcca tctcagctgg ttgcccagt ctctcactag gcccttggcc agccccaccc       9720
ctcagctcct ctaccccca atacagagat catcgagcgg gtgactcggg gtgagcagcc      9780 cccttccgg ccctccctgg ccctgcagag tcacctggag gagttggggc tgctcatgca       9840
gcggtgctgg gctgaggacc cacaggagag gccaccattc cagcagatcc gcctgacgtt      9900
gcgcaaattt aacaggtccc tggtgtttgt catggatccc ccaggcccctt cctccacagc     9960 caccatttac ctaatgcttc tggctctggc ttatcccagc agtggcagag ggagaccact      10020
cacctcctcc ctgtacatag tcagctccag ctcagcacag cctcatgacc ctcttcgcaa      10080
gtacagcatg actcagctgt ccccacagtc ccctgccatt catgcccctt ccctccacca      10140
tcgacacccc acacccttcc tgcccactcg ccttgctggc ctctagactt ctcagcagtg      10200
tgtaggatag atgggcctcc cgcctcctgc cctgtaggct cttggccctc cacgggagct      10260
cctgccccac cccttgattt cccttcccca gcgtgcccac caggcccagt tcctccagac      10320
acacccttct gtggacatca ctttgtccgc aattgaccct tgtcattctc cacctccttt      10380
acctccttct aactcactgg gttcaacaaa gatgaacaaa atgtccatat gtctgaagct      10440
tcatacttga ccttggggtc tcagaaaaga attgaacttt cttccttctg tttttcccctg     10500 ctccccggta tcctgctatg ccctcaaccc tgagcgtctc tagagacctc actgcagtct      10560
ggagggggaa gtgcctaggg gcgggcgctc acgtaggctg tgctgctcct ctcttaccac      10620
ccccaccgcc accctctgcc cccagggaga acagcagcaa catcctggac aacctgctgt      10680
cccgcatgga gcagtacgcg aacaatctgg aggaactggt ggaggagcgg acccaggcat      10740
acctggagga gaagcgcaag gctgaggccc tgctctacca gatcctgcct cagtgagtgc      10800
ctgagtctgg ggaccccccc caacacaaag cccctgtccc gacccccaac tctgatcctg      10860
cacctgccct gaccccttag ctcagtggct gagcagctga agcgtgggga gacggtgcag      10920
gccgaagcct ttgacagtgt taccatctac ttcagtgaca ttgtgggttt cacagcgctg      10980
tcggcggaga gcacacccat gcaggtaggc cagggttcag ccacaggtgc caggcaagct      11040
cagcatctgg atcccaccag acctgccttc tggttctgct ttaccacct gaccccaggt       11100 ggggtcccct acttcctgtc tctcttagct tctcttccct tccaggtggt gaccctgctc      11160
aatgacctgt acacttgctt tgatgctgtc atagacaact tgatgtgta caaggtgagg       11220 gtgggagtgg ggatgggaag ggacagacag acatggacaa ggtcagaaaa agatgagggg      11280
taggcagaat gatgtggagt cttaagagag gagatcgggg acacgggcag agacagtgac      11340
acagggagac ccgggaacag gcagagaacc catgtgggat gggggatgag caaagacaga      11400
tgagggtaca gaatgacaga cgctgcaccc ggtgtgacgg tgtggccggc cgcacagttg      11460
```

```
cagccgtcaa gtcctgcacc ccctcgccac tcccacaggt ggagacaatt ggcgatgcct    11520
acatggtggt gtcagggctc cctgtgcgga acgggcggct acacgcctgc gaggtagccc    11580
gcatggccct ggcactgctg gatgctgtgc gctccttccg aatccgccac cggccccagg    11640
agcagctgcg cttgcgcatt ggcatccaca caggtaaggc cactgaaggt gcaggcgggc    11700
atccagaggc caaggctttg caagggaaac ttgtcccctg gcccagcccc tcgccctttc    11760
atctctctct ctctctctct ctctctctct ctctctctct gtctctctct ctctctctct    11820
ctctctctct ctcacacaca cacacacaca cacacacaga gctgggacct cagatcctgc    11880
ctcctgcctg tcttggattg tccacctacc tcccttaaca cccctccctc cctcactcgc    11940
tgatgggctc tgctccttcc cttgctcctc ccaggacctg tgtgtgctgg agtggtggga    12000
ctgaagatgc cccgttactg tctctttggg gatacagtca acacagcctc aagaatggag    12060
tctaatgggg aaggtacagt gccccctcct agagggaatg gggagggcag ggtggctgag    12120
ggaaatgcca tcctggggca gcctgtgcct gcacagcccg tttcagctcc tagccctttc    12180
gcctcccaag ttccccttct cataatatta agagttcaac ctgggctcat caacttgact    12240
gtaaccagag actcaggttc ctgctgcccc tcttgtcaaa cgatgtaaaa gtatttccgg    12300
gccagtgctg gagagttccc agcaggaatc tgattttaag accctctgtg ggccgggcgt    12360
ggtgactcac acctgtgatc ccagcacttt ggaagctga ggcaggcgga tcacctgagg    12420 tcggggggttt cgagaccagc ctgaccaaca tgatgaaatc ccgtctctac taaaaataca    12480
aaaaactagc caggtgtgat ggcaggctcc tgtaatccca gctacttggg aggcttgagg    12540
cagaagaatt gcttgaaccc gggaggcaga ggttgcgatg agccaagatt acaccacgca    12600
ccccagcttg ggcaataaga gttaaactct gtctcaaaaa aaaaaaaaaa aaaaaaaaaa    12660
agggccctct gctccacctt tgatgtggta agatggctt cagagccagc ataagtgagg    12720
ctgtgaatct cagctccaca gctggctgtg tgtcagtttg ctatacctct ctgagccatg    12780
gttttcctca tctgtaaaaa gagggaaaaa atctatctca caggaattat gtgagaaacc    12840
cattaaaaat gtctaccaca taattgtcat ttaacttttc caagccttag cggattatct    12900 gtaaatgat gtctatctca ggattgcaag aagcctagca caaccctgg tacccagcag    12960 gcacctaata aattcttact cctacccgcc ccttgctctt gcctcctgtt tatcttctat    13020
ccttctgctg tattcgacac aattcaatgc agtaaacatt tattgagtga ctactgagtg    13080
ccaggccctg ggatagtaac atggcccaga tccagagtta gctgagaaat tcatgtggac    13140
cccatctaaa ccttatggtg aaagaaaggc tgcttgggag ccagtcctgg gagcccagag    13200
ggatctagtt cggcaaatat tccctgggca ctatttgggg gctgcagagt cagcccttgt    13260
tgagggtcca gtcctcaagg agcacattcc cagaaatgtt cacattctgg cgctggggtg    13320
ctgtaatccc agcactttgg gaggccgagg tgggcagatc acttgaggcc aggagtggag    13380
actagcctgg ccaacatggt gacctcctgt ctctactaaa aatacaaaaa attagctggg    13440
cgtggtggca cgtgcccgta atcccagcta ctcaggaggc ttgagacatg aaaatcactt    13500
gaacccagga ggtggatgtt gcagtgagcc gagactgcac ccctgggcaa cagagcgaga    13560
ctctgtctca aaaaaaaaa agagagaaag aagaaaaga aagaaagaa actgttaaac    13620 acaacaaggc cactgtgatt gatgcaaacc ccagaagtag ggacatgagt tcagacagtg    13680
gtcaaagaga gggtgtggca atattgggcc ccactccatc actgacctcc tcagccactt    13740
gggcagatca ccctgggcct cagttcctcg gccacaaaat gagggtatag catgaaatca    13800
tgaaagcaac aatttacata gtgcttccta ggtagcacat tccgtttgaa tactttatgg    13860
```

```
atgttaaatt taatcctcac aacaaggttt tgagatgggt actgacacta tcagcatttt    13920
acagattagg aaaatgaagc agagagaatt tattttacat acctaagcaa gtatccaagc    13980
tgaggttcat actgaggcag tgcaggatcc aaagtgccag ctcctaacca ccatgctgtg    14040
tagagccggg tgacactcca gagagtgctg tccaacagga tgttccatag tcatgaaaat    14100
gttctgtatt ctgtgctgtc aatacagta gcctctaggc acatatggct acttatcact     14160
ggaaatgtga cgggtgcaac tgaggccctg atttttttttt ttttttttgga gacagagttt   14220 cgctctgtcg cccagcctgg atggagtgca gtggtgcaat ctcggctcac tgcaacctcc    14280
gcctcccagg ttcaagcgat tctcctgcct cagcctccca gtagctgga attacaggtg     14340 agtgccacca cacacagcta attttttgtat tttagtaga cgggggttt cgccatattg     14400 gccaggatgg tctcgaactc ctggcctcaa gtgatcctcc tgcctcagcc tcccaaagtg    14460
ctgggattac aggtgtgagc cacagcaccc agcctgaatt tttaactgta tttagtttaa    14520
attaatttaa gttgaaacag gcacatgtga ttagtggcta ctgtattgga ttacacagct    14580
ccagagttct aaatgagagg ctaatgtggt cacgcactac attcagggg tggggcccct     14640 ctgagctaga gggcttcctg gcccaaaaga gggagagagg gtacctgtcc acctgtccac    14700
ccccacagtc cctggtctct tttgcctcta ctttcctgct ctcctctctc acattgctca    14760
ccttcccttc tccctgtcc tacccagccc tgaagatcca cttgtcttct gagaccaagg     14820
ctgtcctgga ggagtttggt ggtttcgagc tggagcttcg aggggatgta gaaatgaagg    14880
tagagcgaga agcctctgcc ctccccacct tttggggtcc tagagggagt tacccttctc    14940
aagcagccga tgccactccc atccctaagg ctctcatctg actggggaaa gggcatgtgc    15000
cactccccag cccatcctct tttttccctc cagggcaaag gcaaggttcg gacctactgg    15060
ctccttgggg agaggggag tagcacccga ggctgacctg cctcctctcc tatccctcca     15120 cacctccccct accctgtgcc agaagcaaca gaggtgccag gcctcagcct cacccacagc   15180
agccccatcg ccaaaggatg gaagtaattt gaatagctca ggtgtgctga ccccagtgaa    15240
gacaccagat aggacctctg agaggggact ggcatggggg gatctcagag cttacaggct    15300
gagccaagcc cacggccatg cacagggaca ctcacacagg cacacgcacc tgctctccac    15360
ctggactcag gccgggctgg gctgtggatt cctgatcccc tcccctcccc atgctctcct    15420
ccctcagcct tgctaccctg tgacttactg ggaggagaaa gagtcacctg aaggggaaca    15480
tgaaaagaga ctaggtgaag agagggcagg ggagcccaca tctggggctg cccacaata    15540 cctgctcccc cgaccccctc cacccagcag tagacacagt gcacagggga gaagaggggt    15600
ggcgcagaag ggttgggggc ctgtatgcct tgcttctacc atgagcagag acaattaaaa    15660
tctttattcc agtgacagtg tctcttcttg agggagagag ggttgccaga aaacagtcag    15720
ttctccactc tctacttcaa ataagactca cttcttgttc tacaagggtc tagaaggaaa    15780
agtaaaaaaa aaagactctc gattcttaac                                     15810
```

<210> SEQ ID NO 5
<211> LENGTH: 23
<212> TYPE: DNA
<213> ORGANISM: Artificial Sequence
<220> FEATURE:
<223> OTHER INFORMATION: NPRA specific forward primer

<400> SEQUENCE: 5
gcaaaggccg agttatctac atc                                              23

```
<210> SEQ ID NO 6
<211> LENGTH: 21
<212> TYPE: DNA
<213> ORGANISM: Artificial Sequence
<220> FEATURE:
<223> OTHER INFORMATION: NPRA specific reverse primer

<400> SEQUENCE: 6
aacgtagtcc tccccacaca a                                              21
```

MATERIALS AND METHODS FOR REDUCING INFLAMMATION BY INHIBITION OF THE ATRIAL NATRIURETIC PEPTIDE RECEPTOR

CROSS-REFERENCE TO RELATED APPLICATIONS

The present application is a continuation-in-part of U.S. application Ser. No. 11/059,814, filed Feb. 17, 2005, which claims the benefit of U.S. Provisional Application Ser. No. 60/521,072, filed Feb. 17, 2004. The present application also claims the benefit of U.S. Provisional Application Ser. No. 60/796,278, filed Apr. 28, 2006, which is hereby incorporated by reference herein in its entirety, including any figures, tables, nucleic acid sequences, amino acid sequences, and drawings.

BACKGROUND OF THE INVENTION

An atrial peptide with natriuretic and diuretic properties was first reported from rat atrial muscle in 1981. Since then a family of natriuretic hormone peptides (NP) with broad physiologic effects including vasodilation and inhibition of aldosterone secretion has been described. Atrial natriuretic factor (ANF), a 126 amino acid prohormone gives rise to four peptides: long acting natriuretic peptide (LANP, amino acids 1-30), vessel dilator (VD, residues 31-67), kaliuretic peptide (KP, residues 79-98) and atrial natriuretic peptide (ANP, residues 99-126, also referred to here as NP99-126) (Vesely, D L *Cardiovasc Res*, 2001 51:647-58). In addition, renal tubular cells produce urodilatin, a 32 amino acid peptide (residues 95-126 of ANF), which is released to circulation following differential processing of ANF (Forssmann et al. *Cardiovasc Res*, 2001, 51:450-62.). There is also a pro-brain natriutretic peptide (BNP) first discovered in porcine brain, which is analogous to ANP is found in circulation. The third type of natriuretic hormone, the C-type (CNP) comprises two peptides, 53 and 22 amino acids in length, which are produced by many cell types (Levin, E R et al. *N Eng J Med*, 1998, 339321-8). Of these peptides, the C-terminal pro-ANF, ANP, has been studied most extensively.

In keeping with the diversity of these NPs, there are three NP receptors (Misono, K S *Mol Cell Biochem*, 2002, 230(1-2):49-60; Tremblay, J et al. *Mol Cell Biochem*, 2002, 230(1-2):31-47). NPRa and NPRb, which are coupled to guanylyl cyclase, and the cGMP-independent receptor NPRc. ANP and BNP signal primarily through NPRa, which increases cGMP and activates cGMP-dependent protein kinase (PKG). PKG activation turns on the ion transport mechanism and activates specific transcription factors, which together affect a range of cellular activities including, cell growth and proliferation, apoptosis and inflammation. NPRC functions as a clearance receptor but also appears to signal phospholipase C activation and a decrease in adenylyl cyclase activity (Silberbach, M et al. *Cell Signal*, 2001 13:221-31). Numerous tissues of various organ systems including the lung express these receptors in diverse cells.

The NPs are produced in various tissues of the mucosa (lung, gastrointestinal and genitourinary systems), central nervous system and cardiovascular systems and released into the circulation. The signaling mechanisms underlying ANP's growth inhibitory effects are poorly understood, although a number of reports suggest that ANP affects signaling via activation of mitogen-activated protein kinases (Silberbach, M et al. *Cell Signal*, 2001 13:221-31). The potential effects may include inhibition of ERK activation of epidermal growth factor, PKG-induced uncoupling of Ras/Raf1 interaction, or induction of MKP-1, a MAPK phosphatase that inactivates signaling through a number of growth factors such as endothelin, EGF and FGF (Clark, A R *J Endocrinol*, 2003, 178: 5-12). ANP has been shown to mediate anti-inflammatory (Kiemer, A K and Vollmar *J Biol Chem*, 1998 273: 134444-51) and cytoprotective (Kiemer, A K et al., *J Immunol*, 2000, 165:175-81; Sprenger, H et al., *Immunobiology*, 1991, 183:94-101) effects. It has been shown to decrease cytokine and stress stimulated activation of NFκB in various cell types, leading to a decrease in pro-inflammatory cytokine production (Kiemer, A K and Vollmar *J Biol Chem*, 1998 273:134444-51; Kiemer, A K et al., *J Immunol*, 2000, 165: 175-81; Morita, R et al., *J Immunol*, 2003:170:5869-75). ANP can reduce tumor necrosis factor-α (TNF-α)-stimulated production of adhesion molecules in endothelium. (Kiemer, A K and Vollmar *J Biol Chem*, 1998 273:134444-51). It has also been shown to attenuate TNF-α-induced actin polymerization, through activation of MAPK phoshatase-1 (MKP-1) and inhibition of p38 activity, leading to decreased permeability (Clark, A R *J Endocrinol*, 2003, 178(1):5-12).

ANP stimulates migration of human neutrophils (Izumi, T et al. *J Clin Invest*, 2001, 108(2):203-21345), and inhibits nitric oxide (NO) and TNF-a production by murine macrophages (Vesely, D L et al. *Chest*, 1990, 97(6):1295-1298, Vesely, D L *Am J Obstet Gynecol*, 1991, 165(3):567-573). Human peripheral blood monocytes, however, do not express ANP receptors nor do they respond to ANP (Sprenger, H et al. *Immunobiology*, 1991, 183(1-2):94-101). The NP system, acting via cells of the innate immune system, modulates the immune response to antigens. Evidence to date suggests that it may augment allergic inflammation by acting on a number of cells in the lung (Kurihara, M et al. *Biochem Biophys Res Commun*, 1987, 149(3):1132-1140). The primary evidence supporting this notion is the finding that ANP acts via its receptor on dendritic cells to polarize these cells toward a Th2 phenotype, which is the hallmark of allergic immune response (Morita R et al. *J Immunol*, 2003, 170(12):5869-5875). In asthma, the production of inflammatory mediators secreted from resident epithelial cells and recruited immune cells results in airway hyperreactivity, which characterizes the late-phase airway response. Without intervention, this event leads to non-reversible airway remodeling (including sub-basement-membrane collagen deposition, smooth muscle hyperplasia and hypertrophy, and goblet cell hyperplasia), with subsequent airway narrowing and progression of the asthma.

A naturally occurring gene-silencing mechanism triggered by double-stranded RNA (dsRNA), designated as small interfering RNA (siRNA), has emerged as a very important tool to suppress or knock down gene expression in many systems. RNA interference is triggered by dsRNA that is cleaved by an RNAse-III-like enzyme, Dicer, into 21-25 nucleotide fragments with characteristic 5' and 3' termini (Provost, P. D. et al. *Embo J*, 2002, 21:5864). These siRNAs act as guides for a multi-protein complex, including a PAZ/PIWI domain containing the protein Argonaute2, that cleaves the target mRNA (Hammond, S. M. et al. *Science*, 2001, 293:1146-1150). These gene-silencing mechanisms are highly specific and potent and can potentially induce inhibition of gene expression throughout an organism. The short interference RNA (siRNA) approach has proven effective in silencing a number of genes of different viruses (Fire, A. *Trends Genet.*, 1999, 15:358-363).

RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., *Nature* 391:806-11 (1998); Sharp, *Genes Dev.* 13:139-41 (1999); Elbashir et al. *Nature* 411:494-98 (2001); Harborth et al., *J. Cell Sci.* 114:4557-65 (2001)). RNAi is mediated by double-stranded polynucleotides, such as double-stranded RNA (dsRNA), having sequences that correspond to exonic sequences encoding portions of the polypeptides for which expression is compromised. RNAi reportedly is not effected by double-stranded RNA polynucleotides that share sequence identity with intronic or promoter sequences (Elbashir et al., 2001). RNAi pathways have been best characterized in *Drosophila* and *Caenorhabditis elegans*, but "small interfering RNA" (siRNA) polynucleotides that interfere with expression of specific polynucleotides in higher eukaryotes such as mammals (including humans) have also been investigated (e.g., Tuschl, 2001 *Chembiochem.* 2:239-245; Sharp, 2001 *Genes Dev.* 15:485; Bernstein et al., 2001 *RNA* 7:1509; Zamore, 2002 *Science* 296:1265; Plasterk, 2002 *Science* 296:1263; Zamore 2001 *Nat. Struct. Biol.* 8:746; Matzke et al., 2001 *Science* 293: 1080; Scadden et al., 2001 *EMBO Rep.* 2:1107).

According to a current non-limiting model, the RNAi pathway is initiated by ATP-dependent, cleavage of long dsRNA into double-stranded fragments of about 18-27 (e.g., 19, 20, 21, 22, 23, 24, 25, 26, etc.) nucleotide base pairs in length, called small interfering RNAs (siRNAs) (see review by Hutvagner et al., *Curr. Opin. Gen. Dev.* 12:225-32 (2002); Elbashir et al., 2001; Nyknen et al., *Cell* 107:309-21 (2001); Zamore et al., *Cell* 101:25-33 (2000)). In *Drosophila*, an enzyme known as "Dicer" cleaves the longer double-stranded RNA into siRNAs; Dicer belongs to the RNase III family of dsRNA-specific endonucleases (WO 01/68836; Bernstein et al., *Nature* 409:363-66 (2001)). Further, according to this non-limiting model, the siRNA duplexes are incorporated into a protein complex, followed by ATP-dependent unwinding of the siRNA, which then generates an active RNA-induced silencing complex (RISC) (WO 01/68836). The complex recognizes and cleaves a target RNA that is complementary to the guide strand of the siRNA, thus interfering with expression of a specific protein (Hutvagner et al., supra).

In *C. elegans* and *Drosophila*, RNAi may be mediated by long double-stranded RNA polynucleotides (WO 99/32619; WO 01/75164; Fire et al., 1998; Clemens et al., *Proc. Natl. Acad. Sci. USA* 97:6499-6503 (2000); Kisielow et al., *Biochem. J.* 363:1-5 (2002); see also WO 01/92513 (RNAi-mediated silencing in yeast)). In mammalian cells, however, transfection with long dsRNA polynucleotides (i.e., greater than 30 base pairs) leads to activation of a non-specific sequence response that globally blocks the initiation of protein synthesis and causes mRNA degradation (Bass, *Nature* 411:428-29 (2001)). Transfection of human and other mammalian cells with double-stranded RNAs of about 18-27 nucleotide base pairs in length interferes in a sequence-specific manner with expression of particular polypeptides encoded by messenger RNAs (mRNA) containing corresponding nucleotide sequences (WO 01/75164; Elbashir et al., 2001; Elbashir et al., *Genes Dev.* 15:188-200 (2001)); Harborth et al., *J. Cell Sci.* 114:4557-65 (2001); Carthew et al., *Curr. Opin. Cell Biol.* 13:244-48 (2001); Mailand et al., *Nature Cell Biol.* Advance Online Publication (Mar. 18, 2002); Mailand et al. 2002 *Nature Cell Biol.* 4:317).

siRNA polynucleotides may offer certain advantages over other polynucleotides known in the art for use in sequence-specific alteration or modulation of gene expression to yield altered levels of an encoded polypeptide product. These advantages include lower effective siRNA polynucleotide concentrations, enhanced siRNA polynucleotide stability, and shorter siRNA polynucleotide oligonucleotide lengths relative to such other polynucleotides (e.g., antisense, ribozyme or triplex polynucleotides). By way of a brief background, "antisense" polynucleotides bind in a sequence-specific manner to target nucleic acids, such as mRNA or DNA, to prevent transcription of DNA or translation of the mRNA (see, e.g., U.S. Pat. No. 5,168,053; U.S. Pat. No. 5,190,931; U.S. Pat. No. 5,135,917; U.S. Pat. No. 5,087,617; see also, e.g., Clusel et al., 1993 *Nucl. Acids Res.* 21:3405-11, describing "dumbbell" antisense oligonucleotides). "Ribozyme" polynucleotides can be targeted to any RNA transcript and are capable of catalytically cleaving such transcripts, thus impairing translation of mRNA (see, e.g., U.S. Pat. No. 5,272, 262; U.S. Pat. No. 5,144,019; and U.S. Pat. Nos. 5,168,053, 5,180,818, 5,116,742 and 5,093,246; U.S. Ser. No. 2002/ 193579). "Triplex" DNA molecules refers to single DNA strands that bind duplex DNA to form a colinear triplex molecule, thereby preventing transcription (see, e.g., U.S. Pat. No. 5,176,996, describing methods for making synthetic oligonucleotides that bind to target sites on duplex DNA). Such triple-stranded structures are unstable and form only transiently under physiological conditions. Because single-stranded polynucleotides do not readily diffuse into cells and are therefore susceptible to nuclease digestion, development of single-stranded DNA for antisense or triplex technologies often requires chemically modified nucleotides to improve stability and absorption by cells. siRNAs, by contrast, are readily taken up by intact cells, are effective at interfering with the expression of specific polynucleotides at concentrations that are several orders of magnitude lower than those required for either antisense or ribozyme polynucleotides, and do not require the use of chemically modified nucleotides.

Due to its advantages, RNAi has been applied as a target validation tool in research in vitro and as a potential strategy for in vivo target validation and therapeutic product development (Novina, C. D. and Sharp, P. A., *Nature,* 2004, 430:161-164; Lieberman, J. et al. *Trends Mol. Med.,* 2003, 9(9):397-403). In vivo gene silencing with RNAi has been reported using viral vector delivery, liposomal delivery, and high-pressure, high-volume intravenous (i.v.) injection of synthetic iRNAs (Halder, J. et al. *Clin. Cancer Res.,* 2006, 12(16): 4916-4924; Landen, C. N. et al., *Cancer Biol. Ther.,* 2006, 5(12):1708-1713; Scherr, M. et al. *Oligonucleotides,* 2003, 13:353-363; Song, E. et al. *Nature Med.,* 2003, 347-351). In vivo gene silencing has been reported after local direct administration (intravitreal, intranasal, and intrathecal) of siRNAs to sequestered anatomical sites in various models of disease or injury, demonstrating the potential for delivery to organs such as the eye, lungs, and central nervous system (Reich, S. J. et al. *Mol. Vis.,* 2003, 9:210-216; Zhang, X. et al. *J. Biol. Chem.,* 2004, 279:10677-10684; Dorn, G. et al. *Nucleic Acids Res.,* 2004, 32, e49; Tolentino, M. J. et al. *Retina,* 2004, 24:132-138). Silencing of endogenous genes by systemic administration of siRNAs has also been demonstrated (Zimmerman, T. S. et al., *Nature,* 2006, 441(7089): 111-114; Soutschek, J. et al. *Nature,* 2004, 432:173-178).

The present inventors have demonstrated that, in contrast to prior knowledge that ANP decreases inflammatory mechanisms in the macrophages, ANP actually increases lung inflammation and this is caused by ANP-NPRA signaling. This signaling can be blocked by utilizing a small interference RNA (siRNA) approach, in which specific siRNAs targeted to NPRA can significantly decrease the inflammation. This results in amelioration of inflammation in allergic disease which may be caused by allergens and exacerbated by respiratory viral infections, pollutants, and smoke. Also, this may be beneficial in the amelioration of inflammation and tumorigenesis in cancers.

BRIEF SUMMARY OF THE INVENTION

The present invention pertains to a method for treating inflammatory diseases, respiratory allergies, such as allergic rhinitis and asthma, viral infections, and cancers using a polynucleotide (e.g., an siRNA, antisense nucleotide sequence, and/or ribozyme) or other agent that reduces expression of the atrial natriuretic peptide receptor A, NPRA, or otherwise reduces activity of the receptor (referred to herein as an NPRA inhibitor).

In one embodiment, the method of the present invention comprises administering a therapeutically effective amount of an NPRA inhibitor to a subject in need of such treatment. In one embodiment, the NPRA inhibitor is an interfering RNA molecule, such as siRNA, specifically targeted to NPRA. As used herein, NHP refers to atrial natriuretic factor (ANF) hormone, or a biologically active fragment or homolog thereof. Specifically exemplified siRNAs comprise an oligonucleotide sequence deduced from selected nucleotide sequence from the NPRA gene. Preferably, the siRNA is targeted to a sequence within the mRNA sequence encoded by SEQ ID NO:4.

In another embodiment, the method of the present invention comprises administering an effective amount of at least one nucleic acid molecule encoding an siRNA specifically targeted to NPRA (siNPRA) to a patient in need of such treatment. The present inventor has determined that introduction of a nucleic acid molecule encoding siNPRA is capable of inhibiting NPRA expression when introduced via a plasmid vector or a virus, in association with a desirable carrier molecule such as a lipid or polymer-based system. The siRNA delivery method of the present invention permits long-term expression of siNPRA encoding nucleic acid sequences in vivo, thereby conferring bronchoprotective effect and/or anti-inflammatory effect against respiratory allergies, such as asthma. Preferably, the siNPRA is targeted to a sequence within the mRNA sequence encoded by SEQ ID NO:4.

In one embodiment, a therapeutically effective amount of at least one nucleic acid molecule selected from the group consisting of SEQ ID NO:1, SEQ ID NO:2, and SEQ ID NO:3, or biologically active homologs of any of the foregoing, are administered to the subject. The nucleic acid molecule(s) can be administered with other inhibitors of NPRA and/or other agents having therapeutic efficacy in treatment of the disease.

In another aspect, the present invention concerns synthetic oligonucleotide having the sequence that acts as the interfering RNA (SEQ ID NOs:1-3) or a biologically active homolog of the foregoing. In another aspect, the present invention concerns a pharmaceutical composition comprising a nucleic acid sequence encoding an siNPRA and a pharmaceutically acceptable carrier, which can be administered by an accepted route.

BRIEF DESCRIPTION OF THE DRAWINGS

For a fuller understanding of the nature and objects of the invention, reference should be made to the following detailed description, taken in connection with the accompanying drawings, in which:

FIGS. 5A, 5B-1, and 5B-2 show that SiNPRA treatment appears to reduce cytokine production in BALB/c mice. 4-6 week old BALB/c mice (n=3) were sensitized and challenged with OVA (50 µg). All mice were sensitized intra-peritoneally (i.p.) and then challenged intranasally (i.n.). Mice were given two Si NPRA treatments by gavage and challenged 24 hours later. Thoracic lymph node cells (FIG. 5A) and spleen cells (FIGS. 5B-1 and 5B-2) were removed and cells cultured for 48 hours in the presence of OVA (Sigma Grade V) and recombinant mouse IL-2. Naïve mice received no treatment. Cells were treated with GolgiStop (BD Pharmingen) and stained for surface and intracellular cytokines (Antibodies obtained from BD Pharmingen). Percent cytokine secreting cells were quantified by intracellular cytokine staining using flow cytometry.

FIG. 13C shows that siNPRA treatment decreases melanoma tumor formation in the B16 mouse model. B16 melanoma cells ($1.3 \times 10^5$) were injected subcutaneously into twelve-week old female C57BL/6 mice. These mice were then treated with 33 μg of siNPRA-oligos, siNPRA plasmid, or scrambled oligos. All of these were mixed with chitosan at a ratio of 1:2.5. Mixed chitosan and plasmid or oligos were mixed again with cream before application to the injection area. The control group was given cream only. These treatments were given twice a week. Mice were sacrificed on day-22, and tumors were removed and weighed.

BRIEF DESCRIPTION OF THE SEQUENCES

Figure 1B:
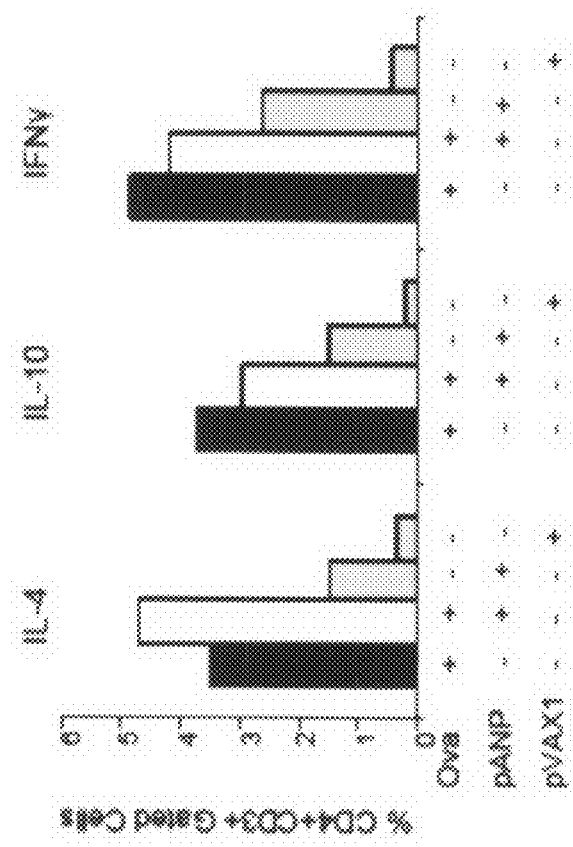
FIGS. 1A and 1B show a diagram depicting that overexpression of ANP in the lung augments inflammation and cytokine production in splenocytes. A) Normal BALB/c mice were given i.n. nanoparticles carrying pANP or pVAX and their lungs were examined 3 days after by staining the sections (H&E), showing goblet cell hyperplasia. B) Female BALB/c mice were given i.p. OVA (with alum) and then challenged i.n. OVA. Mice were sacrificed, the spleens aseptically removed and the cells were cultured for 48 hours in the presence of OVA (Sigma) and recombinant IL-2. Cells were removed from culture and stained for surface markers CD4 and CD3 and intracellular cytokines IL-4, IL-10 and IFN-g (BD Pharmingen).
Figure 1A:
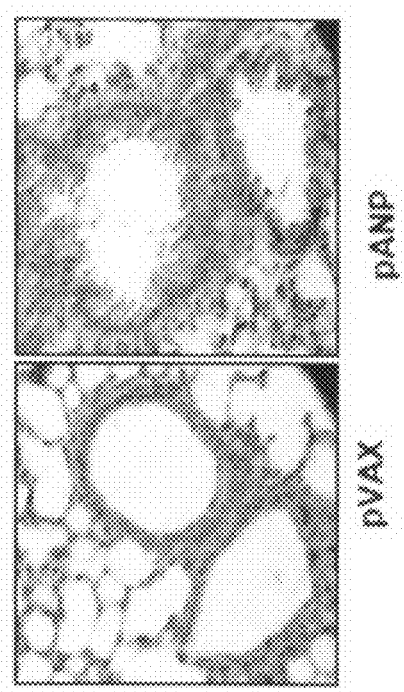

SEQ ID NO:1 is the nucleotide sequence of an siRNA for NPRA (siNPRA1): (targeting position 33): 5'-CAT ATG ggg ccc GGGCGCTGCTGCTGCTACCct cga aat GGT AGC AGC AGC AGC GCC CTT gaa ttc CCA TGG-3'.

SEQ ID NO:2 is the nucleotide sequence of an siRNA for NPRA (siNPRA2) (targeting position 72): 5'-CAT ATG ggg ccc GCGGCCACGCGAGCGACCTct cga aat AGG TCG CTC GCG TGG CCG CTT gaa ttc CCA TGG-3'.

SEQ ID NO:3 is the nucleotide sequence of an siRNA for NPRA (siNPRA3: (targeting position 33) siNPRA187top (si10): 5'-CAT ATG ggg ccc GGC TCG GCC GGA CTT GCT Gct cga aat CAG CAA GTC CGG CCG AGC CTT gaa ttc CCA TGG-3'.

```
SEQ ID NO: 4 is the nucleotide sequence encoding
human NPRA (NCBI Accession # AF190631:
    1 ggatcccaaa ccagcacacc tttccctctt ccccgagga
      gaccaggtag gaggcgaggg 61 aaaaggtggg gcgcaagtgg gccccggttg cttccacaca
      caccctccgt tcagccgtcc 121 tttccatccc ggcgagggcg caccttcaga gggtcctgtc
      ctccaaagag gtaggcgtgg 181 ggcggccgag accgggaag atggtccacg gggaagcgcg
      cgggctgggc ggcgggagg 241 aaggagtcta tgatcctgga ttggctcttc tgtcactgag
      tctgggaggg gaagcggctg 301 ggagggaggg ttcggagctt ggctcgggtc ctccacggtt
      ccctccggat agccggagac 361 ttgggccggc cggacgcccc ttctggcaca ctccctgggg
      caggcgctca cgcacgctac 421 aaacacacac tcctctttcc tccctcgcgc gccctctctc
      atccttcttc acgaagcgct 481 cactcgcacc ctttctctct ctctctctct ctctaacacg
      cacgcacact cccagttgtt 541 cacactcggg tcctctccag cccgacgttc tcctggcacc
      cacctgctcc gcggcgccct 601 gcacgccccc ctcggtcgcg ccccttgcgc tctcggccca
      gaccgtcgca gctacagggg
```

-continued

```
 661 gcctcgagcc ccggggtgag cgtccccgtc ccgctcctgc
     tccttcccat agggacgcgc 721 ctgatgcctg ggaccgccg ctgagcccaa ggggaccgag
     gaggccatgg taggagcgct 781 cgcctgctgc ggtgcccgct gaggccatgc cggggccccg
     gcgccccgct ggctcccgcc 841 tgcgcctgct cctgctcctg ctgctgccgc cgctgctgct
     gctgctccgg ggcagccacg 901 cgggcaacct gacggtagcc gtggtactgc cgctggccaa
     tacctcgtac ccctggtcgt 961 gggcgcgcgt gggacccgcc gtggagctgg ccctggccca
     ggtgaaggcg cgccccgact 1021 tgctgccggg ctggacggtc cgcacggtgc tgggcagcag
     cgaaaacgcg ctggcgtct 1081 gctccgacac cgcagcgccc ctggccgcgg tggacctcaa
     gtgggagcac aaccccgctg 1141 tgttcctggg ccccggctgc gtgtacgccg ccgccccagt
     ggggcgcttc accgcgcact 1201 ggcgggtccc gctgctgacc gccggcgccc cggcgctggg
     cttcggtgtc aaggacgagt 1261 atgcgctgac caccccgcgcg gggcccagct acgccaagct
     gggggacttc gtggcggcgc 1321 tgcaccgacg gctgggctgg gagcgccaag cgctcatgct
     ctacgcctac cggccgggtg 1381 acgaagagca ctgcttcttc ctcgtggagg ggctgttcat
     gcgggtccgc gaccgcctca 1441 atattaccggt ggaccacctg gagttcgccg aggacgacct
     cagccactac accaggctgc 1501 tgcgaccat gccgcgcaaa ggccgaggtg agacgctggc
     acaccccgtc ccgccgctta 1561 gccgcagggc ctcccctctg acctgccgga ggcatcggga
     cttctctct catctgggg 1621 cactcttctt tctcctcgcc gttcttcatt ctactttcag
     ctcccctggcc ctttctacag 1681 ctgagtttct atttccctct cttcttccgc cacccccacc
     acgtctctat cctctcatct 1741 ccccgacccc cactcattcc ctcccaccct agcacagctc
     ggttccggtc cctttttccc 1801 tcccacattt tctctcttcc ctatagcctt ctcccttctt
     tcatcctctc ctctcatggc 1861 gcctcatccc ctctcttctc cccctccctc tccctcctct
     ctccctcctg gccccatcct 1921 tctccacctt cagctccact atccccctct ccctacccgt
     tccttcctcc cttccgcctc 1981 ccccttcctc ctcccgccca ccgccccgca cccgcccgtt
     ccaccccttcg actttctcct 2041 gctgtggcct aggctgagcc gggagttacc acttaactct
     cactgggtct ctcctgcacc 2101 ctatctctaa acttcctccc ttgggtgccc cagctttcct
     actcctgtct ctcccgcagt 2161 acctaggctt ctctctctga ctctccgtct ttctccagtt
     atctacatct gcagtcccc 2221 tgatgccttc agaaccctca tgctcctggc cctggaagct
     ggcttgtgtg gggaggacta
```

```
2281 cgtttcttc cacctggata tctttgggca aagcctgcaa
     ggtggacagg gccctgctcc 2341 ccgcaggccc tgggagagag gggatgggca ggatgtcagt
     gcccgccagg ccttttcaggt 2401 gagtacctag gtttgaagcc caggctgtct cagcttgtgg
     cacatcattt ctgggcactg 2461 tgtccctcag catctgaaag aattccagaa aagaggtttt
     tgtctgtttg tttctttatg 2521 cactcctggt aactcacaga acagaaaaga ggttggtgat
     gctcactggg aattaggcaa 2581 tgaagggcag gggactgccc aggggcgctt cgccaccagc
     aggctaaaaa gataagaaaa 2641 tgggcttgag gcgggaggag gataaagtcc cacagcctgg
     acaggacttg gagaaggcat 2701 cccattggat cccctgcttt ggaatgggca tcacttcatg
     cagggcatag ggtccagttt 2761 gaccttgagc taagcagaga cgcagctctg ggaggtgggc
     tcccaactgt tggggcccca 2821 cagtactagg gaatagtcag ctcccaactc tctgctctcc
     actgacccct ttctcaggct 2881 gccaaaatca ttacatataa agacccagat aatcccgagt
     acttggaatt cctgaagcag 2941 ttaaaacacc tggcctatga gcagttcaac ttcaccatgg
     aggatggcct ggtaagaagg 3001 ggtcccggga ccctccagcg tggacctcca gcccccactc
     catgaccctc tgccagcctc 3061 catccttccc tattcccagt tctccccttc cttccctccc
     ttcccattgt tccatgtttc 3121 tcgtgatgat ggaggaggac actggcaagt tcagcctctg
     aaactcaggt catcatcagt 3181 aatatgaga cgatacatcc tgccctgtct acctagtagg
     attcaggaag tgatgctaat 3241 ccaaaggcat cgtttaaata gtaaaatctc cctgtgatat
     aggggtgtta ttttctccca 3301 tcctcttcca aaatcccagt gcctcttgtt cccttcccca
     cagctcccac ctccatgccc 3361 ttcatatgcc caccccagcc gacctctgtt tgcccctaca
     ggtgaacacc atcccagcat 3421 ccttccacga cgggctcctg ctctatatcc aggcagtgac
     ggagactctg gcacatgggg 3481 gaactgttac tgatggggag aacatcactc agcggatgtg
     gaaccgaagc tttcaaggtc 3541 agggcctgga ggtggctgga atgggctgcc ttgggggatg
     aatcccaggt gcccagtgtc 3601 aagccatgag aagcctattg tcctgcagca gttacctatg
     cacaccagcc ttttcctcca 3661 cagctttttt caggcccatc cctcagaagt cctacaaagt
     gtccaatctc aatcatccct 3721 gctgggcact gagttctttt acctttcttt ttctttttc
     tttttttttt gagatgggagt 3781 ctcgctctgt ccccaagact ggagtgtggt ggtgcaatct
     cggctcactt caacctccgc 3841 ctcccaggtt caagcaattc tcctgcctca gcctcctgag
     tagctgggat tacaggtgcc
```

-continued

```
3901 ctccaccaac acttggctaa ttttttgtat ttttttttagt
     agagacaggg tttcaccacg 3961 ttggtcaggc tggtcttgaa ctcctgacgt caggtgatct
     gcccgcctca gcctcccaaa 4021 gtgctgggat tacaagcatg agccacagtg cccggccgtt
     ttaccattta ctatcattct 4081 gtatacatgt atgtttggaa ggcaaggcaa aaaagattag
     aggatgaaga gatgaagtgg 4141 ggcacccctg aacttctatt ctctcaaaca tagtcatctt
     cccccatgtc ctcaggtgtg 4201 acaggatacc tgaaaattga tagcagtggc gatcgggaaa
     cagacttctc cctctgggat 4261 atggatcccg agaatggtgc cttcagggta agtttgtgca
     cccagaagac agtgccaatt 4321 ccaaatgaca tctcaccctc ctacttcccc cccacagccc
     tgccagggca cctgtttatc 4381 ctgtagccat tccaccatgc ctggacactt acaagagccc
     tggataaaac agacccagct 4441 ccagtctggg gaagccacca gaatgatagg gactcacagg
     catcacactt ggggagcccc 4501 atgcctgagg agggagcaca agcctgccct cggggagctc
     cgaagggagg caggcaggac 4561 cgcctcccag cagagacagg gctgtgaaag atgcacatta
     cacagctctg caagcgagca 4621 gggacaggaa ggcgctgagg ccaatggcca caagggacag
     gtcatccaga gaaggcctcc 4681 tggaagacgg gcacatggac tgggcctgcg aatgtaggct
     aaggtgaaca ttaccttctc 4741 ctgttttcta ccaagaaaat aagtagagaa aaatcaatgc
     ttggttggta cttcaaccaa 4801 gattataaac tccctgagtg tagagatcgg gttctaaatg
     gagttttctt tataaacccc 4861 ttgatagttt tcaggtgttt ccacttgagt actatgtgtg
     tggtatgagg tcctgtgtcc 4921 agttgcagtg gggacttggt aagcaggtga caacccagat
     atatatgtag gctctagaag 4981 cagagctggg gtaggtggga ggtgagactg ctgcactcac
     agcatgcctt ccccgcaggc 5041 cctggcctag ccaccactcc tgctctccct taggttgtac
     tgaactacaa tgggacttcc 5101 caagagctgg tggctgtgtc ggggcgcaaa ctgaactggc
     ccctggggta ccctcctcct 5161 gacatcccca aatgtggctt tgacaacgaa gacccagcat
     gcaaccaagg tgactgcccc 5221 ttgccttcca ggcctccatc ccagagatgc tgcatccttc
     ccctaagcac agtcgagtag 5281 gtgctcctgt cccatgctga gggctttctg gagaatgact
     cctgcctttt tcttcccttc 5341 atccatcatc ccagttcact gatggactat tagaaagttc
     ttcctcctgc tgtctaaccc 5401 aaatctctct tgctgcaata tggactctct cctgcagatc
     acctttccac cctgaggtg 5461 ctggctttgg tgggcagcct ctccttgctc ggcattctga
     ttgtctcctt cttcatatac
```

```
5521 aggtgagctg tgatgtgggg ggttgagtga ggctggggga
     cccggagaac caagagcaga 5581 ggaggcggtg gggacccaga gggaagaggg caggggtgaa
     ggggcagcag ggggaaaacca 5641 agggagatga ggaagaaagg aggcttaaaa gccagaggag
     aaagaaagag aagggaatgg 5701 cagggcgagg ggaggagaca aggataggaa tggccaagga
     gagtcagaaa gatccaagaa 5761 gcagagaagt tgatgggtga catcataggg gcgtggactg
     gttttccttg ctactcttgc 5821 aggccagata ggaagcaact ttctgaacct ttgcaatcat
     gcccatgtta gctgaggagg 5881 gtgagcctg tgtgtgcca ggtgcccaac ctagaatgga
     gaagggagct gaatgagcct 5941 tgttcctgcc gtccagtgga ggctaaaatg aagtacagga
     ggagttaatg atatacaaaa 6001 gcaaggaggg agggagaaa atcactgct ggttgagcat
     ataatgtgtg ccaggcactt 6061 ccacgtacac tatttctttc tttctttttt ttttttttt
     tttttttttg agacgagtc 6121 tcgctctgtt gccagactgg agtgcagtgg catgatctag
     gctcactgca acctccgcct 6181 cccagtttca agcaattctc ctgcctcagc ctcccatgta
     gctgggacta caggcacatg 6241 ccaccacgct cagctaattt ttgtattttt agtagagaca
     gggtttcacc atgttggcca 6301 ggatggtctc gatctcttga cctcatgatc cacccacctt
     ggcctcccaa agtgctggga 6361 ttacaggcat gagccactgt gcctggcctc atgttcacta
     tttcttttca ttcttataat 6421 agttaagaat gaaatagata ttgcggcctc attcccaagt
     aaggacattg aggtgattcc 6481 cccaaggtcc ccagtaaggc agaatttccc ccagccatcc
     tgattctcag tccagaggat 6541 agaattcccc ctccatctct gagtgcatgg tgtggtccca
     cggctctgag gaggggctgc 6601 tgagcaccct gccctgggtc agcggctcag ccacaggctc
     agatgcagcc ttcgtatccc 6661 aggaagatgc agctggagaa ggaactggcc tcggagctgt
     ggcgggtgcg ctgggaggac 6721 gttgagccca gtagccttga gaggcacctg cggagtgcag
     gcagccggct gaccctgagc 6781 ggggtaagaa cgctggtgtt tgtgttgggg ggcaataaag
     gagaggtggg tacaagggc 6841 agtgcctgag ggataggtaa gggagcagga ttctagtccc
     agctctgctt tcacttgctg 6901 tgtgaccttg agcgactcat agtccctctc cgagactgtc
     tcagatgatg attacagcag 6961 cagagcctcc ctcacagggc tctttttaaag gtcagaggag
     atagtacctg tgaaaacact 7021 ttaaaaaaaa aaaaagtaaa tgaggaggaa attttatgat
     gtggaacata aagcagggtg 7081 ggccaggcac agtggctcac atctgcaatc ccagcacttt
     gggagaccga ggcaggagga
```

```
7141  ttgcttgtgc ctggggagttc aagaccagcc tgggcaacag
      agcaagacat cgtctctaca 7201  aagaatacaa agattagcag ggcatggtgg cgcatacctg
      tagtcccagc tactctggag 7261  gctgaggtga aaggatcatc tgagcccagg agtctgaggc
      ggcagtgacc taggatagca 7321  ccactgcact ccagcctgga tgacacaatg atactacatc
      tcaaaaaaaa acccaacaac 7381  aaaaaggaag ggtgacacaa agataaggca ggataaggca
      gggaaataaa gaccagagca 7441  caagcaatca ggatgcagac tgggcccacc ggctgaccat
      tcctcctgct ctccctcctt 7501  tcagagaggc tccaattacg gctccctgct aaccacagag
      ggccagttcc aagtctttgc 7561  caagacagca tattataagg tgggcctggg gaaagatcac
      tgggccttgg gactggggca 7621  ggagtgtact ctgatggagc actggtgggg ggttctgagg
      gaaggagtaa gctggtgggg 7681  agcagcagat gggggccctg ggggtgggct attgggaaca
      agtgagggtc ctgagggcag 7741  ggatgggctg tcgggagcag ctggaattcc caggacatgg
      gaccatgctc ttcacagtga 7801  cagtctccat tccatgccca gggcaacctc gtggctgtga
      aacgtgtgaa ccgtaaacgc 7861  attgagctga cacgaaaagt cctgtttgaa ctgaagcatg
      taatgtgggg agtgaggcag 7921  tggcatggag aagggggccct cggggacgca agggagactg
      gccaacagaa ctagttatgg 7981  agggacctca gggtacccca agaaaggggc agggactgga
      gccctggatg accttcatct 8041  tgtggtggag tgggggtatc ctaagtagga gaagagacca
      ctgagataac ctggaggaat 8101  cttgaggggc catatgtgat gtccctgggg gagagagggc
      ttaggatgcc agagggagta 8161  ggagcagatt ctggggaggg tgggctaaag gacatgggtg
      ggaatcacca gggaagatct 8221  tagtgatggt tgcagaaagt gaataaggag ttaagaagag
      tgagggtccc tgaagctagt 8281  gagcagcttg gtgaggagcg aggtctctgt caagctcctg
      atgctggtcc cacttgcaga 8341  tgcgggatgt gcagaatgaa cacctgacca ggtttgtggg
      agcctgcacc gaccccccca 8401  atatctgcat cctcacagag tactgtcccc gtgggagcct
      gcaggtgagg gggacaaggg 8461  gtgtcaagaa acctgggttc tagccctggc tctgccctg
      actggccata agaccccagg 8521  catgcctcgc cctctttctg acctttctgg ccccatctgt
      aaaaatggga gttggggaag 8581  ggcagtggca ctagagtcaa tccaaagttt tgtcctgttc
      taccagttca catcagtagg 8641  accctgcacc ctccctccaac tcccagggg atctgcaggg
      gattggtctt gactcttatt 8701  gccccagcag gacattctgg agaatgagag catcacccctg
      gactggatgt tccggtactc 8761  actcaccaat gacatcgtca aggtatgccc ctaagcacct
      attggatgtg tagagcaggg 8821  gccaggcatg cttctcctgg ccacgggtgt aggtcccact
      cctggccaat acctctgccc 8881  actcacattt ccagggcatg ctgtttctac acaatggggc
      tatctgttcc catgggaacc 8941  tcaagtcatc caactgcgtg gtagatgggc gctttgtgct
      caagatcacc gactatgggc 9001  tggagagctt cagggacctg gacccagagc aaggacacac
      cgtttatgcc agtgagcctt 9061  gactcttgaa cctaacacct gccccagca ccacccagta
      gggagactga tgcaaggcct 9121  ctgatgggct tgggcatgct tgtcctgact ccagcctcaa
      ttcattcacc catgaaaaag 9181  ggaaggccag acgaagtggt ttctaaggcc tcctctagct
      ctaacactct gtgatgcatc 9241  cagatcagtt tcggccacac ccttgtttcc ccctcacccc
      ttagctttgg gctccctcac 9301  tcggtgacta ccgacctctg acccacagaa aagctgtgga
      cggccctga gctcctgcga 9361  atggcttcac cccctgtgcg gggctcccag gctggtgacg
      tatacagctt tgggatcatc 9421  cttcaggaga ttgccctgag gagtgggtc ttccacgtgg
      aaggttttgga cctgagcccc 9481  aaaggtgaga ggagcacacc ttccttaaac ccagccacag
      tctcaacgaa ccccagcccc 9541  agggagaggg tccctggca gcaccaccac accttccttc
      tgtaatgggg ttcagtcacc 9601  accctttgac ccattgctgc cagtgaccag tcccccgccc
      ccatgccttg gtcttggact 9661  tcccctgcca tctcagctgg ttgccccagt ctctcactag
      gcccttggcc agcccaccc 9721  ctcagctcct ctaccccca atacagagat catcgagcgg
      gtgactcggg gtgagcagcc 9781  ccccttccgg ccctcctgg ccctgcagag tcacctggag
      gagttggggc tgctcatgca 9841  gcggtgctgg gctgaggacc cacaggagag gccaccattc
      cagcagatcc gcctgacgtt 9901  gcgcaaattt aacaggtccc tggtgtttgt catggatccc
      ccaggccctt cctccacagc 9961  caccattta ctaatgcttc tggctctggc ttatcccagc
      agtggcagag ggagaccact 10021 cacctcctcc ctgtacatag tcagctccag ctcagcacag
      cctcatgacc ctcttcgcaa 10081 gtacagcatg actcagctgt ccccacagtc ccctgccatt
      catgcccctt cctccacca 10141 tcgacacccc acaccttcc tgcccactcg ccttgctggc
      ctctagactt ctcagcagtg 10201 tgtaggatag atgggcctcc cgcctcctgc cctgtaggct
      cttggccctc cacgggagct 10261 cctgccccac cccttgattt ccttcccca gcgtgcccac
      caggcccagt tcctccagac 10321 acaccccttct gtggacatca ctttgtccgc aattgaccct
      tgtcattctc cacctccttt
```

```
10381  acctccttct aactcactgg gttcaacaaa gatgaacaaa
       atgtccatat gtctgaagct 10441  tcatacttga ccttggggtc tcagaaaaga attgaacttt
       cttccttctg ttttcccctg 10501  ctccccggta tcctgctatg ccctcaaccc tgagcgtctc
       tagagacctc actgcagtct 10561  ggaggggaa gtgcctaggg gcgggcgctc acgtaggctg
       tgctgctcct ctcttaccac 10621  ccccaccgcc accctctgcc cccagggaga acagcagcaa
       catcctggac aacctgctgt 10681  cccgcatgga gcagtacgcg aacaatctgg aggaactggt
       ggaggagcgg acccaggcat 10741  acctggagga gaagcgcaag gctgaggccc tgctctacca
       gatcctgcct cagtgagtgc 10801  ctgagtctgg gaccccccc caacacaaag cccctgtccc
       gaccccccaac tctgatcctg 10861  cacctgccct gacccccttag ctcagtggct gagcagctga
       agcgtgggga gacggtgcag 10921  gccgaagcct ttgacagtgt taccatctac ttcagtgaca
       ttgtgggttt cacagcgctg 10981  tcggcggaga gcacacccat gcaggtaggc cagggttcag
       ccacaggtgc caggcaagct 11041  cagcatctgg atcccaccag acctgccttc tggttctgct
       ttaccacct gaccccaggt 11101  ggggtcccct acttcctgtc tctcttagct tctcttccct
       tccaggtggt gaccctgctc 11161  aatgacctgt acacttgctt tgatgctgtc atagacaact
       ttgatgtgta caaggtgagg 11221  gtgggagtgg ggatgggaag ggacagacag acatggacaa
       ggtcagaaaa agatgagggg 11281  taggcagaat gatgtggagt cttaagagag gagatcgggg
       acacgggcag agacagtgac 11341  acaggagac ccgggaacag gcagagaacc catgtgggat
       gggggatgag caaagacaga 11401  tgagggtaca gaatgacaga cgctgcaccc ggtgtgacgg
       tgtggccggc cgcacagttg 11461  cagccgtcaa gtcctgcacc ccctcgccac tcccacaggt
       ggagacaatt ggcgatgcct 11521  acatggtggt gtcagggctc cctgtgcgga acgggcggct
       acacgcctgc gaggtagccc 11581  gcatggccct ggcactgctg gatgctgtgc gctccttccg
       aatccgccac cggcccagg 11641  agcagctgcg cttgcgcatt ggcatccaca caggtaaggc
       cactgaaggt gcaggcgggc 11701  atccagaggc caaggctttg caagggaaac ttgtcccctg
       gcccagcccc tcgccctttc 11761  atctctctct ctctctctct ctctctctct ctctctctct
       gtctctctct ctctctctct 11821  ctctctctct ctcacacaca cacacacaca cacacacaga
       gctgggacct cagatcctgc 11881  ctcctgcctg tcttggattg tccacctacc tcccttaaca
       cccctcccte cctcactcgc 11941  tgatgggctc tgctccttcc cttgctcctc ccaggacctg
       tgtgtgctgg agtggtggga
```

```
12001  ctgaagatgc cccgttactg tctctttggg gatacagtca
       acacagcctc aagaatggag 12061  tctaatgggg aaggtacagt gccccctcct agagggaatg
       gggagggcag ggtggctgag 12121  ggaaatgcca tcctggggca gcctgtgcct gcacagcccg
       tttcagctcc tagcccttc 12181  gcctcccaag ttcccttct cataatatta agagttcaac
       ctgggctcat caacttgact 12241  gtaaccagag actcaggttc ctgctgcccc tcttgtcaaa
       cgatgtaaaa gtatttccgg 12301  gccagtgctg gagagttccc agcaggaatc tgattttaag
       accctctgtg ggccgggcgt 12361  ggtgactcac acctgtgatc ccagcacttt gggaagctga
       ggcaggcgga tcacctgagg 12421  tcggggtttt cgagaccagc ctgaccaaca tgatgaaatc
       ccgtctctac taaaaataca 12481  aaaaactagc caggtgtgat ggcaggctcc tgtaatccca
       gctacttggg aggcttgagg 12541  cagaagaatt gcttgaaccc gggaggcaga ggttgcgatg
       agccaagatt acaccacgca 12601  ccccagcttg gcaataaga gttaaactct gtctcaaaaa
       aaaaaaaaaa aaaaaaaaa 12661  agggccctct gctccacctt tgatgtggta aagatggctt
       cagagccagc ataagtgagg 12721  ctgtgaatct cagctccaca gctggctgtg tgtcagtttg
       ctatacctct ctgagccatg 12781  gttttcctca tctgtaaaaa gagggaaaaa atctatctca
       caggaattat gtgagaaacc 12841  cattaaaaat gtctaccaca taattgtcat ttaacttttc
       caagccttag cggattatct 12901  gtaaaatgat gtctatctca ggattgcaag aagcctagca
       caaaccctgg tacccagcag 12961  gcacctaata aattcttact cctacccgcc ccttgctctt
       gcctcctgtt tatcttctat 13021  ccttctgctg tattcgacac aattcaatgc agtaaacatt
       tattgagtga ctactgagtg 13081  ccaggccctg ggatagtaac atggcccaga tccagagtta
       gctgagaaat tcatgtggac 13141  cccatctaaa cctatggtg aaagaaaggc tgcttgggag
       ccagtcctgg gagcccagag 13201  ggatctagtt cggcaaatat tccctgggca ctatttgggg
       gctgcagagt cagcccttgt 13261  tgagggtcca gtcctcaagg agcacattcc cagaaatgtt
       cacattctgg cgctggggtg 13321  ctgtaatccc agcactttgg gaggccgagg tgggcagatc
       acttgaggcc aggagtggag 13381  actagcctgc ccaacatggt gacctcctgt ctctactaaa
       aatacaaaaa attagctggg 13441  cgtggtggca cgtgcccgta atcccagcta ctcaggaggc
       ttgagacatg aaaatcactt 13501  gaacccagga ggtggatgtt gcagtgagcc gagactgcac
       ccctgggcaa cagagcgaga 13561  ctctgtctca aaaaaaaaaa agagagaaag aaagaaaaga
       aaagaaagaa actgttaaac
```

```
-continued
13621 acaacaaggc cactgtgatt gatgcaaacc ccagaagtag
      ggacatgagt tcagacagtg 13681 gtcaaagaga gggtgtggca atattgggcc ccactccatc
      actgacctcc tcagccactt 13741 gggcagatca ccctgggcct cagttcctcg gccacaaaat
      gagggtatag catgaaatca 13801 tgaaagcaac aatttacata gtgcttccta ggtagcacat
      tccgtttgaa tactttatgg 13861 atgttaaatt taatcctcac aacaaggttt tgagatgggt
      actgacacta tcagcatttt 13921 acagattagg aaaatgaagc agagagaatt tattttacat
      acctaagcaa gtatccaagc 13981 tgaggttcat actgaggcag tgcaggatcc aaagtgccag
      ctcctaacca ccatgctgtg 14041 tagagccggg tgacactcca gagagtgctg tccaacagga
      tgttccatag tcatgaaaat 14101 gttctgtatt ctgtgctgtc caatacagta gcctctaggc
      acatatggct acttatcact 14161 ggaaatgtga cgggtgcaac tgaggccctg attttttttt
      tttttttgga gacagagttt 14221 cgctctgtcg cccagcctgg atggagtgca gtggtgcaat
      ctcggctcac tgcaacctcc 14281 gcctcccagg ttcaagcgat tctcctgcct cagcctccca
      agtagctgga attacaggtg 14341 agtgccacca cacacagcta attttttgtat ttttagtaga
      gacggggttt cgccatattg 14401 gccaggatgg tctcgaactc ctggcctcaa gtgatcctcc
      tgcctcagcc tcccaaagtg 14461 ctgggattac aggtgtgagc cacagcaccc agcctgaatt
      tttaactgta tttagtttaa 14521 attaatttaa gttgaaacag gcacatgtga ttagtggcta
      ctgtattgga ttacacagct 14581 ccagagttct aaatgagagg ctaatgtggt cacgcactac
      attcagggg tggggcccct 14641 ctgagctaga gggcttcctg gcccaaaaga gggagagagg
      gtacctgtcc acctgtccac 14701 ccccacagtc cctggtctct tttgcctcta ctttcctgct
      ctcctctctc acattgctca 14761 ccttcccttc tccctgtcc tacccagccc tgaagatcca
      cttgtcttct gagaccaagg 14821 ctgtcctgga ggagtttggt ggtttcgagc tggagcttcg
      aggggatgta gaaatgaagg 14881 tagagcgaga agcctctgcc ctccccacct tttggggtcc
      tagagggagt taccccttctc 14941 aagcagccga tgccactccc atccctaagg ctctcatctg
      actggggaaa gggcatgtgc 15001 cactcccccag cccatcctct ttttttccctc cagggcaaag
      gcaaggttcg gacctactgg 15061 ctccttgggg agaggggag tagcacccga ggctgacctg
      cctcctctcc tatccctcca 15121 cacctcccct accctgtgcc agaagcaaca gaggtgccag
      gcctcagcct cacccacagc 15181 agcccatcg ccaaaggatg gaagtaattt gaatagctca
      ggtgtgctga ccccagtgaa 15241 gacaccagat aggacctctg agaggggact ggcatggggg
      gatctcagag cttacaggct 15301 gagccaagcc cacggccatg cacagggaca ctcacacagg
      cacacgcacc tgctctccac 15361 ctggactcag gccgggctgg gctgtggatt cctgatcccc
      tcccctcccc atgctctcct 15421 ccctcagcct tgctaccctg tgacttactg ggaggagaaa
      gagtcacctg aaggggaaca 15481 tgaaaagaga ctaggtgaag agagggcagg ggagcccaca
      tctgggctg gcccacaata 15541 cctgctcccc cgaccccctc cacccagcag tagacacagt
      gcacagggga gaagaggggt 15601 ggcgcagaag ggttgggggc ctgtatgcct tgcttctacc
      atgagcagag acaattaaaa 15661 tctttattcc agtgacagtg tctcttcttg agggagagag
      ggttgccaga aaacagtcag 15721 ttctccactc tctacttcaa ataagactca cttcttgttc
      tacaagggtc tagaaggaaa 15781 agtaaaaaaa aaagactctc gattcttaac
```

DETAILED DISCLOSURE OF THE INVENTION

The present invention provides a method for reducing atrial natriuretic peptide receptor A (NPRA) gene expression and/or function within a subject by administering an effective amount of an NPRA inhibitor to the subject. In one embodiment, the NPRA inhibitor is a polynucleotide that is specific for one or more target NPRA genes such that the polynucleotide decreases NPRA gene expression within the subject. In another embodiment, the NPRA inhibitor is a chemical compound, such as an oxindole (e.g., isatin). The method of the invention is useful for treating inflammatory diseases in human subjects and non-human subjects suffering from, or at risk for developing, inflammatory reactions.

The present invention includes, but is not limited to, the following embodiments:

Embodiment 1: an isolated polynucleotide targeted to a target nucleic acid sequence within a natriuretic peptide receptor A (NPRA) gene or NPRA transcript, wherein said polynucleotide inhibits expression of said NPRA gene or transcript.

Embodiment 2: the polynucleotide of embodiment 1, wherein the NPRA is human NPRA (e.g., encoded by SEQ ID NO:4).

Embodiment 3: the polynucleotide of embodiment 1, wherein the target nucleic acid sequence is at least a portion of the human NPRA gene or transcript.

Embodiment 4: the polynucleotide of any of embodiments 1 to 3, wherein the target nucleic acid sequence is located in a region selected from the group consisting of the 5' untranslated region (UTR), transcription start site, translation start site, and 3' UTR.

Embodiment 5: the polynucleotide of any of embodiments 1 to 4, wherein the polynucleotide is a small interfering RNA (siRNA).

Embodiment 6: the polynucleotide of any of embodiments 1 to 4, wherein the polynucleotide is an antisense molecule.

Embodiment 7: the polynucleotide of any of embodiments 1 to 4, wherein the polynucleotide is a ribozyme.

Embodiment 8: the polynucleotide of embodiment 1, wherein the polynucleotide comprises SEQ ID NO:1, or SEQ ID NO:2, or SEQ ID No:3.

Embodiment 9: the polynucleotide of embodiment 1, wherein the NPRA gene or NPRA transcript is at least a portion of the mammal gene or transcript.

Embodiment 10: a method for reducing NPRA function in a subject, comprising administering an NPRA inhibitor to the subject, such as the polynucleotide of any of embodiments 1 to 9, wherein the polynucleotide is administered in an effective amount to reduce expression of the NPRA gene or transcript.

Embodiment 11: the method of embodiment 10, wherein the subject is suffering from an inflammatory disease, respiratory allergy, viral infection (such as respiratory virus infection), or cancer (such as melanoma, lung cancer, or ovarian cancer).

Embodiment 12: the method of embodiment 10, wherein the subject is not suffering from an inflammatory disease, respiratory allergy, viral infection, or cancer.

Embodiment 13: the method of any one of embodiments 10 to 12, wherein the subject is human.

Embodiment 14: the method of any one of embodiments 10 to 12, wherein the subject is a non-human mammal.

Embodiment 15: the method of any one of embodiments 10 to 14, wherein the NPRA inhibitor is delivered to cells within the subject selected from the group consisting of respiratory epithelial cells, dendritic cells, and monocytes.

Embodiment 16: the method of any one of embodiments 10 to 15, wherein the NPRA inhibitor is administered to the subject intranasally.

Embodiment 17: the method of any one of embodiments 10 to 16, wherein the NPRA inhibitor is administered intranasally as drops or as an aerosol, or orally or transdermally.

Embodiment 18: the method of any one of embodiments 10 to 17, wherein step of administering comprises administering a combination of NPRA inhibitors that reduce the function of NPRA within the subject (such as a combination of polynucleotide, e.g., an siRNA pool).

Embodiment 19: the method of any one of embodiments 10 to 18, wherein the NPRA inhibitor is a siRNA and wherein the siRNA reduces expression of NPRA within the subject.

Embodiment 20: the method of any one of embodiments 10 to 18, wherein the NPRA inhibitor is an oxindole, such as 5-hydroxyoxindole or isatin, or a pharmaceutically acceptable salt thereof (Cane, A. et al. *Biochem. Biophy. Res Comm*, 2000, 276:379-384; Vine, K. L. et al. *Bioorg Med Chem*, 2007, 15(2):931-938; Abadi, A. H. et al. *Eur J Med Chem*, 2006, 41(3):296-305; Igosheva, N. et al. *Neurochem Int*, 2005, 47(3):216-224; Liu, Y. et al. *Chem Biol*, 2003, 10(9): 837-846; Levy, J. A. et al. *Virology*, 1976, 74(2):426-431; Popp, F. D. *J Med Chem*, 1969, 12(1):182-184). Isatin (also known as 1H-indole-2,3-dione) is an indole derivative (Sumpter, W. C. *Chem Rev*, 34(3):393-434; Ogata, A. et al. *J Neurol Sci*, 2003, 206(1):79-83; Glover, V. et al. *J Neurochem*, 1988, 51(2):656-659; Filomeni, G. et al. *J Biol Chem*, 2007, 282(16):12010-12021).

As used herein, the term "polypeptide" refers to any polymer comprising any number of amino acids, and is interchangeable with "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference or otherwise reduce target gene expression.

As used herein, the term "operably-linked" or "operatively-linked" refers to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a siRNA will typically have its own operably-linked promoter sequence.

The term "vector" or "vehicle" is used to refer to any molecule (e.g., nucleic acid, plasmid, or virus) used to transfer coding information (e.g., a polynucleotide of the invention) to a host cell. The term "expression vector" refers to a vector that is suitable for use in a host cell (e.g., a subject's cell) and contains nucleic acid sequences which direct and/or control the expression of exogenous nucleic acid sequences. Expression includes, but is not limited to, processes such as transcription, translation, and RNA splicing, if introns are present. The vectors of the present invention can be conjugated with chitosan or chitosan derivatives. Such chitosan conjugates can be administered to hosts according to the methods of the present invention. For example, polynucleotide chitosan nanospheres can be generated, as described by Roy, K. et al. (*Nat Med*, 1999, 5:387). Chitosan allows increased bioavailability of the nucleic acid sequences because of protection from degradation by serum nucleases in the matrix and thus has great potential as a mucosal gene delivery system. Chitosan also has many beneficial effects, including anticoagulant activity, wound-healing properties, and immunostimulatory activity, and is capable of modulating immunity of the mucosa and bronchus-associated lymphoid tissue. In one embodiment of the present invention, the vectors are conjugated with chitosan-derived nanoparticles.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA by the RNAi machinery or process. RSV "mRNA", "messenger RNA", and "transcript" each refer to single-stranded RNA that specifies the amino acid sequence of one or more RSV polypeptides. This information is translated during protein synthesis when ribosomes bind to the mRNA.

As used herein, the term "cleavage site" refers to the residues, e.g., nucleotides, at which RISC* cleaves the target RNA, e.g., near the center of the complementary portion of the target RNA, e.g., about 8-12 nucleotides from the 5' end of the complementary portion of the target RNA.

As used herein, the term "mismatch" refers to a basepair consisting of non-complementary bases, e.g., not normal complementary G:C, A:T or A:U base pairs.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized. Preferably, the NPRA inhibitors of the invention are administered in an isolated form.

As used herein, the term "in vitro" has its art recognized meaning, e.g., involving purified reagents or extracts, e.g., cell extracts. The term "in vivo" also has its art recognized meaning, e.g., involving living cells in an organism, e.g., immortalized cells, primary cells, and/or cell lines in an organism.

A gene "involved in" or "associated with" a disorder includes a gene, the normal or aberrant expression or function of which affects or causes a disease or disorder or at least one symptom of the disease or disorder. For example, NPRA protein has been found to have a significant role in pulmonary inflammation and immune modulation. Without being bound by theory, it has been found that signaling through the NPRA protein results in increased cGMP production and activation of protein kinase G, leading to regulation of transcription of many genes involved in the cell cycle, apoptosis, and inflammation. The polynucleotides, genetic constructs, pharmaceutical compositions, and methods of the invention are useful in decreasing expression of NPRA gene, in vitro or in vivo, consequently causing decreased production of the NPRA protein and decreased inflammation. Thus, the polynucleotides, genetic constructs, pharmaceutical compositions, and methods of the invention are useful in the treatment of human or non-human animal subjects suffering from, or at risk of developing, disorders associated with inflammation including, but not limited to, airway diseases, viral infections, and cancers.

The methods of the invention may include further steps. In some embodiments, a subject with the relevant condition or disease involving aberrant inflammation (e.g., asthma, RSV infection, cancers) is identified, or a subject at risk for the condition or disease is identified. A subject may be someone who has not been diagnosed with the disease or condition (diagnosis, prognosis, and/or staging) or someone diagnosed with the disease or condition (diagnosis, prognosis, monitoring, and/or staging), including someone treated for the disease or condition (prognosis, staging, and/or monitoring). Alternatively, the subject may not have been diagnosed with the disease or condition but suspected of having the disease or condition based either on patient history or family history, or the exhibition or observation of characteristic symptoms.

As used herein, an "effective amount" of a NPRA inhibitor (e.g., isatin or another oxindole, an siRNA, an antisense nucleotide sequence or strand, and/or a ribozyme), which selectively interferes with expression of the NPRA gene and/or function of the receptor, is that amount effective to bring about the physiological changes desired in the cells to which the polynucleotide is administered in vitro (e.g., ex vivo) or in vivo. The term "therapeutically effective amount" as used herein, means that amount of NPRA inhibitor (e.g., isatin or other oxindole, an siRNA, an antisense oligonucleotide, and/or a ribozyme), which selectively reduces expression of the NPRA gene(s) and/or function of the receptor, alone or in combination with another agent according to the particular aspect of the invention, that elicits the biological or medicinal response in cells (e.g., tissue(s)) that is being sought by a researcher, veterinarian, medical doctor or other clinician, which includes alleviation and/or prevention of the symptoms of the disease or disorder being treated. For example, a NPRA inhibitor can be administered to a subject in combination with other agents effective for alleviating or preventing the symptoms of inflammation, such as the gene expression vaccines (Mohapatra et al. 2004).

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

RNA Interference

RNAi is an efficient process whereby double-stranded RNA (dsRNA, also referred to herein as siRNAs or ds siRNAs, for double-stranded small interfering RNAs) induces the sequence-specific degradation of targeted mRNA in animal and plant cells (Hutvagner and Zamore, *Curr. Opin. Genet. Dev.*, 12:225-232 (2002); Sharp, *Genes Dev.*, 15:485-490 (2001). In mammalian cells, RNAi can be triggered by 21-nucleotide (nt) duplexes of small interfering RNA (siRNA) (Chiu et al., *Mol. Cell.*, 10:549-561 (2002); Elbashir et al., *Nature* 411:494-498 (2001), or by micro-RNAs (miRNA), functional small-hairpin RNA (shRNA), or other dsRNAs which can be expressed in vivo using DNA templates with RNA polymerase III promoters (Zeng et al., *Mol. Cell* 9:1327-1333 (2002); Paddison et al., *Genes Dev.* 16:948-958 (2002); Lee et al., *Nature Biotechnol.* 20:500-505 (2002); Paul et al., *Nature Biotechnol.* 20:505-508 (2002); Tuschl, T., *Nature Biotechnol.* 20:440-448 (2002); Yu et al., *Proc. Natl. Acad. Sci. USA* 99(9):6047-6052 (2002); McManus et al., *RNA* 8:842-850 (2002); Sui et al., *Proc. Natl. Acad. Sci. USA* 99(6):5515-5520 (2002).

Accordingly, the invention includes such molecules that are targeted to NPRA mRNAs encoding at least a portion of one or more of NPRA-like receptors.

siRNA Molecules

The nucleic acid molecules or constructs of the invention include dsRNA molecules comprising 16-30 nucleotides, e.g., 16, 17, 18, 19, 20, 21, 22, 23, 24, 25, 26, 27, 28, 29, or 30 nucleotides, in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA of the RSV mRNA, and the other strand is identical or substantially identical to the first strand. The dsRNA molecules of the invention can be chemically synthesized, or can be transcribed in vitro from a DNA template, or in vivo from, e.g., shRNA. The dsRNA molecules can be designed using any method known in the art, for instance, by using the following protocol:

1. Beginning with the AUG start codon, look for AA dinucleotide sequences; each AA and the 3' adjacent 16 or more nucleotides are potential siRNA targets. Further, siRNAs with lower G/C content (35-55%) may be more active than those with G/C content higher than 55%. Thus, in one embodiment, the invention includes polynucleotides having 35-55% G/C content. In addition, the strands of the siRNA can be paired in such a way as to have a 3' overhang of 1 to 4, e.g., 2, nucleotides. Thus, in another embodiment, the polynucleotides can have a 3' overhang of 2 nucleotides. The overhanging nucleotides can be either RNA or DNA.

2. Using any method known in the art, compare the potential targets to the appropriate genome database (human, mouse, rat, etc.) and eliminate from consideration any target sequences with significant homology to other coding sequences for which reduced expression is not desired. One such method for such sequence homology searches is known as BLAST, which is available at the National Center for Biotechnology Information web site of the National Institutes of Health.

3. Select one or more sequences that meet your criteria for evaluation. Further general information regarding the design and use of siRNA can be found in "The siRNA User Guide," available at the web site of the laboratory of Dr. Thomas Tuschl at Rockefeller University.

4. Negative control siRNAs preferably have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The polynucleotides of the invention can include both unmodified siRNAs and modified siRNAs as known in the art. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., *Drug Deliv. Rev.* 47(1): 99-112 (2001) (describes nucleic acids loaded to polyalkylcyanoacrylate (PACA) nanoparticles); Fattal et al., *J. Control Release* 53(1-3):137-43 (1998) (describes nucleic acids bound to nanoparticles); Schwab et al., *Ann. Oncol.* 5 Suppl. 4:55-8 (1994) (describes nucleic acids linked to intercalating agents, hydrophobic groups, polycations or PACA nanoparticles); and Godard et al., *Eur. J. Biochem.* 232(2):404-10 (1995) (describes nucleic acids linked to nanoparticles).

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER siRNA labeling kit (AMBION). Additionally, the siRNA can be radiolabeled, e.g., using $^{3}H$, $^{32}P$, or other appropriate isotope.

The dsRNA molecules of the present invention can comprise the following sequences as one of their strands, and the corresponding sequences of allelic variants thereof: SEQ ID NO:1 or SEQ ID NO:2.

Moreover, because RNAi is believed to progress via at least one single-stranded RNA intermediate, the skilled artisan will appreciate that ss-siRNAs (e.g., the antisense strand of a ds-siRNA) can also be designed as described herein and utilized according to the claimed methodologies.

siRNA Delivery for Longer-Term Expression

Synthetic siRNAs can be delivered into cells by methods known in the art, including cationic liposome transfection and electroporation. However, these exogenous siRNA generally show short-term persistence of the silencing effect (4 to 5 days in cultured cells), which may be beneficial in certain embodiments. To obtain longer term suppression of RSV gene expression and to facilitate delivery under certain circumstances, one or more siRNA duplexes, e.g., RSV ds siRNA, can be expressed within cells from recombinant DNA constructs. Such systems for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., *J. Cell. Physiol.* 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella et al. (1998), supra; Lee et al. (2002), supra; Miyagishi et al. (2002), supra; Paul et al. (2002), supra; Yu et al. (2002), supra; Sui et al. 2002) supra). Constructs containing siRNA sequence(s) under the control of a T7 promoter also make functional siRNAs when co-transfected into the cells with a vector expressing T7 RNA polymerase (Jacque (2002), supra). A single construct may contain multiple sequences coding for siRNAs, such as multiple regions of the RSV NS1 mRNA and/or other RSV genes, and can be driven, for example, by separate PolIII promoter sites.

Animal cells express a range of non-coding RNAs of approximately 22 nucleotides termed micro RNA (miRNAs) that can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., *Proc. Natl. Acad. Sci. USA* 99(22):14236-40 (2002)). In adult mice, efficient delivery of siRNA can be accomplished by the "high-pressure" delivery technique, a rapid injection (within 5 seconds) of a large volume of siRNA-containing solution into animal via the tail vein (Liu (1999), supra; McCaffrey (2002), supra; Lewis, *Nature Genetics* 32:107-108 (2002)). Nanoparticles and liposomes can also be used to deliver siRNA into animals.

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the RSV protein (such as RSV NS1 protein) encoded by that mRNA in the cell or organism. The RNA precursors are typically nucleic acid molecules that individually encode either one strand of a dsRNA or encode the entire nucleotide sequence of an RNA hairpin loop structure.

Antisense

An "antisense" nucleic acid sequence (antisense oligonucleotide) can include a nucleotide sequence that is complementary to a "sense" nucleic acid sequence encoding a protein, e.g., complementary to the coding strand of a double-stranded cDNA molecule or complementary to at least a portion of an RSV gene. The antisense nucleic acid sequence can be complementary to an entire coding strand of a target sequence, or to only a portion thereof (for example, the RSV NS1 gene and/or RSV NS2 gene, or a portion of either or both). In another embodiment, the antisense nucleic acid molecule is antisense to a "noncoding region" of the coding strand of a nucleotide sequence within the RSV gene. An antisense oligonucleotide can be, for example, about 7, 10, 15, 20, 25, 30, 35, 40, 45, 50, 55, 60, 65, 70, 75, 80, or more nucleotides in length.

An antisense nucleic acid sequence can be designed such that it is complementary to the entire RSV gene, but can also be an oligonucleotide that is antisense to only a portion of the RSV gene. For example, the antisense oligonucleotide can be complementary to the region surrounding the translation start site of the target mRNA, e.g., between the −10 and +10 regions of the target gene nucleotide sequence of interest. An antisense oligonucleotide sequence can be, for example, about 7, 10, 15, 20, 25, 30, 35, 40, 45, 50, 55, 60, 65, 70, 75, 80, or more nucleotides in length.

An antisense nucleic acid sequence of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid sequence also can be produced biologically using an expression vector into which a nucleic acid sequence has been subcloned in an antisense orientation (i.e., RNA transcribed from the inserted nucleic acid sequence will be of an antisense orientation to a target nucleic acid sequence of interest, described further in the following subsection).

The antisense nucleic acid molecules of the invention are typically administered to a subject (e.g., systemically or locally by direct injection at a tissue site), or generated in situ such that they hybridize with or bind to RSV mRNA to thereby inhibit expression of the viral protein. Alternatively, antisense nucleic acid molecules can be modified to target selected cells (such as respiratory epithelial cells, dendritic cells, and/or monocytes) and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense oligonucleotide of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.,* 215:327-330 (1987)).

Gene expression can be inhibited by targeting nucleotide sequences complementary to the regulatory region of the gene to form triple helical structures that prevent expression of the gene in target cells. See generally, Helene, C. *Anticancer Drug Des.* 6:569-84 (1991); Helene, C. *Ann. N.Y. Acad. Sci.* 660:27-36 (1992); and Maher, *Bioassays* 14:807-15 (1992). The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme encoding nucleotide sequences can be introduced into cells through gene-delivery mechanisms known in the art. A ribozyme having specificity for RSV RNA can include one or more sequences complementary to the nucleotide sequence of at least a portion of one or more RSV mRNA (e.g., RSV NS1 mRNA), and a sequence having known catalytic sequence responsible for mRNA cleavage (see U.S. Pat. No. 5,093,246 or Haselhoff and Gerlach *Nature* 334:585-591 (1988)). For example, a derivative of a Tetrahymena L-19 IVS RNA can be constructed in which the nucleotide sequence of the active site is complementary to the nucleotide sequence to be cleaved in the RSV mRNA, such as RSV NS1 mRNA (see, e.g., Cech et al. U.S. Pat. No. 4,987,071; and Cech et al. U.S. Pat. No. 5,116,742). Alternatively, RSV mRNA encoding an RSV protein can be used to select a catalytic RNA having a specific ribonuclease activity from a pool of RNA molecules (see, e.g., Bartel, D. and Szostak, J. W. *Science* 261:1411-1418 (1993)).

Nucleic Acid Targets

The nucleic acid targets of the polynucleotides of the invention (e.g., antisense, RNAi, and ribozymes) may be ANP receptor gene, or a portion thereof, such as NPRA, NPRB or NPRC or portion of any of the foregoing. In some embodiments, the nucleic acid target is the NPRA gene, or a portion thereof. The nucleic acid target may be any location within the NPRA or transcript. Preferably, the nucleic acid target is located at a site selected from the group consisting of the 5' untranslated region (UTR), transcription start site, translation start site, and the 3' UTR.

The nucleic acid target may be located within a NPRA gene of any human or mammal. Preferably, the nucleic acid target is at least a portion of a non-structural NPRA gene. More preferably, the nucleic acid target is at least a portion of an NPRA gene encoding a protein. In a particularly preferred embodiment, the nucleic acid target is located within an NPRA that normally down-regulates host inflammation. In another preferred embodiment, the nucleic acid target is located within the human NPRA or mammalian NPRA, selected from the group consisting of the 5' untranslated region (UTR), transcription start site, translation start site, and the 3' UTR.

The nucleic acid target may be located within a human NPRA gene (NCBI accession no. AF190631, which is incorporated herein by reference in its entirety) or an ortholog thereof, such as a non-human, mammalian NPRA gene. For treating and/or preventing inflammation within a particular subject, the polynucleotide selected for administration to the subject is preferably one targeted to a NPRA gene. For example, for treating and/or preventing inflammation within a human subject, the nucleic acid target is preferably located within a human NPRA gene, or the nucleic acid target has sufficient homology with the human NPRA gene, so as to reduce expression of the human NPRA gene. The term "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%. 91%, 92%, 93%, 94%, 95%, 96%, 97%, 98% or 99% identity are defined herein as substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, at least 60%, at least 70%, at least 80%, at least 90%, at least 95%, or at least 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* 48:444-453 (1970)) algorithm, which has been incorporated into the GAP program in the GCG software package (available at the official Accelrys web site), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at the official Accelrys web site), using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*CABIOS,* 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other orthologs, e.g., family members or related sequences. Such searches can be performed using the NBLAST and XBLAST programs (version 2.0) of Altschul, et al. *J. Mol. Biol.* 215:403-10 (1990). BLAST nucleotide searches can be performed with the NBLAST program, score=100, word length=12, to obtain nucleotide sequences homologous to known RSV DNA and RNA sequences. BLAST protein searches can be performed with the XBLAST program, score=50, word length=3, to obtain amino acid sequences homologous to known RSV polypeptide products. To obtain gapped alignments for comparison purposes, Gapped BLAST can be utilized as described in Altschul et al., *Nucleic Acids Res.* 25:3389-3402 (1997). When utilizing BLAST and Gapped BLAST programs, the default parameters of the respective programs (e.g., XBLAST and NBLAST) can be used (see the National Center for Biotechnology Information web site of the National Institutes of Health).

Orthologs can also be identified using any other routine method known in the art, such as screening a cDNA library, e.g., using a probe designed to identify sequences that are substantially identical to a reference sequence.

Pharmaceutical Compositions and Methods of Administration

The NPRA inhibitors of the subject invention (e.g., isatin or other oxindols, siRNA molecules, antisense molecules, and ribozymes) can be incorporated into pharmaceutical compositions. Such compositions typically include the polynucleotide and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Formulations (compositions) are described in a number of sources that are well known and readily available to those skilled in the art. For example, *Remington's Pharmaceutical Sciences* (Martin E. W., Easton Pa., Mack Publishing Company, 19$^{th}$ ed., 1995) describes formulations which can be used in connection with the subject invention.

A pharmaceutical composition is formulated to be compatible with its intended route of administration. Examples of routes of administration include parenteral, e.g., intravenous, intradermal, subcutaneous, oral (e.g., inhalation), nasal, topical, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as mannitol, sorbitol, sodium chloride can also be included in the composition. Prolonged absorption of the injectable compositions can be brought about by including in the composition an agent that delays absorption, such as aluminum monostearate or gelatin.

Sterile injectable solutions can be prepared by incorporating the active compound (e.g., a polynucleotide of the invention) in the required amount in an appropriate solvent with one or a combination of ingredients enumerated above, as required, followed by filtered sterilization. Generally, dispersions are prepared by incorporating the polynucleotide into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the NPRA inhibitors can be delivered in the form of drops or an aerosol spray from a pressured container or dispenser that contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, drops, or suppositories. For transdermal administration, the active compound (e.g., polynucleotides of the invention) are formulated into ointments, salves, gels, or creams, as generally known in the art.

The pharmaceutical compositions can also be prepared in the form of suppositories (e.g., with conventional suppository bases such as cocoa butter and other glycerides) or retention enemas for rectal delivery.

In embodiments in which the NPRA inhibitor is a polynucleotide, the polynucleotides can be administered by transfection or infection using methods known in the art, including but not limited to, the methods described in McCaffrey et al., *Nature* 418(6893):38-39 (2002) (hydrodynamic transfection); Xia et al., *Nature Biotechnol.* 20(10):1006-10 (2002) (viral-mediated delivery); or Putnam, *Am. J. Health Syst. Pharm.* 53(2):151-160 (1996), erratum at *Am. J. Health Syst. Pharm.* 53(3):325 (1996).

The polynucleotides can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al., *Clin. Immunol. Immunopathol.* 88(2):205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996). Preferably, the polynucleotides of the invention are administered to the subject such that an effective amount are delivered to the respiratory epithelial cells, DC, and/or monocytes within the subject's airway, resulting in an effective amount of reduction in NPRA gene expression.

In one embodiment, the polynucleotides are prepared with carriers that will protect the polynucleotide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. These can be prepared according to methods known to those skilled in the art, for example, as described in U.S. Pat. No. 4,522,811.

Preferably, the NPRA inhibitors of the subject invention (e.g., compositions containing them) are administered locally or systemically such that they are delivered to target cells, such as cells of the airway, e.g., airway epithelial cells, which line the nose as well as the large and small airways. For some disorder, it is preferred that the NPRA inhibitors of the invention be delivered to dendritic cells and/or monocytes.

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the method of the invention, the therapeutically effective dose can be estimated initially from cell culture assays. A dose can be formulated in animal models to achieve a circulating plasma concentration range that includes the IC50 (i.e., the concentration of the test composition which achieves a half-maximal inhibition of symptoms) as determined in cell culture. Such information can be used to more accurately determine useful doses in humans. Levels in plasma can be measured, for example, by high performance liquid chromatography.

The compositions of the invention can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a NPRA inhibitor can include a single treatment or can include a series of treatments.

Mammalian species that benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. As used herein, the terms "subject", "host", and "patient" are used interchangeably and intended to include such human and non-human mammalian species. Likewise, in vitro methods of the present invention can be carried out on cells of such mammalian species. Host cells comprising exogenous polynucleotides of the invention may be administered to the subject, and may, for example, be autogenic (use of one's own cells), allogenic (from one person to another), or transgenic or xenogenic (from one species to another), relative to the subject.

The polynucleotides of the invention can be inserted into genetic constructs, e.g., viral vectors, retroviral vectors, expression cassettes, or plasmid viral vectors, e.g., using methods known in the art, including but not limited to those described in Xia et al., (2002), supra. Genetic constructs can be delivered to a subject by, for example, inhalation, orally, intravenous injection, local administration (see U.S. Pat. No. 5,328,470) or by stereotactic injection (see, e.g., Chen et al., Proc. Natl. Acad. Sci. USA 91:3054-3057 (1994)). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

The polynucleotides of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., Science 296:550-553 (2002); Lee et al., (2002), supra; Miyagishi and Taira, Nature Biotechnol. 20:497-500 (2002); Paddison et al. (2002), supra; Paul (2002), supra; Sui (2002) supra; Yu et al. (2002), supra.

SiRNAs of the invention may be fused to other nucleotide molecules, or to polypeptides, in order to direct their delivery or to accomplish other functions. Thus, for example, fusion proteins comprising a siRNA oligonucleotide that is capable of specifically interfering with expression of NPRA gene may comprise affinity tag polypeptide sequences, which refers to polypeptides or peptides that facilitate detection and isolation of the polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al., (Bio/Technology 6:1204, 1988), or the XPRESS epitope tag (INVITROGEN, Carlsbad, Calif.). The affinity sequence may be a hexa-histidine tag as supplied, for example, by a pBAD/His (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 Cell 37:767).

The present invention also relates to vectors and to constructs that include or encode polynucleotides of the present invention (e.g., siRNA), and in particular to "recombinant nucleic acid constructs" that include any nucleic acid such as a DNA polynucleotide segment that may be transcribed to yield NPRA mRNA-specific siRNA polynucleotides according to the invention as provided above; to host cells which are genetically engineered with vectors and/or constructs of the invention and to the production of siRNA polynucleotides, polypeptides, and/or fusion proteins of the invention, or fragments or variants thereof, by recombinant techniques. siRNA sequences disclosed herein as RNA polynucleotides may be engineered to produce corresponding DNA sequences using well-established methodologies such as those described herein. Thus, for example, a DNA polynucleotide may be generated from any siRNA sequence described herein, such that the present siRNA sequences will be recognized as also providing corresponding DNA polynucleotides (and their complements). These DNA polynucleotides are therefore encompassed within the contemplated invention, and can, for example, be incorporated into the subject invention recombinant nucleic acid constructs from which siRNA may be transcribed.

According to the present invention, a vector may comprise a recombinant nucleic acid construct containing one or more promoters for transcription of an RNA molecule, for example, the human U6 snRNA promoter (see, e.g., Miyagishi et al., Nat. Biotechnol. 20:497-500 (2002); Lee et al., Nat. Biotechnol. 20:500-505 (2002); Paul et al., Nat. Biotechnol. 20:505-508 (2002); Grabarek et al., BioTechniques 34:73544 (2003); see also Sui et al., Proc. Natl. Acad. Sci. USA 99:5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for an RSV sequence may be transcribed under the control of a single promoter such that the siRNA polynucleotide forms a hairpin molecule (Paul et al., supra). In such an instance, the complementary strands of the siRNA specific sequences are separated by a spacer that comprises at least four nucleotides, but may comprise at least 5, 6, 7, 8, 9, 10, 11, 12, 14, 16, 94 18 nucleotides or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., Science 296:550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

Polynucleotides of the invention can be expressed in mammalian cells, yeast, bacteria, or other cells under the control of appropriate promoters, providing ready systems for evaluation of NPRA polynucleotides that are capable of interfering with expression of NPRA gene, as provided herein. Appropriate cloning and expression vectors for use with prokaryotic and eukaryotic hosts are described, for example, by Sambrook, et al., Molecular Cloning: A Laboratory Manual, Third Edition, Cold Spring Harbor, N.Y., (2001).

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (2001 Molecular Cloning, Third Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control sequences (e.g., a promoter or a regulated promoter) to direct mRNA synthesis. Representative examples of such expression control sequences include LTR or SV40 promoter, the E. coli lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter, or regulated promoter, operably linked to a polynucleotide of the invention is described herein.

As noted above, in certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters that may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above. A tissue-specific promoter allows preferential expression of the polynucleotide in a given target tissue (such as tissue of the respiratory tract), thereby avoiding expression in other tissues. For example, to express genes specifically in the heart, a number of cardiac-specific regulatory elements can be used. An example of a cardiac-specific promoter is the ventricular form of MLC-2v promoter (see, Zhu et al., *Mol. Cell. Biol.* 13:4432-4444, 1993; Navankasattusas et al., *Mol. Cell Biol.* 12:1469-1479, 1992) or a variant thereof such as a 281 bp fragment of the native MLC-2v promoter (nucleotides −264 to +17, Genebank Accession No. U26708). Examples of other cardiac-specific promoters include alpha myosin heavy chain (Minamino et al., *Circ. Res.* 88:587-592, 2001) and myosin light chain-2 (Franz et al., *Circ. Res.* 73:629-638, 1993). Endothelial cell gene promoters include endoglin and ICAM-2. See Velasco et al., *Gene Ther.* 8:897-904, 2001. Liver-specific promoters include the human phenylalanine hydroxylase (PAH) gene promoters (Bristeau et al., *Gene* 274:283-291, 2001), hB1F (Zhang et al., *Gene* 273:239-249, 2001), and the human C-reactive protein (CRP) gene promoter (Ruther et al., *Oncogene* 8:87-93, 1993). Promoters that are kidney-specific include CLCN5 (Tanaka et al., *Genomics* 58:281-292, 1999), renin (Sinn et al., *Physical Genomics* 3:25-31, 2000), androgen-regulated protein, sodium-phosphate cotransporter, renal cytochrome P-450, parathyroid hormone receptor and kidney-specific cadherin. See *Am. J. Physiol. Renal Physiol.* 279:F383-392, 2000. An example of a pancreas-specific promoter is the pancreas duodenum homeobox 1 (PDX-1) promoter (Samara et al., *Mol. Cell Biol.* 22:4702-4713, 2002). A number of brain-specific promoters may be useful in the invention and include the thy-1 antigen and gamma-enolase promoters (Vibert et al., *Eur. J. Biochem.* 181:33-39, 1989), the glial-specific glial fibrillary acidic protein (GFAP) gene promoter (Cortez et al., *J. Neurosci. Res.* 59:39-46, 2000), and the human FGF1 gene promoter (Chiu et al., *Oncogene* 19:6229-6239, 2000). The GATA family of transcription factors have promoters directing neuronal and thymocyte-specific expression (see Asnagli et al., *J. Immunol.* 168:4268-4271, 2002).

In another aspect, the present invention relates to host cells containing the above described recombinant constructs. Host cells are genetically engineered/modified (transduced, transformed or transfected) with the vectors and/or expression constructs of this invention that may be, for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo.

Various mammalian cell culture systems can also be employed to produce polynucleotides of the invention from recombinant nucleic acid constructs of the present invention. The invention is therefore directed in part to a method of producing a polynucleotide, such as a siRNA, by culturing a host cell comprising a recombinant nucleic acid construct that comprises at least one promoter operably linked to a polynucleotide of the invention that is specific for NPRA gene. In certain embodiments, the promoter may be a regulated promoter as provided herein, for example a tetracycline-repressible promoter. In certain embodiments, the recombinant expression construct is a recombinant viral expression construct as provided herein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAE-Dextran mediated transfection, or electroporation (Davis et al., 1986 Basic Methods in Molecular Biology), or other suitable technique.

The expressed polynucleotides may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

As used herein, the terms "administer", "apply", "treat", "transplant", "implant", "deliver", and grammatical variations thereof, are used interchangeably to provide NPRA inhibitors of the subject invention (e.g., vectors containing or encoding polynucleotides of the subject invention) to target cells in vitro or in vivo, or provide genetically modified (engineered) cells of the subject invention to a subject ex vivo.

As used herein, the term "co-administration" and variations thereof refers to the administration of two or more agents simultaneously (in one or more preparations), or consecutively. For example, one or more types of NPRA inhibitors of the invention (e.g., vectors containing or encoding polynucleotides of the subject invention) can be co-administered with other agents.

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence" includes more than one such sequence. A reference to "a cell" includes more than one such cell.

The terms "comprising", "consisting of" and "consisting essentially of" are defined according to their standard meaning. The terms may be substituted for one another throughout the instant application in order to attach the specific meaning associated with each term.

EXAMPLE 1

ANP Overexpression in the Lung Augments Inflammation and Cytokine Production in Splenocytes ANP has been suspected to play a role in decreasing inflammation, as it was shown to play a role in decreasing TNF-α production from macrophages and slightly decreased NFkB activation (Mohapatra et al. JACI, 2004). Also, NPRA deficient mice did not exhibit inflammation. Since excess ANP expression activates the clearance receptor, it was hypothesized that ANP actually increases inflammation. To test this, naïve mice were administered intranasally a plasmid pVAX expressing the ANP peptide. The results show that ANP overexpression actually increases inflammation.

Materials and Methods

Animals. Six-week old female BALB/c mice from Jackson laboratory (Bar Harbor, Me.) were maintained in pathogen free conditions in accordance with animal research committee regulations.

Construction of ANP expression vector. Total RNA was isolated from murine heart using Trizol reagent (LIFE TECHNOLOGY, Gaithersburg, Md.) following the manufacturer's protocol. The cDNA sequence for the ANP, residues 99-126 of pro ANP was amplified by RT-PCR. A translation initiation codon was inserted in the forward primers, so that the recombinant peptides had an additional amino acid, methionine, as the first amino acid apart from its known content. The PCR product was cloned in pVAX vector (INVITROGEN, Carlsbad, Calif.) at HindIII and XhoI sites. The cloned ANP sequence was verified by DNA sequencing and its expression was checked in A549 human epithelial cells.

Analysis of intracellular cytokine production in T cells. Mouse spleen T cells purified using mouse T-cell enrichment column kit (R & D Systems, Minneapolis, Minn.) were cultured in 6-well plates for 4 days. Finally, cells were stimulated with PMA (50 ng/ml) and ionomycin (500 ng/ml) (SIGMA, Saint Louis, Mo.) for 6 hours in the presence of GOLGISTOP (PHARMINGEN, San Diego, Calif.) and then fixed and stained using CD8 or CD4 mAb (BD BIOSCIENCES, San Diego, Calif.) for flow cytometry analysis.

Histological analysis. Mouse lungs were removed after 24 hours of intranasal pANP administration, fixed, and sections stained with H&E.

Results. Normal BALB/c mice were given i.n. nanoparticles carrying pANP or pVAX and their lungs were examined 3 days after by staining the sections (H&E), showing goblet cell hyperplasia. These results directly demonstrate that in normal mice over expression of ANP results in bronchial inflammation. To demonstrate that ANP over expression also stimulates immune system, BALB/c mice were given i.p. OVA (with alum) and then challenged i.n. OVA. Mice were sacrificed, the spleens aseptically removed and the cells were cultured for 48 hours in the presence of OVA (Sigma) and recombinant IL-2. Cells were removed from culture and stained for surface markers CD4 and CD3 and intracellular cytokines IL-4, IL-10 and IFN-g (BD Pharmingen). The results show that in normal mice in absence of any antigen sensitization, ANP overexpression increases expression of boANP in general augments inflammation by activating both innate and adaptive immunity.

EXAMPLE 2

Inhibitory Effect of Transfected siRNA Plasmids on NPRA Expression

To determine whether siRNAs can be produced that will effectively decrease NPRA expression, 11 different siRNA oligos were designed and cloned in a pU6 vector. Cells transfected with each of the construct was examined for NPRA protein expression by western blotting.

Materials and Methods

Plasmid constructs. The nucleotide sequence for each siRNA is described previously (SEQ ID #1-11). Each pair of oligos was inserted into pU6 plasmid at appropriate sites respectively, to generate the corresponding siRNA for siNPRA.

DNA transfection. Cells were transfected with siNPRA or controls (siU6) using LIPOFECTAMINE 2000 reagent (INVITROGEN, Carlsbad, Calif.). pEGFP plasmid (STRATAGENE, La Jolla, Calif.) was used for measurement of transfection efficiency.

Protein expression analysis by Western blotting. Transfected cells were used to prepare whole cell lysates, which were electrophoresed on 12% polyacrylamide gels and the proteins were transferred to PVDF membranes (BIO-RAD, Hercules, Calif.). The blot was incubated separately with NPRA polyclonal antibody (SANTA CRUZ BIOTECH, Santa Cruz, Calif.), immunoblot signals were developed by SUPER SIGNAL ULTRA chemiluminescent reagent (PIERCE, Rockford, Ill.).

Figure 2:
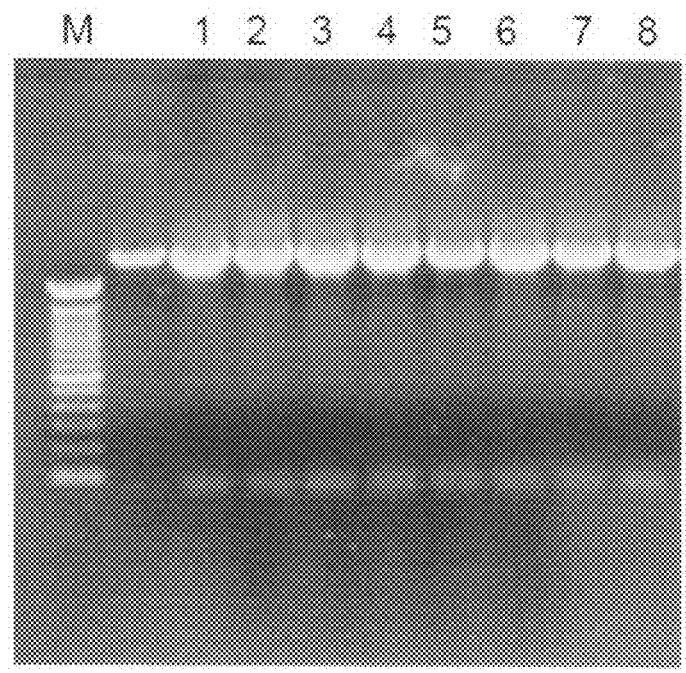
FIG. 2 shows cloning of siNPRA sequences in the pU6 vector. The siNPRA sequences were designed as shown in Sequence IDs and cloned in pSilencer 1 (U6) vector using standard procedures. The transformants were tested by digestion with Apa I and EcoR I to release the siRNA inserts. Lane1, 100 bp ladder; lane 2:pSilencer1 (U6), Lane3-6, siNPRA8, Lane7-10, siNPRA9 are shown for illustration.
Figure 3C:
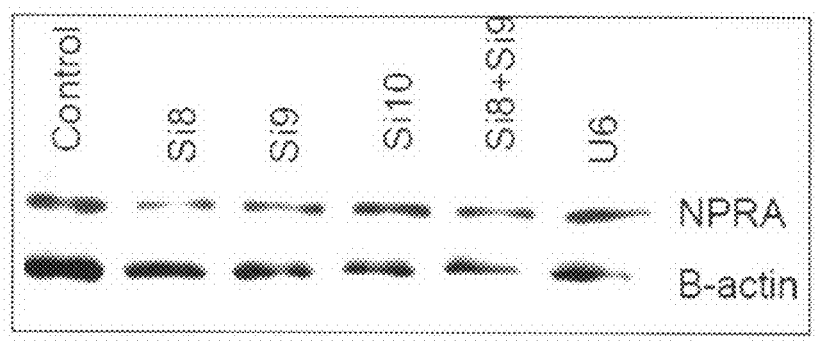
FIGS. 3 A-3C show the inhibitor y effect of transfected siRNA plasmids on NPRA expression. HEKGCA cells grown in 6-well plates were transfected with psiNPRA (2 ug). Forty eight hours later, total protein was extracted and Western blotted using an antibody to NPRA. Plasmids encoding ANP, Kp73-102 and VD were used as controls, since they have been shown to downregulate NPRA expression. In the third experiment, HEKGCA cells grown in 6-well plates were transfected with psiNPRA (2 ug), as indicated and forty eight hours later total protein were extracted western blotted using an antibody to NPRA (FIG. 3C). Untransfected cells and cells transfected with U6 vector plasmid without any siNPRA were used as control. Also, filters were stripped and reprobed with antibody to beta-actin.
Figure 3A:
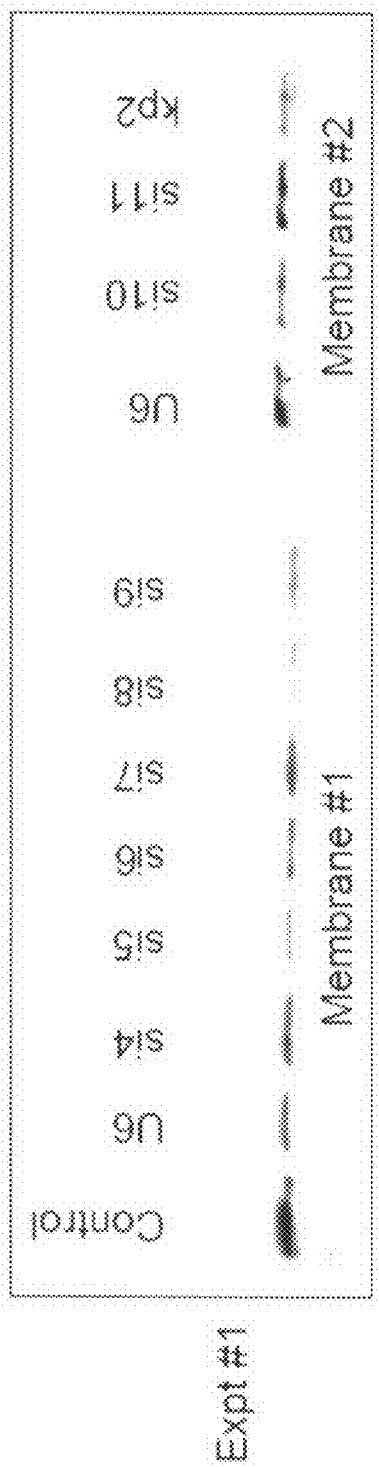
Figure 3B:
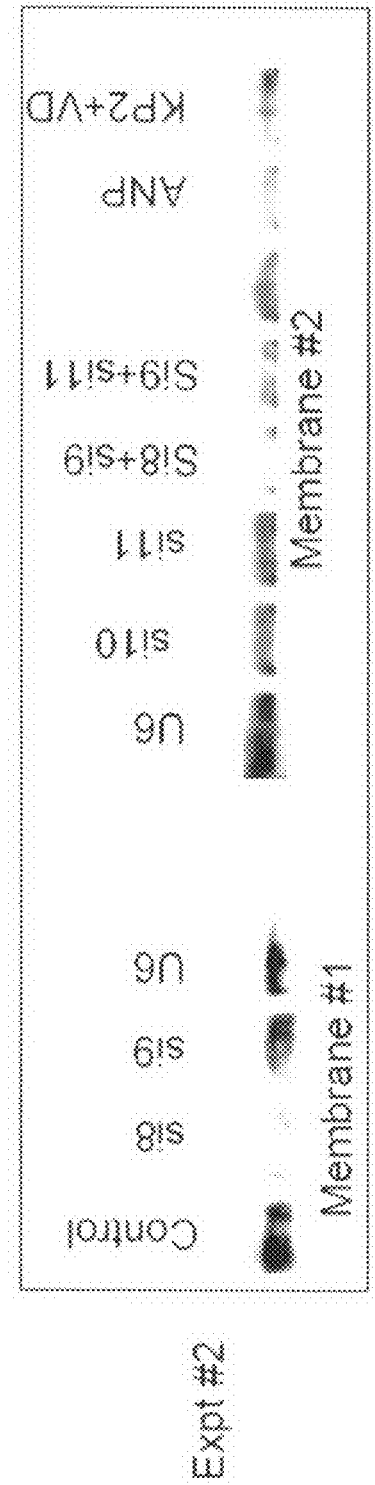

Results. Eleven different siRNA oligos were designed specifically targeting NPRA gene. The siRNA oligos were cloned in pU6 vector. FIG. 2 shows results the inserts being present in the plasmids. The inserts were sequenced to confirm the presence of siRNA inserts in them. Cells in 6-well plates were transfected with psiNPRA (2 ug). Forty eight hours later total protein were extracted western blotted using an antibody to NPRA. Results from two different experiments are shown in FIGS. 3A-3C. Plasmids encoding ANP, Kp73-102 and VD were used as control, since they have been shown to downregulate NPRA expression. In the third experiment, HEKGCA cells grown in 6-well plates were transfected with psiNPRA (2 ug), as indicated and forty eight hours later total protein were extracted western blotted using an antibody to NPRA (FIG. 3C). Untransfected cells and cells transfected with U6 vector plasmid without any siNPRA were used as control. Also, filters were stripped and reprobed with antibody to beta-actin. The experiments were repeated. The results showed that 3 of 11 siNPRA constructs consistently decreased NPRA protein expression in the HEKGCA cells.

Figures 4A, 4B:
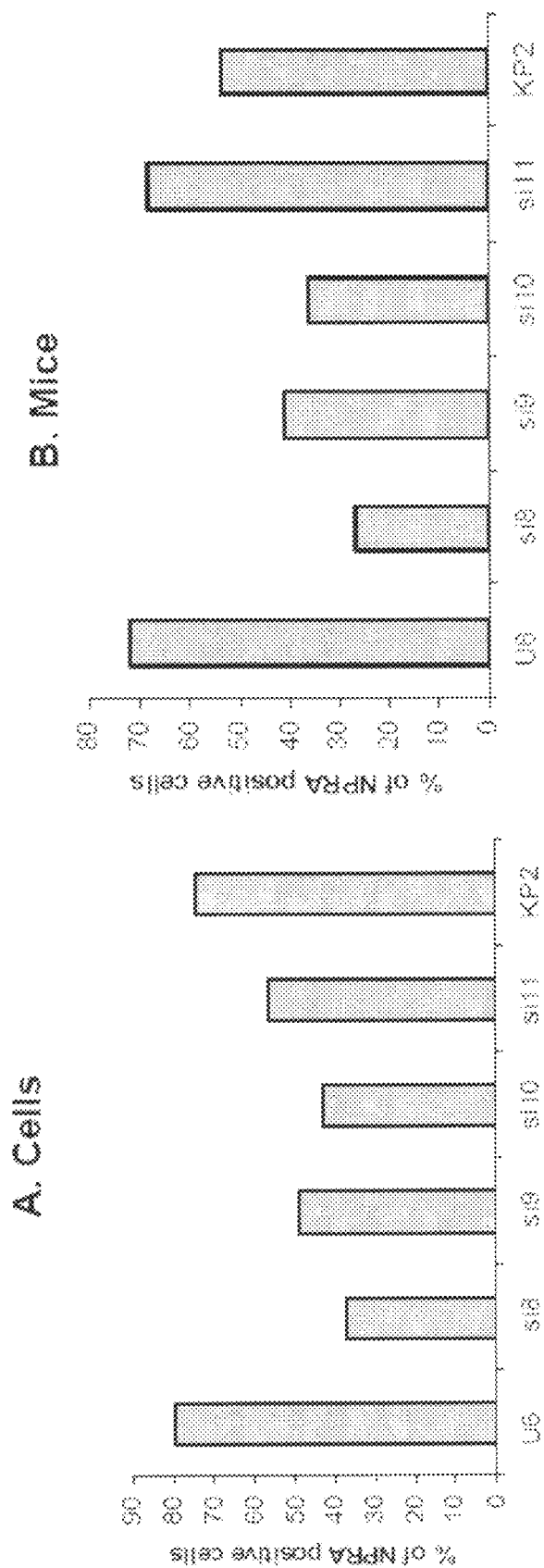
FIGS. 4A and 4B show inhibitory effect of siRNA in vitro and in vivo. HEKGCA cells grown in 6-well plates were transfected with psiNPRA (2 ug). Forty eight hours later, cells were subjected to flow cytometry to detect NPRA positive cells using an antibody to NPRA. U6 plasmid without any siRNA and plasmid encoding Kp73-102 were used as controls, since the latter has been shown to downregulate NPRA expression. Results are shown in FIG. 4A. Mice (n=4) were intranasally administered with 25 ug siRNA plasmids complexed with 125 ul of chitosan nanoparticles. BAL was done 72 hours later. Cells were stained by NPRA Ab. NPRA expression cells were counted.

To confirm these results, inhibitory effect of siRNA in vitro was examined using HEKGCA cells. Cells grown in 6-well plates were transfected with psiNPRA (2 ug). Forty eight hours later, cells were subjected to flow cytometry to detect NPRA positive cells using an antibody to NPRA (FIG. 4A). U6 plasmid without any siRNA and Plasmid encoding Kp73-102 was used as controls, since the latter has been shown to down-regulate NPRA expression. B) Mice (n=4) were intranasally administered with 25 ug siRNA plasmids complexed with 125 ul of chitosan nanoparticles. BAL was done 72 hours later. Cells were stained by NPRA Ab. NPRA expression cells were counted (FIG. 4B).

Together the results show that siNPRA8, siNPRA9 and siNR10 were the most effective siRNAs that significantly reduced NPRA expression.

EXAMPLE 3

Demonstration that Oral siNPRA Treatment Decreases Inflammation, Eosinophilia and Th2 Cytokines in BALB/c Mice To determine whether decreased expression of NPRA by siNPRA treatment will reduce inflammation in asthma, the effect of intranasal siNPRA9 was tested in ovalbumin-induced mouse model of asthma.

Materials and Methods. Six to eight week-old BALB/c mice (n=6) were sensitized by i.p. injection of ovalbumin (50 ug in 2 mg of alum/mouse) and challenged intranasally with OVA (50 µg). Mice were given two siNPRA9 treatments by gavage and challenged 24 hours later. After a further 24 hours of challenge, mice were sacrificed and their lungs removed for histology in a subgroup (n=3) of mice. The remainder of the group were lavaged and a cell differential was performed as described, especially to enumerate the eosinophil numbers in the BAL fluid. Thoracic lymph node cells (A) and spleen cells (B) were removed and cells cultured for 48 hours in the presence of OVA (Sigma Grade V) and recombinant mouse IL-2. Naïve mice received no treatment. Cells were treated with GolgiStop (BD Pharmingen) and stained for surface and intracellular cytokines (Antibodies obtained from BD Pharmingen). Percent cytokine secreting cells were quantified by intracellular cytokine staining using flow cytometry, as described.

Figures 1, 2, 5A, 5B:
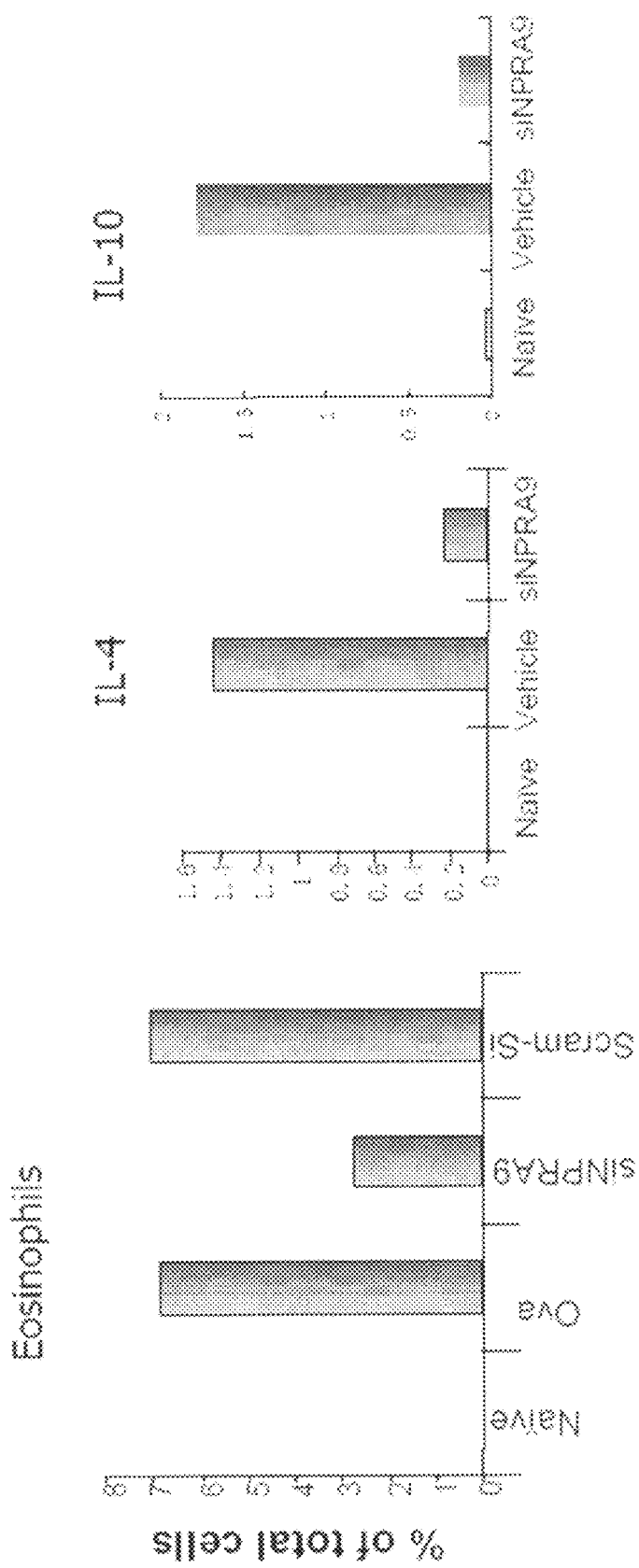
Figure 6A:
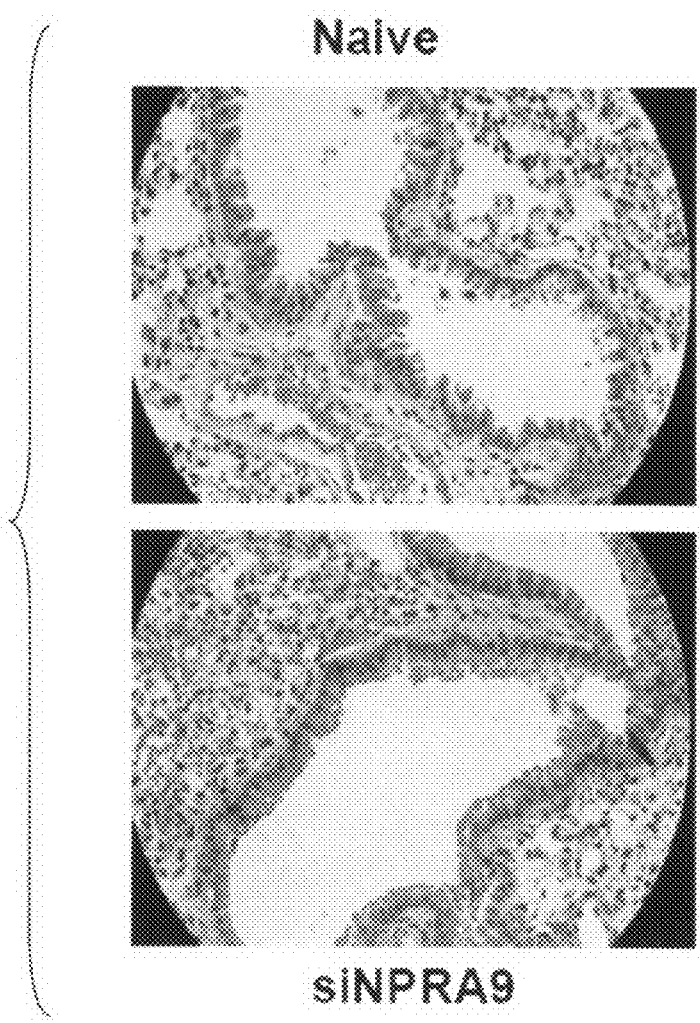
FIGS. 6A and 6B show that administration of siNPRA decreases inflammation of the lung in BALB/c mice. 4-6 week old BALB/c mice (n=3) were sensitized and challenged with OVA (50 µg). All mice were sensitized intra-peritoneally (i.p.) and then challenged intranasally (i.n.). Mice were given two Si NPRA treatments by gavage and challenged 24 hours later. Lungs were obtained 24 hours after challenge, fixed in formalin, sectioned and stained with hematoxylin and eosin.
Figure 6B:
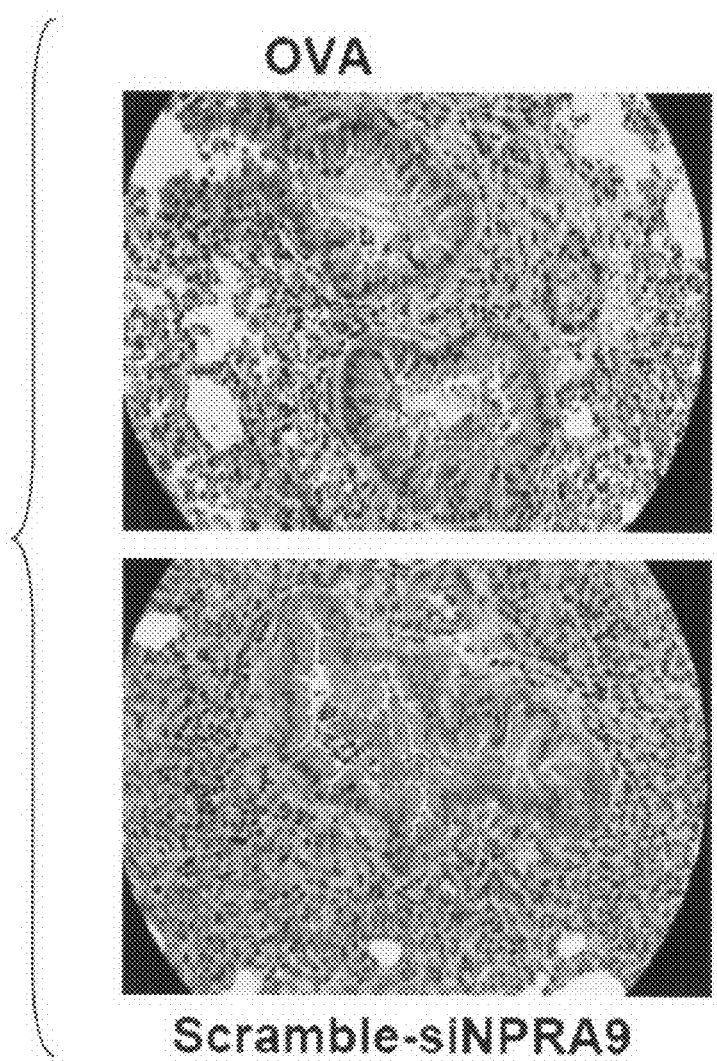

Results. The results of lung histology, i.e., lung sections stained by H &E revealed that compared to untreated Ovalbumin-sensitized and mice treated with scrambled si-NPRA group, treated mice showed a significant reduction in lung inflammation. The lung histology was very similar to the naïve mice. There was significant reduction in epithelial goblet cell hyperplasia and a significant reduction in peribroncial, perivascular and interstitial infiltration of the inflammatory cells to the lung (FIGS. 6A-6C). There was also a significant reduction in the number of eosinophils in BAL fluid (FIG. 5A) and reduction in Th2 cytokines in thoracic lymph nodes as determined by intracellular cytokine staining (FIGS. 5B-1 and 5B-2).

EXAMPLE 4

Demonstration that Transdermal siNPRA Treatment Decreases Inflammation, Eosinophilia and Th2 Cytokines in BALB/c Mice Patients are more compliant when the drug is delivered by transdermal route. Therefore, siNPRA8 delivered by transdermal route was attempted to determine whether such siRNA therapy would decrease pulmonary inflammation in this ovalbumin-induced mouse model of asthma.

Materials and Methods. BALB/c mice (n=5 each group) were sensitized (i.p.) as in example #3 and challenged (i.n.) with 50 µg of OVA. Mice were given siNPRA (oligonucleotide) treatments by transdermal route (siNPRA8) and challenged 4 hours later. Following 24 hours of challenge two mice were sacrificed to obtain lungs and which were fixed sectioned and immunostained for NPRA expression (A). Mice (n=3) were sacrificed and lavaged and the percentage of eosinophils (B) and IL-4 concentration (C) in the lavage fluid was determined.

Figure 7A:
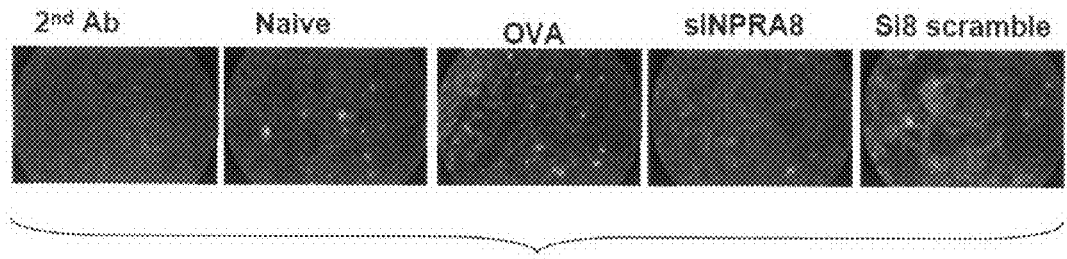
FIGS. 7A-7C show that administration of siNPRA8 by the transdermal route decreases NPRA expression, eosinophilia of the lung and BAL IL-4 cytokine. BALB/c mice (n=5 each group) were sensitized (i.p.) and challenged (i.n.) with 50 μg of OVA. Mice were given siNPRA8 oligonucleotide treatments by transdermal route and challenged 4 hours later. Following 24 hours of challenge two mice were sacrificed to obtain lungs and which were fixed sectioned and immunostained for NPRA expression (FIG. 7A). Mice (n=3) were sacrificed and lavaged and the percentage of eosinophils (FIG. 7B) and IL-4 concentration (FIG. 7C) in the lavage fluid was determined.
Figure 7B:
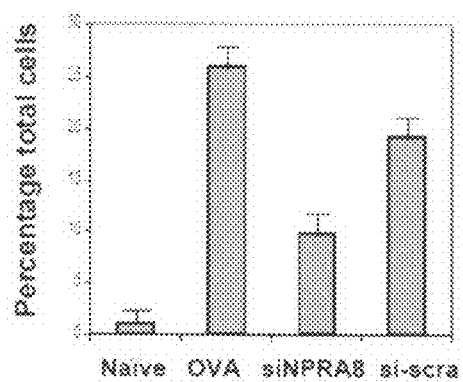
Figure 7C:
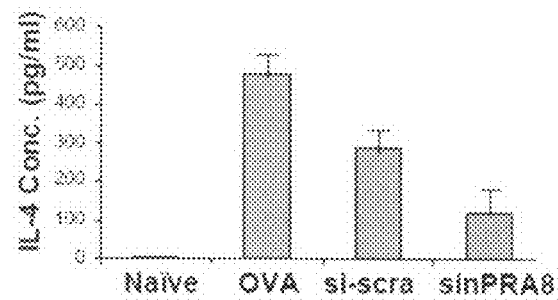
Figure 8A:
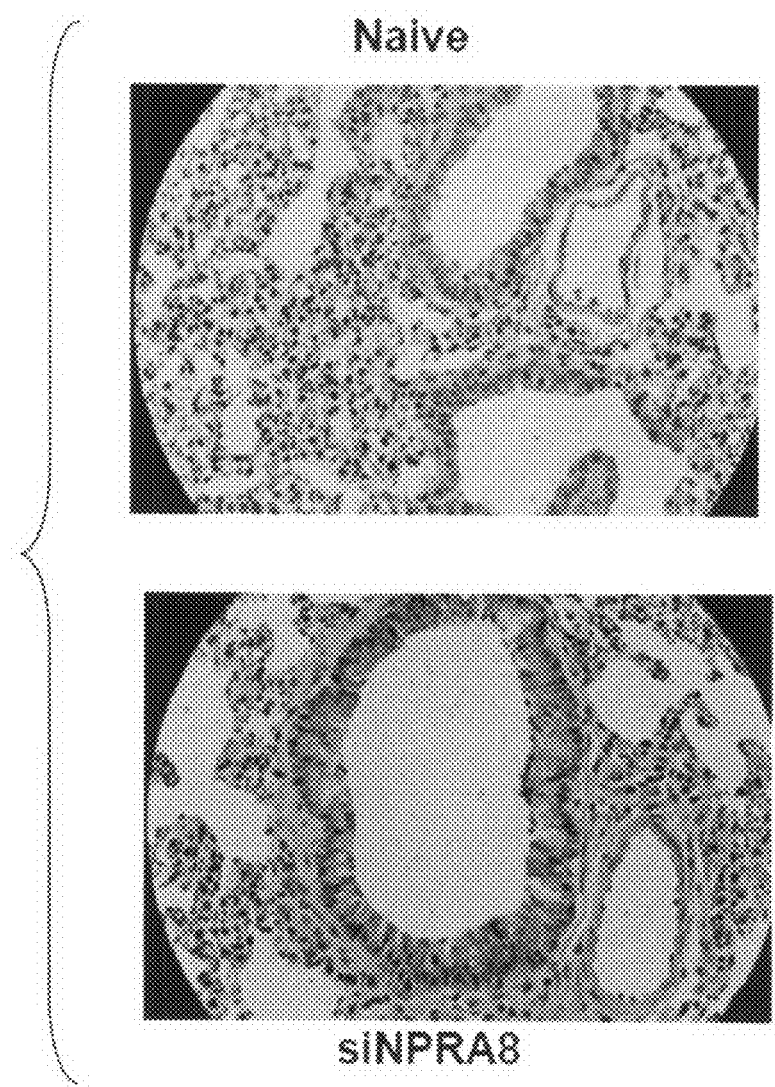
FIGS. 8A and 8B show that administration of siNPRA decreases inflammation of the lung in BALB/c mice. BALB/c mice (n=5 each group) were sensitized (i.p.) and challenged (i.n.) with 50 μg of OVA. All mice were sensitized intraperitoneally (i.p) and then challenged intranasally (i.n.) Mice were given siNPRA8 oligonucleotide treatments transdermally (si8) and challenged 4 hours later. Lungs were obtained 24 hours after challenge, fixed in formalin, sectioned and stained with hematoxylin and eosin.
Figure 8B:
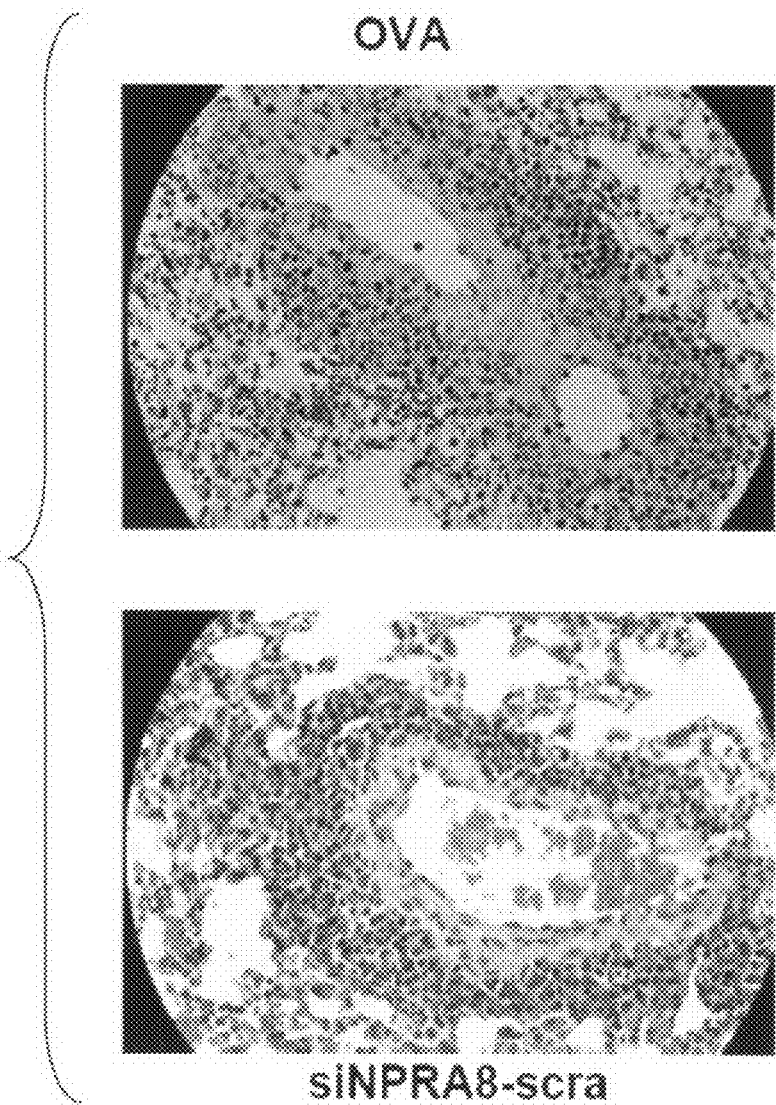
Figure 9:
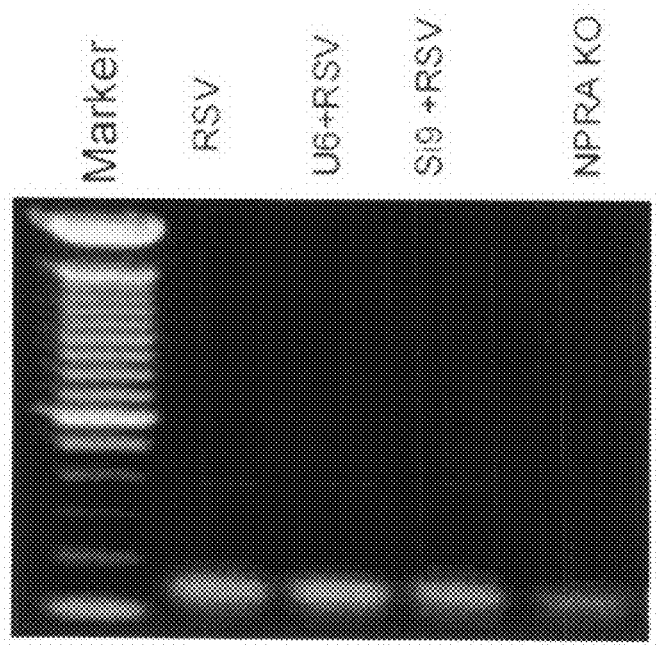
FIG. 9 shows that administration of siNPRA inhibits NPRA expression in the respiratory syncytial virus (RSV) infected lung. RT-PCR analysis of NPRA expression in the lung of mice treated with siRNA. psiNPRA9 was encapsulated with chitosan nanoparticles and intranasally delivered to mice. Twenty-four hours later, mice were infected with RSV ($5 \times 10^6$ pfu/mouse). Four days later, mice were sacrificed and lung were collected for RNA extraction. NPRA fragment were amplified by RT-PCR and analyzed in 1% agarose gel.
Figure 11:
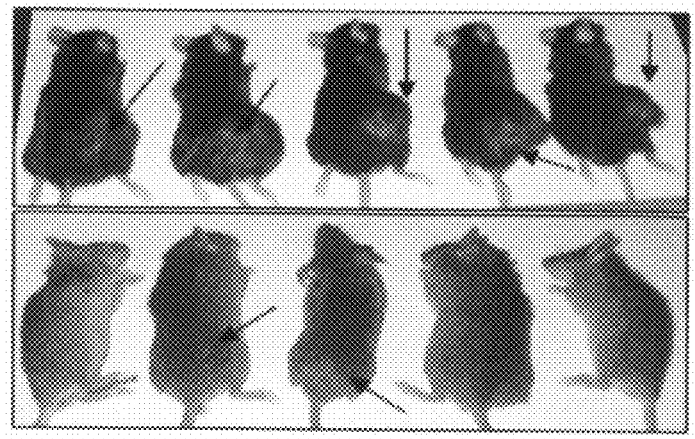
FIG. 11 shows that NPRA-deficient mice are resistant to melanoma tumor formation and metastasis in the B16 mouse model. B16 melanoma cells ($1.3 \times 10^5$) were injected subcutaneously into twelve-week-old female C57BL/6 mice and NPRA-deficient mice. Mice were observed for tumor formation for one month, then sacrificed on day-22. Tumors were then removed and weighed.
Figure 10B:
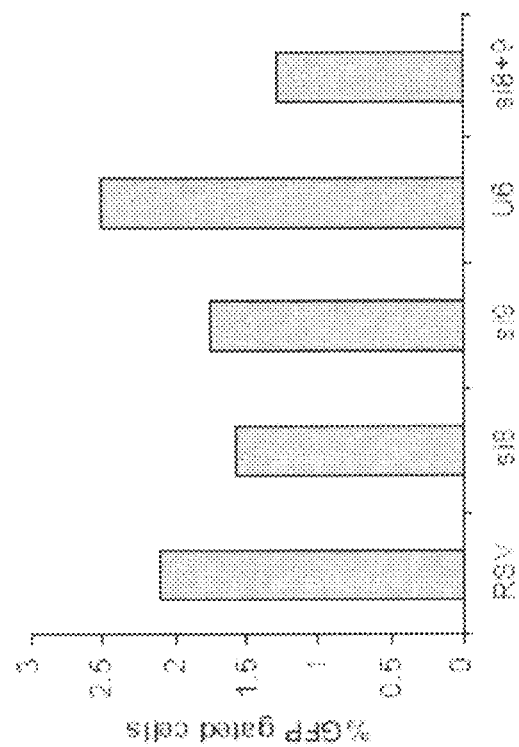
FIGS. 10A and 10B show that administration of siNPRA inhibits the Respiratory syncytial virus infection of A549 cells. A549 cells were grown in 6 well plate, transfected by siNPRA8, siNPRA9 or control U6 plasmid (2.0 ug) and 2 hours after infected by rgRSV (MOI=0.2). Cells were checked for infection 48 hours later, FACS was done. Results are shown in FIG. 10A. A549 cells were grown in 6 well plate infected by rgRSV (MOI=0.2) and 24 hours after infection they were transfected by siNPRA8, siNPRA9 or control U6 plasmid (2.0 μg) and further 24 hours later, flow cytometry was performed to estimate percentage of infected cells. Results are shown in FIG. 10B.
Figure 10A:
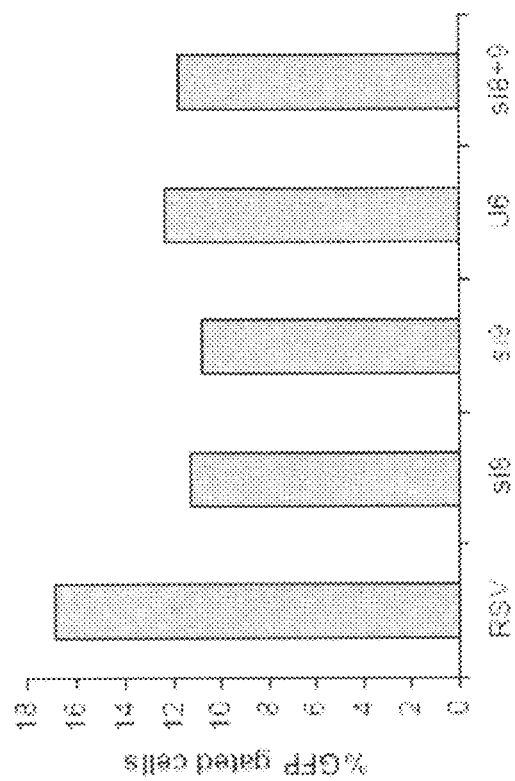
Figures 12A, 12B, 12C, 12D:
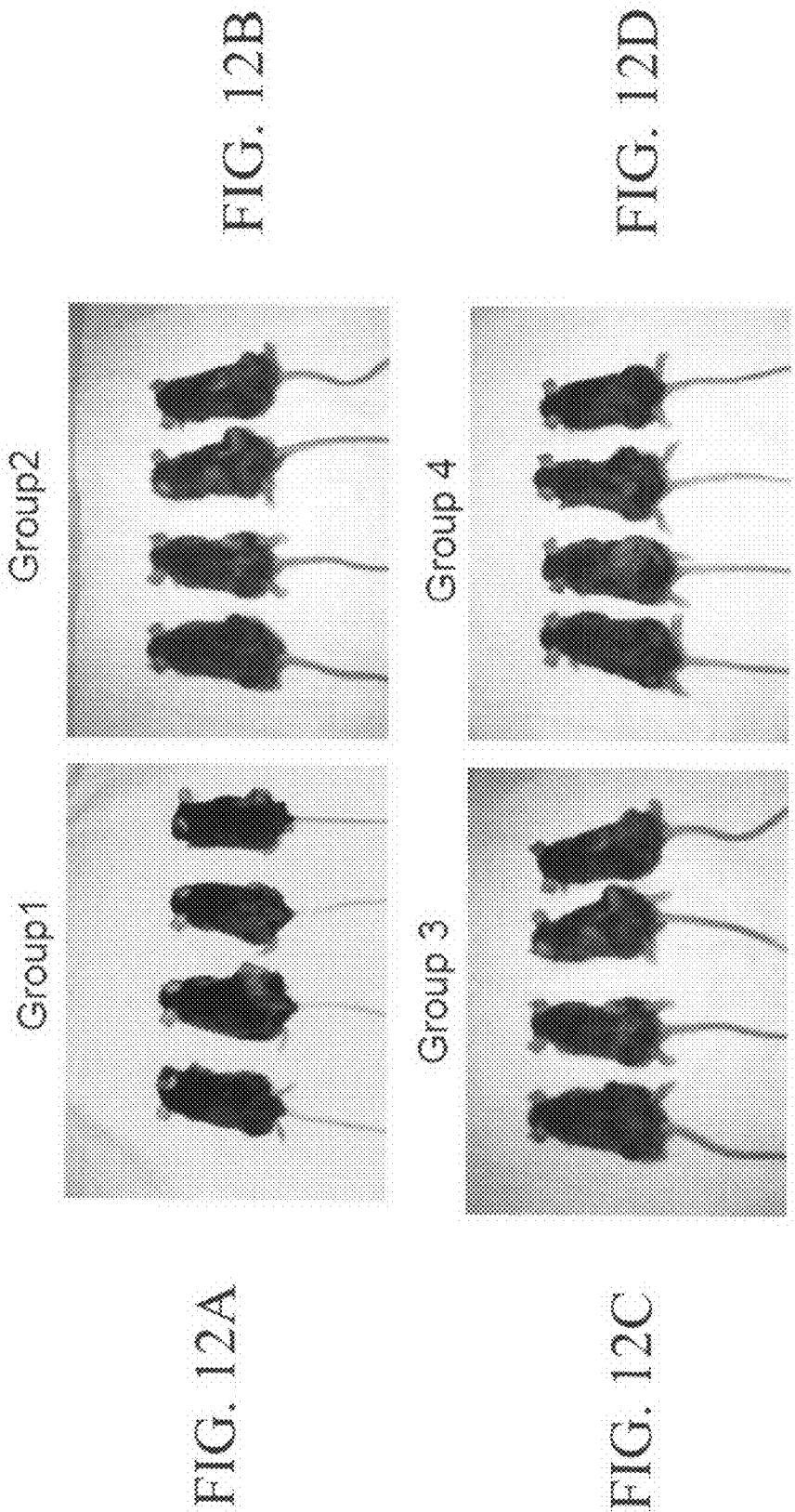
FIGS. 12A-12E show that siNPRA treatment decreases melanoma tumor formation in b16 mouse model. B16 melanoma cells ($1.3 \times 10^5$) were injected subcutaneously into twelve-week old female C57BL/6 mice. These mice were then treated with 33 μg of siNPRA-oligos, siNPRA plasmid, or scrambled oligos. All of these were mixed with chitosan at a ratio of 1:2.5. Mixed chitosan and plasmid or oligos were mixed again with cream before application to the injection area. The control group was given cream only. These treatments were given twice a week. Mice were sacrificed on day-22, and tumors were removed and weighed.
Figure 12E:
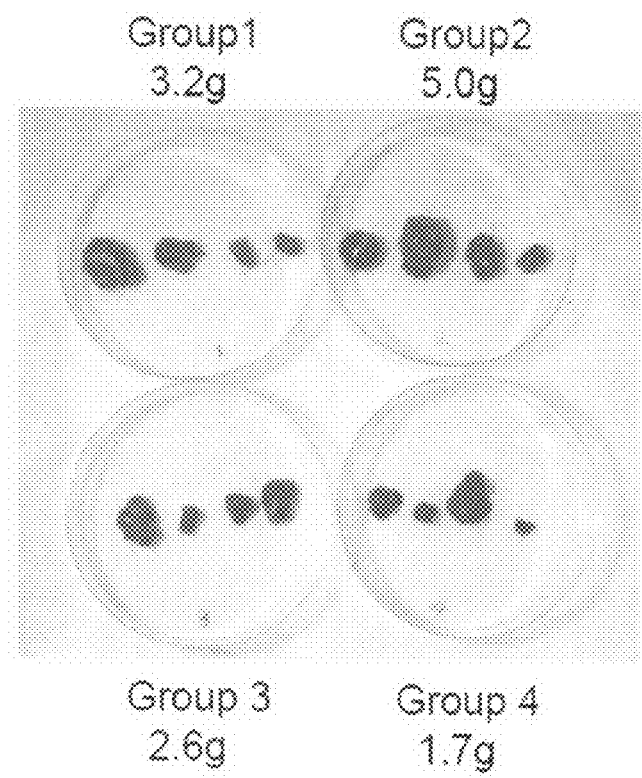
Figure 15:
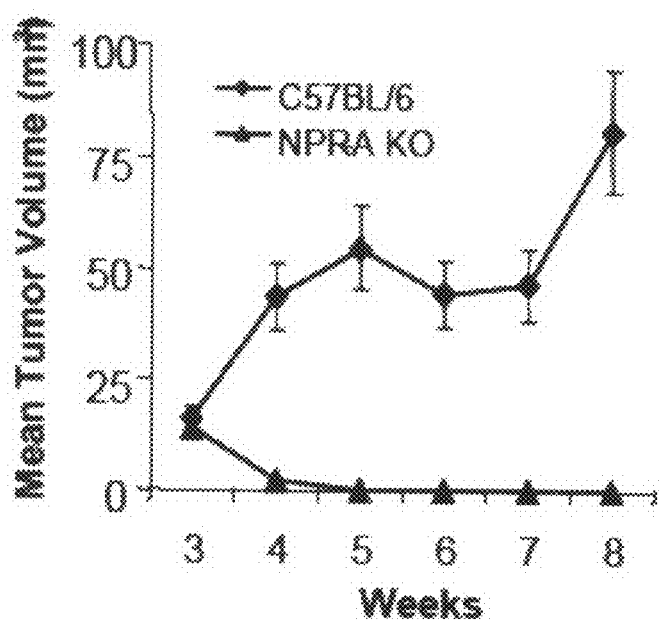
FIG. 15 shows that siNPRA treatment decreases ovarian cancer. Groups of wild type and NPRA$^{-/-}$ mice (n=8) were injected s.c. with $2 \times 10^6$ mouse ovarian cancer ID-8 cells and tumor sizes were measured every week after ID8 injection.

Results. Since intradermal delivery of siRNA has not been shown previously, the lung sections were first checked for the expression of NPRA and whether siRNA delivered by transdermal route decreases NPRA expression. The results are shown in FIG. 7A and indicate that lungs of ova-sensitized mice and mice treated with scrambled si-NPRA8 show higher number of cells expressing NPRA. siNPRA treatment decreased the expression level significantly. Typically, epithelial cells did not express NPRA and although not verified it is the dendritic cells appear to be involved in NPRA expression. The siNPRA8 treated mice also showed a significant reduction in eosinophil numbers (FIG. 7B) and levels of IL-4 (FIG. 7C) in the BAL. The results of H & E staining of lung sections showed that compared to untreated Ovalbumin-sensitized and mice treated with scrambled si-NPRA8 group, treated mice showed a significant reduction in lung inflammation (FIGS. 8A and 8B). There was a significant reduction in epithelial goblet cell hyperplasia and a significant reduction in peribroncial, perivascular and interstitial infiltration of the inflammatory cells to the lung. Together these results show that transdermal delivery of siNPRA8 decreases NPRA expression and inflammation of the lung and reduction of IL-4 and eosinophils in the lung.

EXAMPLE 5

Demonstration that Transfection of A549 Cells with psiNPRA9 Decreases the Number of Respiratory Syncytial Virus (RSV) Infection Infected Cells Respiratory syncytial virus infection also causes bronchiolitis in newborns and in elderly causing pneumonitis, which is characterized severe acute lung inflammation. RSV infection typically requires certain host cell proteins and transcription factors for its replication and subsequent infection of others cells. Since siNPRA treatment decreases pulmonary inflammation, the effect of siNPRA9 transfection on RSV infection was examined in pulmonary type-II epithelial cells was examined.

Materials and Methods. RT-PCR analysis of NPRA expression in the lung of mice treated with siRNA. psiNPRA9 was encapsulated with chitosan nanoparticles and intranasally delivered to mice. Twenty-four hours later, mice were infected with RSV ($5 \times 10^6$ pfu/mouse). Four days later, mice were sacrificed and lung cells were collected for RNA extraction. NPRA fragment were amplified by RT-PCR using NPRA specific primers (F:5'-GCA AAG GCC GAG TTA TCT ACA TC-3'(SEQ ID NO:5), R:5'-AAC GTA GTC CTC CCC ACA CAA-3(SEQ ID NO:6)) and analyzed in 1% agarose gel.

To determine the effect of siNPRA9 on RSBV infection of epithelial cells, A549 cells were grown in 6 well plate, transfected by siNPRA8, siNPRA9 or control U6 plasmid (2.0 ug) and 2 hours after infected by rgRSV (MOI=0.2). Cells were checked for infection 48 hours later, FACS was done. Also, A549 cells were grown in 6 well plate infected by rgRSV (MOI=0.2) and 24 hours after infection they were transfected by siNPRA8, siNPRA9 or control U6 plasmid (2.0 ug) and further 24 hr later, Flow cytometry was performed to estimate percentage of infected cells.

Results. The RT-PCR analysis showed that both RSV infected mice and mice infected with RSV and intranasally treated with pU6 control plasmid given with chitosan nanoparticles showed NPRA expression in the lung cells. However, mice infected with RSV and intranasally given psiNPRA9 showed an amplification product that was reduced in band intensity compared to cells from mice given pU6 plasmid. The lung cells from NPRA knock-out mice showed the band as well but it was reduced in intensity.

To determine the effect of siNPRA9 on rgRSV infection of A549 cells, either cells were grown in 6 well plate, transfected by siNPRA8, siNPRA9 or control U6 plasmid (2.0 ug) and 2 hours after infected by rgRSV (MOI=0.2) (prophylactic approach), or A549 cells were grown in 6 well plate infected by rgRSV (MOI=0.2) and 24 hours after infection they were transfected by siNPRA8, siNPRA9 or control U6 plasmid (2.0 ug) (therapeutic approach) and further 24 hr later, flow cytometry was performed to estimate percentage of infected cells. The results showed whether prophylactic approach or therapeutic approach the results showed a 20% reduction in rgRSV infected cells in cells treated with siNPRA8 and/or siNPRA9 compared to siU6 control plasmid. Thus these results show that siNPRA treatment can decrease RSV infection in addition to inflammation as seen in other studies.

EXAMPLE 6

Demonstration that siNPRA Treatment Decreases Melanoma Tumor Formation in B16 Mouse Model Because siNPRA molecules are deliverable by transdermal route and treatment with siNPRA decreases local and systemic inflammation, which has been recently attributed toward the origin of certain cancers, the effect of siNPRA on melanoma was tested. The neoplastic transformation of the melanocyte involves differential ability of the melanoma cell versus the melanocyte to cope with oxidative stress. Melanocytes produce reactive radicals and have a low level of antioxidant enzymes, responding to UV with a large but transient increase in superoxide anion whereas keratinocytes and fibroblasts do not. Also, the comparative resting levels of the subunits forming the transcription factor NFkB are altered between melanocytes and melanoma cells both under resting and UVB stimulated conditions (Chin, L et al. *Genes Dev,* 1998, 12(22):3467-348126). Thus, the effect of the role of NPRA in melanoma was investigated.

Materials and Methods. B16 melanoma cells ($1.3 \times 10^5$) were injected subcutaneously into twelve-week old female C57BL/6 mice or NPRA-deficient mice produced in B6 background. These mice were then treated with 33 μg of siNPRA-oligos, siNPRA9 plasmid, or scrambled oligos. All of these were mixed with Chitosan at ratio of 1:2.5. Mixed chitosan and plasmid or oligos were mixed again with cream before application to the injection area. The control group was given cream only. These treatments were given twice a week. Mice were sacrificed on day twenty second, tumors were removed and weighed.

Figure 13A:
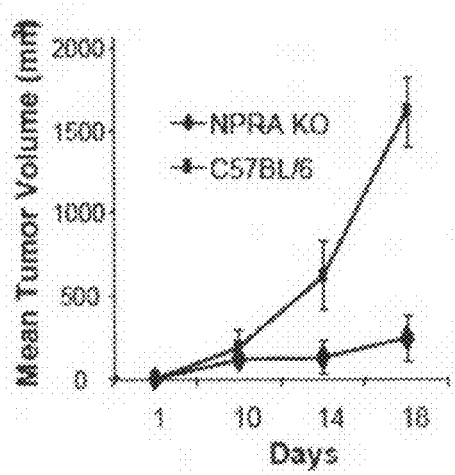
FIGS. 13A-13C show the effect of NPRA deficiency on melanoma. To test of the anti-melanoma activity of decreased NPRA levels, NPRA$^{-/-}$ mice (n=12) and wild type (n=12) were injected s.c. with B16 melanoma cells. The tumor size (FIG. 13A) over several days post injection and tumor burden (FIG. 13B) at day 18 were measured.
Figure 13B:
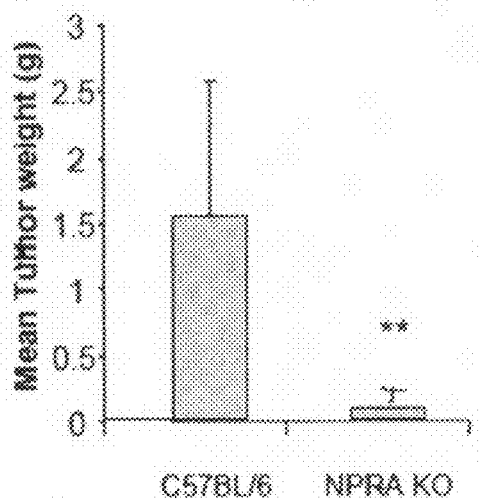

Results. To determine the role of NPRA in melanoma, groups of wild-type (WT) and NPRA$^{-/-}$ mice (n=8) were given subcutaneously $3 \times 10^5$ B16F10.9 cells and the tumor progression was observed after 14 days. The WT mice produced tumors whereas NPRA-/- mice did not have any tumors ANP pathway is a major pathway promoting melanoma tumors in C57BL/6-B16F10.9 model (FIGS. 12A-12E). To quantify the results, the tumor size and burden were measured in WT and NPRA$^{-/-}$ mice injected s.c. with B16 melanoma cells. A significant reduction ($P<0.01$) in mean tumor volume measured over 18 days after B16 cell injection and a significant decrease in tumor weight at day 18 was found in NPRA$^{-/-}$ mice (n=12) compared to WT (FIGS. 13A and 13B).

Figure 13C:
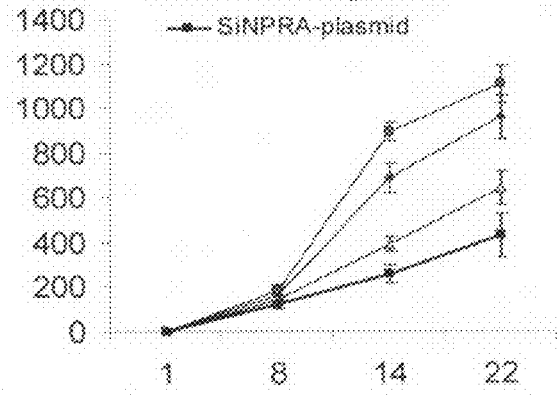
Figure 14A:
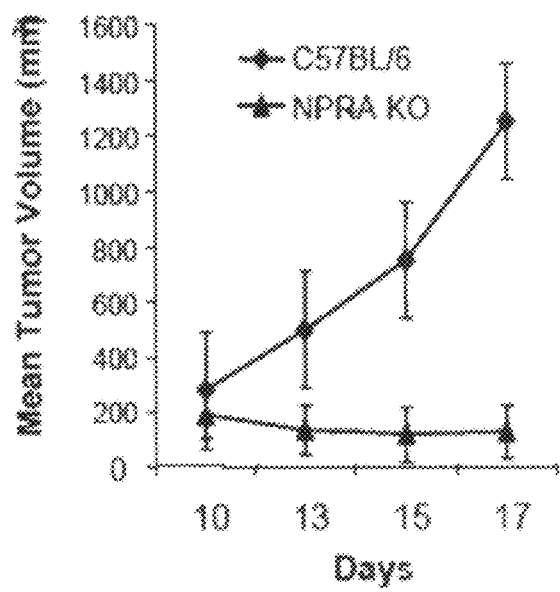
FIGS. 14A and 14B show that siNPRA treatment decreases lewis lung carcinoma. Groups of wild type and NPRA$^{-/-}$ mice (n=8 per group) were injected s.c. with $2 \times 10^6$ LLC1 cells. Tumor sizes were measured on day 10, 13, 15 and 17 (FIG. 14A) and tumor weights at day 17 (FIG. 14B) were compared.
Figure 14B:
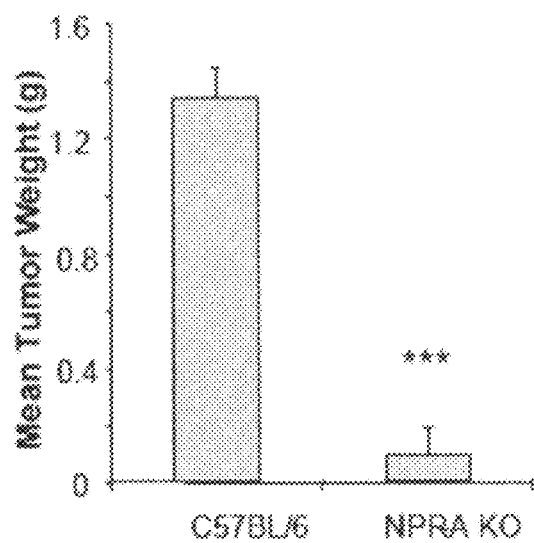

Since, NPRA-deficient mice may have other abnormalities which might make it resistant, the WT mice were injected with $3 \times 10^5$ B16F10.9 cells and were then treated with a cream containing siNPRA 9 given twice a week at the location of tumor cell injection. Three weeks later, both treated and control mice treated with cream alone without siNPRA were compared for their tumor burden. FIG. 13C shows a comparison of both groups of mice. Excision of these tumors revealed that siNPRA, but not siNPRA scrambled, showed significant reductions in tumor burden. These results together show that siNPRA can be used to treat melanomas.

EXAMPLE 7

Demonstration that siNPRA Treatment Decreases Melanoma Tumor Formation in Lewis Lung Carcinoma B16 Mouse Model Methods: For challenge with Lewis lung cancer cells, LLC1 cells grown in DMEM were washed with phosphate buffered saline (PBS) and resuspended in PBS at $2 \times 10^7$ cells per ml. Two groups of mice (n=8 per group) were tested: WT C57BL/6 mice and C57BL/6 NPRA-deficient mice. Animals were injected subcutaneously with $2 \times 10^6$ LLC1 cells (100 µl) in the right flank. Tumor sizes were measured at days 10, 13, 15 and 17 after injection. All animals were sacrificed on day 17 and the tumors were removed and weighed.

Results: Using the Lewis lung carcinoma model, C57BL/6 WT mice and NPRA gene knockout (NPRA$^{-/-}$) mice (n=8 for each group) were injected s.c. with $2 \times 10^6$ cells LLC1 cells in the right flank. Tumors appeared within one week after injection and tumor size was measured with a digital caliper beginning on day 10. The tumors in WT mice grew rapidly after day 10, but tumors in NPRA$^{-/-}$ mice gradually shrank. On day 17, all mice were sacrificed, and tumor sizes and weights were measured. In one of the NPRA$^{-/-}$ mice, there were no visible tumors at all. Significant differences ($P<0.001$) in tumor size and weight were observed between the two groups

EXAMPLE 8

Demonstration that siNPRA Treatment Decreases Melanoma Tumor Formation in ID8 Ovarian Cancer Mouse Model Methods: For challenge with ovarian cancer cells, ID-8 ovarian cancer cells grown in DMEM were washed with PBS and resuspended in PBS at $2 \times 10^7$ cells per ml. Two groups of mice (n=8 per group) were tested: WT C57BL/6 mice and C57BL/6 NPRA-deficient mice. Animals were injected subcutaneously with $2 \times 10^6$ ID8 cells (100 µl). Tumor sizes were measured at days 10, 13, 15 and 17 after injection. All animals were sacrificed on day 17 and the tumors were removed and weighed.

Results: Groups (n=8) of WT mice and NPRA-deficient C57BL/6 mice were injected with $2 \times 10^6$ ID8 mouse ovarian cancer cells at day 1 and mice were monitored at weekly intervals for tumor growth. By week 8 after cancer cell inoculation, all mice from the WT group developed solid tumors but no tumors were found in NPRA-deficient mice. The results indicate that NPRA deficiency significantly protects mice from ovarian cancer.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

---

We claim:

1. A method for reducing the expression of the atrial natriuretic peptide receptor A (NPRA) in a mammalian subject having lung cancer or melanoma, comprising administering an interfering RNA molecule or antisense molecule to the subject, wherein the interfering RNA molecule or antisense molecule is targeted to a nucleic acid sequence within the NPRA gene or transcript, and wherein the interfering RNA molecule or antisense molecule is administered in an effective amount to reduce NPRA expression, and lung cancer cell growth or melanoma cell growth, in the subject.

2. The method of claim 1, wherein the subject is human.

3. The method of claim 1, wherein the subject is a non-human mammal.

4. The method of claim 1, wherein the subject has lung cancer, and wherein the interfering RNA molecule or antisense molecule is delivered to respiratory epithelial cells within the subject.

5. The method of claim 1, wherein the subject has lung cancer, and wherein the interfering RNA molecule or antisense molecule is administered to the subject intranasally.

6. The method of claim 1, wherein the subject has lung cancer and the interfering RNA molecule or antisense molecule is administered intranasally as drops or as an aerosol, or orally; or wherein the subject has melanoma and the interfering RNA molecule or antisense molecule is administered transdermally.

7. The method of claim 1, wherein said administering comprises administering a combination of interfering RNA molecules to the subject.

8. The method of claim 1, wherein the interfering RNA molecule is administered to the subject, and wherein the interfering RNA molecule is an siRNA.

9. The method of claim 1, wherein the interfering RNA molecule or antisense molecule targets a region within the NPRA gene or transcript selected from the group consisting of the 5' untranslated region (UTR), transcription start site, translation start site, and 3' UTR.

10. The method of claim 1, wherein the interfering RNA molecule or antisense molecule is administered to dendritic cells or monocytes within the subject.

11. The method of claim 1, wherein the subject has lung cancer.

12. The method of claim 11, wherein the subject is human.

13. The method of claim 1, wherein the interfering RNA molecule is administered to the subject.

14. The method of claim 13, wherein the interfering RNA molecule is a small hairpin RNA (shRNA).

15. The method of claim 1, wherein the antisense molecule is administered to the subject.

16. The method of claim 1, wherein the interfering RNA molecule or antisense molecule is targeted to a nucleic acid sequence within an mRNA sequence encoded by SEQ ID NO:4.

* * * * *